(12) United States Patent
Lindsay et al.

(10) Patent No.: US 10,330,632 B2
(45) Date of Patent: *Jun. 25, 2019

(54) DEVICES AND METHODS FOR TARGET MOLECULE CHARACTERIZATION

(71) Applicant: Arizona Board of Regents on behalf of Arizona State University, Scottsdale, AZ (US)

(72) Inventors: Stuart Lindsay, Phoenix, AZ (US); Peiming Zhang, Gilbert, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 197 days.

This patent is subject to a terminal disclaimer.

(21) Appl. No.: 15/203,383

(22) Filed: Jul. 6, 2016

(65) Prior Publication Data
US 2017/0003245 A1 Jan. 5, 2017

Related U.S. Application Data

(63) Continuation of application No. 12/594,366, filed as application No. PCT/US2008/059602 on Apr. 7, 2008, now Pat. No. 9,395,352.
(Continued)

(51) Int. Cl.
*G01N 33/487* (2006.01)
*C12Q 1/68* (2018.01)
(Continued)

(52) U.S. Cl.
CPC ....... *G01N 27/3278* (2013.01); *C12Q 1/6869* (2013.01); *G01N 27/028* (2013.01); *G01N 27/3276* (2013.01); *G01N 33/48721* (2013.01)

(58) Field of Classification Search
CPC ....... G01N 33/48721; G01N 27/44791; G01N 27/447; C12Q 1/6869
(Continued)

(56) References Cited

U.S. PATENT DOCUMENTS 3,619,206 A 11/1971 Lawrence et al.
4,804,707 A 2/1989 Okamoto et al.
(Continued)

FOREIGN PATENT DOCUMENTS

EP 1261863 B1 2/2005
WO WO 1992001476 A1 2/1992
(Continued)

OTHER PUBLICATIONS

Ohshiro et al. "Complementary base-pair-facilitated electron tunneling for electrically pinpointing complementary nucleobases". In: Proc. Nat. Acad. Sci. (USA) Jan. 3, 2006, vol. 103, No. 1, pp. 10-14, especially abstract, p. 11 Fig 1. p. 14 right col. para 1.
(Continued)

*Primary Examiner* — Thanh Truc Trinh
(74) *Attorney, Agent, or Firm* — Schwabe, Williamson & Wyatt, P.C.

(57) ABSTRACT

An system for recognition of a translocating polymeric target molecule includes a device having at least one constriction that is sized to permit translocation of only a single copy of the molecule. A pair of spaced apart sensing electrodes border the constriction, which may be a nanopore. The first electrode is connected to a first affinity element and the second electrode is connected to a second affinity element. Each affinity element may connected to its corresponding electrode via one or more intermediary compounds, such as a linker molecule and/or an electrode attachment molecule. The first and second affinity elements are configured to temporarily form hydrogen bonds with first
(Continued)

and second portions of the target molecule as the latter passes through the constriction. During translocation, the electrodes affinity elements and first and second portions of the target molecule complete an electrical circuit and allow a measurable electrical current to pass between the first and second electrodes. The time-varying nature of this electrical current, and the specific affinity elements employed, allow one to characterize the target molecule.

21 Claims, 49 Drawing Sheets

Related U.S. Application Data

(60) Provisional application No. 61/022,155, filed on Jan. 18, 2008, provisional application No. 60/989,089, filed on Nov. 19, 2007, provisional application No. 60/922,288, filed on Apr. 6, 2007.

(51) Int. Cl.
 *G01N 27/327* (2006.01)
 *C12Q 1/6869* (2018.01)
 *G01N 27/02* (2006.01)

(58) Field of Classification Search
 USPC .................................. 204/403.01, 603, 450
 See application file for complete search history.

(56) References Cited

U.S. PATENT DOCUMENTS

| | | | |
|---|---|---|---|
| 5,066,716 | A | 11/1991 | Robey et al. |
| 5,879,436 | A | 3/1999 | Kramer et al. |
| 6,215,798 | B1 | 4/2001 | Carneheim et al. |
| 6,537,755 | B1 | 3/2003 | Drmanac |
| 6,627,067 | B1 | 9/2003 | Branton |
| 6,821,730 | B2 | 11/2004 | Hannah |
| 6,824,974 | B2 | 11/2004 | Pisharody et al. |
| 6,905,586 | B2 | 6/2005 | Lee et al. |
| 7,001,792 | B2 | 2/2006 | Sauer et al. |
| 7,033,476 | B2 | 4/2006 | Lee et al. |
| 7,282,130 | B2 | 10/2007 | Flory |
| 7,638,034 | B2 | 12/2009 | Sasinena et al. |
| 8,003,319 | B2 | 8/2011 | Polonsky et al. |
| 8,628,649 | B2 | 1/2014 | Lindsay et al. |
| 9,395,352 | B2 | 7/2016 | Lindsay et al. |
| 2002/0033345 | A1 | 3/2002 | Meade |
| 2002/0117765 | A1 | 8/2002 | Hinada et al. |
| 2003/0089605 | A1 | 5/2003 | Timperman |
| 2003/0099951 | A1 | 5/2003 | Akeson et al. |
| 2003/0148289 | A1 | 8/2003 | Sundararajan et al. |
| 2003/0203394 | A1 | 10/2003 | Eichen et al. |
| 2003/0215376 | A1 | 11/2003 | Chopra |
| 2004/0128081 | A1 | 7/2004 | Rabitz et al. |
| 2004/0144658 | A1 | 7/2004 | Flory |
| 2004/0262636 | A1 | 12/2004 | Yang et al. |
| 2005/0032053 | A1 | 2/2005 | Sampson |
| 2005/0095599 | A1 | 5/2005 | Pittaro et al. |
| 2005/0136408 | A1 | 6/2005 | Tom-Moy et al. |
| 2005/0202444 | A1 | 9/2005 | Zhu |
| 2005/0217990 | A1 | 10/2005 | Sibbett et al. |
| 2005/0227239 | A1 | 10/2005 | Joyce |
| 2006/0073489 | A1 | 4/2006 | Li et al. |
| 2006/0194228 | A1 | 8/2006 | Rakitin et al. |
| 2006/0211016 | A1 | 9/2006 | Kayyem et al. |
| 2006/0231419 | A1 | 10/2006 | Barth |
| 2006/0263255 | A1 | 11/2006 | Han et al. |
| 2007/0009379 | A1 | 1/2007 | Bau et al. |
| 2007/0292855 | A1 | 12/2007 | Dubin et al. |
| 2008/0050752 | A1 | 2/2008 | Sun et al. |
| 2008/0121534 | A1 | 5/2008 | White et al. |
| 2008/0171316 | A1 | 7/2008 | Golovchenko et al. |
| 2009/0198117 | A1 | 8/2009 | Cooper et al. |
| 2009/0298072 | A1 | 12/2009 | Ju et al. |
| 2009/0308741 | A1 | 12/2009 | Frey et al. |
| 2009/0309614 | A1 | 12/2009 | Goodman et al. |
| 2009/0326238 | A1 | 12/2009 | Burn et al. |
| 2010/0145626 | A1 | 6/2010 | Ecker et al. |
| 2010/0294659 | A1 | 11/2010 | Green |
| 2010/0310421 | A1 | 12/2010 | Oliver et al. |
| 2011/0120868 | A1 | 5/2011 | Lindsay et al. |
| 2011/0168562 | A1 | 7/2011 | Nuckolls et al. |
| 2012/0330001 | A1 | 12/2012 | Darzins et al. |
| 2013/0186757 | A1 | 7/2013 | Reinhart et al. |

FOREIGN PATENT DOCUMENTS

| | | |
|---|---|---|
| WO | WO 199957550 A1 | 11/1999 |
| WO | WO 2000192890 A1 | 12/2001 |
| WO | WO 2003031464 A2 | 4/2003 |
| WO | WO 2007084163 A2 | 7/2007 |
| WO | WO 2008124706 A2 | 10/2008 |
| WO | WO 2009017522 | 2/2009 |
| WO | WO 2008071982 A2 | 6/2009 |
| WO | WO 2009117517 A2 | 9/2009 |
| WO | WO 2009117522 | 9/2009 |
| WO | WO 2010042514 A1 | 4/2010 |
| WO | WO 2011097171 A1 | 8/2011 |

OTHER PUBLICATIONS

Porath et al. "Direct measurement of electrical transport through DNA molecules". In: Nature Feb. 10, 2000 vol. 403 pp. 635-638. Abstract only.

Shimmin et al. "Polymer Size and Concentration Effects on the Size of Gold Nanoparticles Capped by Polymeric Thiols". In: Langmuir Jun. 22, 2004 vol. 20 No. 13 pp. 5613-5620. Especially p. 5613 left col. pare 1.

Schug et al. "Noncovalent Binding between Guanidinium and Anionic Groups: Focus on Biological- and Synthetic-Based Arginine/Guanidinium Interactions with Phosph[on]ate and Sulf[on]ate Residues". In: Chemical Reviews, 2005, vol. 105, No. 1, pp. 67-113. Especially p. 88 left col. pore 2 and p. 88 Fig. 16.

Lee et al. "GC base sequence recognition by oligo(imidazolecarboxamide) and C-terminus-modified analogues of distamycin deduced from circular dichroism, proton nuclear magnetic resonance, and methidiumpropylethylenediami-neletraacetate4ron(II) foolprinting studies". In: Biochemistry Apr. 27, 1993 vol. 32 No. 16 pp. 4237-4245. Abstract only.

Walti et al. "Direct Selective Functionalization of Nanometer-Separated Gold Electrodes with DNA Oligonucleotides". In: Langmuir Feb. 2003 vol. 19 No. 4 pp. 981-984. Abstract only.

Peng et al. "Slowing down DNA translocation using magnetic and optical tweezers". In: American Physical Society, APS Mar. Meeting, Mar. 13-17, 2006, abstract #N26.010. Available online at «URL: http://meetings.aps.org/MeetinwMAR06/Event/42679» abstract only.

International Search Report to PCT/US08/59602 dated Sep. 22, 2008 (3 Pages).

Written Opinion, issued for International Application No. PCT/US08/59602, date of completion of report Sep. 22, 2008.

J. Mathe, A. Arinstein, Y. Rabin and A. Meller, "Equilibrium and irreversible unzipping of DNA in a nanopore", Europhysics Letters, 2006. 73: 128-134.

Y. Astier, O. Braha and H. Bayley, "Toward single molecule DNA sequencing: Direct identification of ribonucleoside and deoxyribonucleoside 5 '-monophosphates by using an engineered protein nanopore equipped with a molecular adapter", J. Am. Chem. Soc, 2006. 128: 1705-1710.

J. Nakane, M. Wiggin and A. Marziali., "A nanosensor for transmembrane capture and Identification of single nucleic acid molecules", Biophys J. 87:, 2004. 87: 615-621.

M. Akeson, D. Branton, JJ. Kasianowicz, E. Brand in and D.W.D. "Microsecond timescale discrimination among polycytidylic acid,

(56) References Cited

OTHER PUBLICATIONS polyadenylic acid, and polyuridylic acid as homopolymers or as segments within single RNA molecules", Biophys J., 1999. 77: 3227-3233.

Z. Siwy, L. Trofin, P. Kohli, L.A. Baker, C. Trautmann and CR. Martin, "Protein biosensors based on biofunctionalized conical gold nanotubes", J. Am. Chem. Soc, 2005. 127: 5000-5001.

JJ. Kasianowicz, Nanopores—Flossing with DNA, Nature Matis., 2004. 3: 355-356.

Muthukumar, "Theory of sequence effects on DNA translocation through proteins and nanopores", Electrophoresis, 2003. 23: 1417-1420.

P. Chen, JJ. Gu, E. Brandin, Y.R. Kim, Q. Wang and D. Branton, "Probing single DNA molecule transport using fabricated nanopores", Nano Lett., 2004. 4: 2293-2298.

S.B. Smith, L. Finzi and C. Bustamante, "Direct mechanical measurements of the elasticity of single DNA molecules by using magnetic beads", Science, 1992. 258: 1122-1126.

J. Kasianowicz, S. Henrickson, H. Weetall and B. Robertson, "Simultaneous multianalyte detection with a nanometer-scale pore", Anal. Chem., 2001. 73: 2268-2272.

M. Muthukumar, "Theory of sequence effects on DNA translocation through proteins and nanopores", Electrophoresis, 2003.23: 1417-1420.

A. Meller and D. Branton, "Single molecule measurements of DNA transport through a nanopore, Electrophoresis", 2002. 23: 2583-2591.

J. Li, D. Stein, D. Mccullan, D. Branton, MJ. Aziz and JA Golovchenko, "Ion-beam sculpting at Nanometer length scales", Nature, 2001. 412: 166-169.

A. Storm, J. Chen, X. Ling, H. Zandbergen and C. Dekker, "Fabrication of solid-state nanopores with single-nanometre precision", Nature Mat., 2003, 2003. 2: 537-540.

H. Chang et al. Towards Integrated Micro-machined silicon-based nanopores for characterization of DNA .. in Proc. of Hilton Head Conf. 2004. Hilton Head, SC.

H. Chang, S. Iqbal, E. Stach, A. King, N. Zaluzec and R. Bashir, "Fabrication and characterization of solid state nanopores using field emission scanning electron beam", App. Phys. Lett, 2006. 88: 103109.

MJ. Kim, M. Wanunu, D.C. Bell and A. Meller, "Rapid Fabrication of Uniformly Sized Nanopores and Nanopore Arrays for Parallel DNA Analysis", Advanced Materials, 2006. 18: 3149-3153.

H.A. Held, A. Roychowdhury and S.A. Benner, "C-5 modified nucleosides: Direct insertion of alkynyl-thio functionality in pyrimidines", Nucleosides, Nucleotides & Nucleic Acids, 2003. 22(4): 391-404. 35. P.

Chen, T. Mitsui, D.B. Farmer, J. Golovchenko, R.G. Gordon and D. Branton, "Atomic layer deposition to fine-tune the surface properties and diameters of fabricated nanopores", Nano Lett, 2004. 4: 1333.

A. Storm, J., J.H. Chen, H.W. Zandbergen and C. Dekker, "Translocation of double-strand DNA through a silicon oxide nanopore", Phys. Rev. E, 2005. 71:051903.

AJ. Storm, C. Storm, J.H. Chen, H. Zandbergen, W., J.-F. Joanny and C. Dekker, "Fast DNA translocation through a solid-state nanopore"., Nano Lett., 2005. 5: 1193.

D. Fologea, M. Gershow, B. Ledden, D.S. McNabb, J.A. Golovchenko and J. Li, "Detecting single stranded DNA with a solid state nanopore", Nano Lett., 2005. 5: 1905.

J.B. Heng, C. Ho, T. Kim, R. Timp, A. Aksimentiev, Y.V. Grinkova, S. Sligar, K. Schulten and G. Timp, "Sizing DNA using a nanometer-diameter pore", Biophys J., 2005. 87: 2905.

J. Heng, B., A. Aksimentiev, C. Ho, P. Marks, Y.V. Grinkova, S. Sligar, K. Schulten and G. Timp, "Stretching DNA using the electric field in a synthetic nanopore", Nano Lett., 2005. 5: 1883.

P. Chen, J. Gu, E. Brandin, Y. Kim, Q. Wand and D. Branton, "Probing single DNA molecule transport using fabricated nanopores", Nano Lett., 2004. 4: 2293.

S. Wilk, M. Goryll, G. Laws, S. Goodnick and T J. Thornton, "Teflon-coated silicon apertures for supported lipid bilayer membranes", App. Phy. Lett., 2004. 85: 3307-3309.

J.W. Lee and T. Thundat U.S. Pat. No. 6,905,586 Jun. 14, 2005.

M. Zwolak and M. Di Ventra, "Electronic Signature of DNA Nucleotides via Transverse Transport", Nano Lett., 2005. 5: 421-424.

J. Lagerqvist, M. Zwolak and M. Di Ventra, "Influence of the Environment and Probes on Rapid DNA Sequencing via Transverse Electronic Transport", Biophys J., 2007. 93: 2384-2390.

X.-G. Zhang, P.S. Krstic, R. Zikic, J.C. Wells and M. Fuentes-Cabrera, "First-Principles Transversal DNA Conductance Deconstructed", Biophys J., 2006. 91: L04-L06.

M.E. Gracheva, A. Xiong, A. Aksimentiev, K. Schulten, G. Timp and J.-P. Leburton, "Simulation of the electric response of DNA translocation through a semiconductor nanopore capacitor", Nanotechnology, 2006. 17: 622-633.

M. Zwolak and M. Di Ventra, "Physical approaches to DNA sequencing and detection", Reviews of Modern Physics, 2007. in press: available at arXIV: 0708.2724.

B. Ashcroft, Q. Spadola, S. Qamar, P. Zhang, G. Kada, R. Bension and S.M. Lindsay, "An AFM/Rotaxane Molecular Reading Head for Sequence-Dependent DNA Structure", J. Am. Chem. Soc, 2007. Submitted.

A. Salomon, D. Cahen, S. Lindsay, J. Tomfohr, V.B. Engelkes and CD. Frisbie, "Comparison of electronic transport measurements on organic molecules", Advanced Materials, 2003. 15: 1881-1890.

D.D. Dunlap, R. Garcia, E. Schabtach and C. Bustamante, "Masking generates contiguous segments of metal coated and bare DNA for STM imaging.", Proc. Natl. Acad. Sci. (USA), 1993. 90: 7652-7655.

D. Porath, A. Bezryadin, S. de Vries and C. Dekkar, "Direct measurement of electrical transport through DNA molecules", Nature, 2000. 403: 635-638. 54. H.-W. Fink and C. Schoenberger, Electrical conduction through DNA molecules, Nature, 1999. 398: 407-410.

H.-W. Fink and C. Schoenberger, "Electrical conduction through DNA molecules", Nature, 1999. 398: 407-410.

A. Y. Kasumov, M. Kociak, S. Gueron, B. Reulet, V.T. Volkov, D.V. Klinov and H. Bouchiat, "Proximity-Induced Superconductivity in DNA", Science, 2001. 291: 280-282.

B. Xu, P.M. Zhang, X.L. Li and NJ. Tao, "Direct Conductance Measurement of Single DNA Molecules in Aqueous Solution", Nanoletts., 2004. 4: 1105-1108.

J. Tomfohr and O.F. Sankey, "Complex bandstructure, decay lengths and Fermi level alignment in simple molecular electronic systems", Phys. Rev. B, 2002. 65: 245105-245105-245112.

J. Tomfohr and O.F. Sankey, "Simple estimates of the electron transport properties of molecules", Phys. Stat. Sol. B—Basic Research, 2002. 233: 59-69.

T. Smith, "The hydrophillic nature of a clean gold surface", J. Colloid Interface Sci., 1980. 75: 51-53.

R.N. Baraett, CL. Cleveland, A. Joy, U. Landman and G.B. Schuster, "Charge Migration in DNA: Ion-Gated Transport.", Science, 2001. 294: 567-571.

X.D. Cui, A. Primak, X. Zarate, J. Tomfohr, O.F. Sankey, A.L. Moore, T. A. Moore, D. Gust, H. G. and S.M. Lindsay, "Reproducible measurement of single-molecule conductivity", Science, 2001. 294: 571-574.

T. Morita and S.M. Lindsay, "Determination of Single Molecule Conductances of Alkanedithiols by Conducting-Atomic Force Microscopy with Large Gold Nanoparticles", J. Am. Chem. Soc, 2007. 129: 7262-7263.

O.S. Wenger, Leigh, S., Villahermosa, RM., Gray, H.B., Winkler, J.R., "Electron Tunneling through Organic Molecules in Frozen Glasses", Science, 2005. 307: 99-102.

X.D. Cui, X. Zarate, J. Tomfohr, A. Primak, A.L. Moore, T.A. Moore, D. Gust, G. Harris, O.F. Sankey and S.M. Lindsay, "Making electrical contacts to molecular monolayers", Nanotechnology, 2002. 13: 5-14.

J.M.v. Ruitenbeek, Quantum point contacts between metals, in Mesoscopic electron transport, LL. Sohn, LP. Kouwenhoven, and G. Schon, Editors. 1997, Kluwer Academic Publishers: Amsterdam, p. 549-579.

(56) References Cited

OTHER PUBLICATIONS

C. Walti, R. Wirtz, W.A. Germishuizen, D.M.D. Bailey, M. Pepper, A.P.J. Middelberg and A.G. Davies, "Direct Selective Functionalization of Nanometer Separated Gold Electrodes with DNA Oligonucleotides", Langmuir, 2003. 19: 981-984.
C.J. Muller, J.M. Van Ruitenbeek and L.J. de Jong, "Experimental observation of the transition from weak link to tunnel junction", Physica C, 1992. 191: 485-504.
C.-J. Lo, T. Aref and A. Bezryadin, "Fabrication of symmetric sub-5 nm nanopores using focused ion and electron beams", Nanotechnology, 2006. 17: 3264-3267.
X. Yang and G. Zhang, "Simulating the Structure and Effect of the Electrical Double Layer at Nanometer Electrodes", Nanotechnology, 2007. 18: 33, 335201-335209.
N.B. Leontis, J. Stombaugh and E. Westhof, The non-Watson-Crick base pairs and their associated isostericity matrices, Nucleic Acids Research, 2002. 30(16): 3497-3531.
M. Egholm, O. Buchardt, L. Christensen, C Behrens, S.M. Freier, D. A. Driver, R.H. Berg, S.K. Kim, B. Norden, and P. E. Nielsen, "PNA hybridizes to complementary oligonucleotides obeying the Watson-Crick hydrogen-bonding rules", Nature, 1993. 365: 566-568.
D. Loakes, The Applications of universal DNA base analogues, Nucleic Acids Research, 2001. 29(12): 2437-2447.
Z. Guo, Q. Liu and L.M. Smith, "Enhanced discrimination of single nucleotide polymorphisms by artificial mismatch hybridization", Nature Biotechnology, 1997. 15: 331-335. 127.
D. Burgner, M. D'Amato, D.P. Kwiatkowski and D. Loakes, "Improved Allelic Differentiation Using Sequence-Specific Oligonucleotide Hybridization Incorporating an Additional Base-Analogue Mismatch", Nucleosides, Nucleotides and Nucleic Acids, 2004. 23(5): 755-765.
J. Luo, D.E. Bergstrom and F. Barany, "Improving the fidelity of Thermus thermophilus DNA ligase", Nucleic Acids Research, 1996. 24(14): 3071-3078.
H. Challa, M.L. Styers and S. A. Woski, "Nitroazole Universal Bases in Peptide Nucleic Acids", Org. Lett, 1999. 1(10): 1639-1641.
P. Zhang, M. Egholm, N. Paul, M. Pingle and D.E. Bergstrom, "Peptide Nucleic Acid-DNA Duplexes Containing the Universal Base 3-Nitropyrrole.", Methods, 2001. 23(2): 132-140.
B. Lohse, P.S. Ramanujam, S. Hvilsted and R.H. Berg, "Photodimerization in pyrimidine-substituted dipeptides", J. Peptide Sci., 2005. 11: 499-505.
R.H.E. Hudson, G. Li and J. Tse, The use of Sonogashira coupling for the synthesis of modified uracil peptide nucleic acid, Tetrahedron Letters 2002. 43 1381-1386.
N. Peyret, P.A. Seneviratne, H.T. Allawi and J. John SantaLucia, Nearest-Neighbor Thermodynamics and NMR of DNA Sequences with Internal A.A, CC, G.G, and T.T Mismatches, Biochemistry 1999. 38(12): 3468-3477.
H.T. Allawi and J. John Santalucia, "Thermodynamics and NMR of Internal GaT Mismatches in DNA", Biochemistry 1997. 36(34): 10581-10594.
K. Seio, T. Sasami, A. Ohkubo, K. Ando and M. Sekine, Highly Selective Recognition of Cytosine over Uracil and Adenine by a Guanine Analogue, 2-N-Acetyl-3-deazaguanine, in 2'-0-Methyl-RNA/RNA and DNA Duplexes, J. Am. Chem. Soc., 2007. 129(5): 1026-1027.
J. A. Doudna and J.H. Cate, "RNA structure: crystal clear?", Current Opinion in Structural Biology 1997. 7: 310-316.
J.C. Parham and M.A. Templeton, Comparative Reactivities of Esters of Oncogenic and Nononcogenic Purine N-Oxides and Evidence of the Oxidation-Reduction Reactivity of Aromatic Nitrenium Ions, Cancer Research, 1980. 40: 1475-1481.
B.K. Sarmah and N.C. Barua, Al—NiCl 2.6H20-THF: A New, Mild and Neutral System for Selective Reduction of Organic Functional Groups, Tetrahedron 1991. 41(40): 8587-8600.
M. Pauvert, P. Laine, M. Jonas and O. Wiest, Toward an Artificial Oxidative DNA Phtolyase, J. Org. Chem, 2004. 69(2): 643-648.
Z. Sun, S. Ahmed and L. W. McLaughlin, "Synthesis of Pyridine C-Nucleosides as Analogues of the Natural Nucleosides dC and dU", J. Org. Chem, 2006. 71(7): 2922-2925.
N. Ramzaeva and F. Seela. 7-Substituted 7-deaza-2'-deoxyguanosines: regioselective halogenation of pyrrolo[2,3-d] pyrimidine nucleosides. Helvetica Chimica Acta 1995. 78(5): 1083-1090.
H.C. Koppel, R.H. Springer, R.K. Robins and CC. Cheng, Pyrimidines. I. Synthesis of Pyyimidinethiols, J. Org. Chem, 1961. 26(3): 792-803.
J. John Santalucia, R. Kierzek and D.H. Turner, Stabilities of Consecutive AC, CC, GoG, UC, and UmU Mismatches in RNA Internal Loops: Evidence for Stable Hydrogen-Bonded U4J and CC+ Pairs, Biochemistry 1991. 30(33):8242-8251.
H. T. Allawi and J. John SantaLucia, Nearest-Neighbor Thermodynamics of Internal A:C Mismatches in DNA: Sequence Dependence and pH Effects, Biochemistry 1998. 37(26): 9435-9444. 145.
S.S. Mallajosyula and S.K. Pali, Effect of Protonation on the Electronic Properties of DNA Base Pairs: Applications for Molecular Electronics, J. Phys. Chem. B, 2007.111: 11614-11618.
K.-Y. Lin and M. D. Matteucci, A Cytosine Analogue Capable of Clamp-Like Binding to a Guanine in Helical Nucleic Acids, J. Am. Chem. Soc., 1998. 120(33): 8531-8532.
S.C. Holmes, A.A. Arzumanov and MJ. Gait, "Steric inhibition of human immunodeficiency virus type-1 Tat-dependent transactivation in vitro and in cells by oligonucleotides containing 2o-0-methyl G-clamp ribonucleoside analogues", Nucleic Acids Research, 2003. 31(11): 2759-2768.
C. Cheong, J. Ignacio Tinoco and A. Chollet, "Thermodynamic studies of base pairing involving 2,6-diaminopurine", Nucleic Acids Research, 1988. 16(11): 5115-5122.
S. A. Strobel, T.R. Cech, N. Usman and L. Beigelmad, "The 2,6-Diaminopurine Riboside5-Methylisocytidine Wobble Base Pair: An Isoenergetic Substitution for the Study of GU Pairs in RNA", Biochemistry 1994. 33(46): 13824-13835.
B.L. Gaffhey, L. A. Marky and R. A. Jones, "Synthesis and physical characterization of d[CGT(2-NH2)ACG], d[CGU(2-NH2 ACG] and d[CGT(2-NH2)AT(2-NH2)ACG]", Tetrahedron 1984. 40(1): 3-13.
J. Booth, W.J. Cummins and T. Brown, "An analogue of adenine that forms an "A:T" base pair of comparable stability to G:C", Chem. Commun . 2004. 10: 2208-2209.
S.W. Schneller and R.S. Hosmane, "Chlorination of IH-pyrrolo[3,2-c]pyridine-4,6(5H,7H)-dione (3,7-dideazaxanthine) and its 5-methyl derivative", Journal of Heterocyclic Chemistry, 1978. 15(2): 325-326.
H. Yamamoto, T. Terasawa, A. Nakamura, K. Kawabata, H. Takasugi, H. Tanaka, S. Matsumoto, Y. Matsumoto and S. Tawara, "Orally Active Cephalosporins. Part 3: Synthesis, Structure-Activity Relationships and Oral Absorption of Novel C-3 Heteroarylmethylthio Cephalosporins", Bioorganic & Medicinal Chemistry, 2001. 9: 465-475.
D. E. Bergstrom and P. Zhang, An efficient route to C-4 linked imidazole nucleosides: synthesis of 2-carbamoyl-4-(2'-deoxy-b-D-ribofurinosyl)imidazole, Tetrahedron Letters, 1991. 32(45): 6485-6488.
KJ. Merchant, "Potassium trimethylsilanolate mediated hydrolysis of nitriles to primary amides", Tetrahedron Letters, 2000.41:3747-3749.
B.R. Brooks, R.E. Bruccoleri, B.D. Olafson, DJ. States, S. Swaminathan and M. Karplus, "Charmm—a Program for Macromolecular Energy, Minimization, and Dynamics Calculations", Journal of Computational Chemistry, 1983. 4(2): 187-217.
D. A. Pearlman, D.A. Case, J.W. Caldwell, W.R. Ross, I. T.E. Cheatham, S. DeBolt, D. Ferguson, G. Seibel and P. Kollman, "AMBER, a computer program for applying molecular mechanics, normal mode analysis, molecular dynamics and free energy calculations to elucidate the structures and energies of molecules", Comp. Phys. Commun., 1995. 91: 1-41.
M.W. Schmidt, K.K. Baldridge, J.A. Boatz, S.T. Elbert, M.S. Gordon, J.H. Jensen, S. Koseki, N. Matsunaga, K.A. Nguyen, SJ. Su, T.L. Windus, M. Dupuis and J.A. Montgomery, "General Atomic and Molecular Electronic-Structure System", Journal of Computational Chemistry, 1993.14(11): 1347-1363.

(56) References Cited

OTHER PUBLICATIONS

R. A. Kendall, E. Apra, D.E. Bernholdt, EJ. Bylaska, M. Dupuis, G.I. Fann, RJ. Harrison, JX Ju, J A Nichols J Nieplocha T P Straatsma, T.L. Windus and A.T. Wong, "High performance computational chemistry: An overview of NWChem a distributed parallel application", Computer Physics Communications, 2000. 128(1-2): 260-283.

G. Kresse and J. Furthmuller, Efficient iterative schemes for ab initio total-energy calculations using a plane-wave basis set, Phys. Rev. B, 1996. 55: 11169-11186.

Baroni, S.d. Gironcoli and A.D. Corsa, www.pwscf.org.

O.F. Sankey and DJ. Niklewski, "Abinitio Multicenter Tight-Binding Model for Molecular-Dynamics Simulations and Other Applications in Covalent Systems", Physical Review B, 1989. 40(6): 3979-3995.

P. Jelinek, H. Wang, J.P. Lewis, O.F. Sankey and J. Ortega, "Multicenter approach to the exchange-correlation interactions in ab initio tight-binding methods", Physical Review B, 2005. 71(23).

P. Ordejon, E. Artacho and J.M. Soler, "Self-consistent order-N density functional calculations for very large systems", Phys. Rev. B, 1996. 53: 10441-10444.

A.P. Horsfield, P .D. Godwin, D.G. Pettifor and A.P. Sutton, "Computational materials synthesis .1. A tight-binding scheme for hydrocarbons", Physical Review B, 1996. 54(22): 15773-15775.

U.F. Keyser, B.N. Koelman, S. van Dorp, D. Krapf, R.M.M. Smeets, S.G. Lemay, N.H. Dekker and C. Dekker, "Direct forcemeasurements on DNA in a solid-state nanopore", Nature Physics, 2006. 2: 473-477.

C. Bustamante, J.C. Macosko and G. JX. Wuite, "Grabbing the cat by the tail: Manipulating molecules one by one.", Nature Reviews Molecular Cell Biology, 2000. 1: 130-136.

C. Gosse and V. Croquette, "Magnetic Tweezers: Micromanipulation and Force Measurement at the Molecular Level", Biophys J., 2002. 82: 3314-3329.

H. Shang and G. U. Lee, "Magnetic Tweezers Measurement of the Bond Lifetime-Force Behavior of the IgG-Protein a Specific Molecular Interaction", J. Am. Chem. Soc., 2007. 129: 6640-6646.

X.D. Cui, X. Zarate, J. Tomfohr, A. Primak, AL. Moore, T.A. Moore, D. Gust, G. Harris, O.F. Sankey and S.M. Lindsay, "Bias Induced Forces and Contact charging of organic monolayers", Ultramicroscopy, 2002. 92: 67-76.

X.D. Cui, A. Primak, X. Zarate, J. Tomfohr, O.F. Sankey, AL. Moore, T.A. Moore, D. Gust, L.A. Nagahara and S.M. Lindsay, "Changes in the electronic properties of a molecule when it is wired into a circuit", J. Phys. Chem B, 2002. B 106: 8609-8614.

J.K. Tomfohr and O.F. Sankey, "Theoretical analysis of electron transport through organic molecules", J. Chem. Phys., 2004. 120: 1542-1554.

G.K. Ramachandran, A.M. Rawlett, T J. Hopson, L.A. Nagahara, R.K. Tsui and S.M. Lindsay, "Organic molecules in an electrical circuit: an AFM study of a negative differential resistance molecule", Materials Research Society Symposium Proceedings, 2002. 728(Functional Nanostructured Materials through Multiscale Assembly and Novel Patterning Techniques): 211-215.

E. Gomar-Nadal, G.K. Ramachandran, F. Chen, T. Burgin, J. Veciana, C. Rovira, D. Amabilino and S.M. Lindsay, "Self-Assembled Monolayers of TIF Derivatives on Gold: Characterization and Electron Transport Studies", J. Chem. Phys., 2004. 108: 7213-7218.

A. Rawlett, T J. Hopson, L. Nagahara, R. Tsui, G. Ramachandran and S. Lindsay, "Electrical measurements of dithiolated electronic molecules via conducting atomic force," Appl. Phys. Lett. 81, 3043 (2002).

G.K. Ramachandran, T J. Hopson, AM. Rawlett, L. A. Nagahara, A. Primak and S.M. Lindsay, "A Bond-Fluctuation Mechanism for Stochastic Switching in Wired Molecules", Science, 2003. 300: 1413-1415.

G.K. Ramachandran, J.K. Tomfohr, O.F. Sankey, J. Li, X. Zarate, A. Primak, Y. Terazano, T.A. Moore, AL. Moore, D. Gust, L.A. Nagahara and S.M. Lindsay, "The Electron Transport Properties of a Carotene Molecule in a Metal-(Single-Molecule)-Metal Junction", J. Chem. Phys. B, 2003. 107: 6162-6169.

S.M. Lindsay, "Single Molecule Electronics and Tunneling in Molecules", Jap. J. Appl. Phys., 2002. 41: 4867-4870.

S.M. Lindsay, "Single Molecule Electronics", Interface, 2004. 3: 26-30.

D.M. Adams, L. Brus, C.E.D. Chidsey, S. Creager, C. Creutz, CR. Kagan, P.V. Kamat, M. Lieberman, S. Lindsay, R.A. Marcus, R.M. Metzger, M.E. Michel-Beyerle, J.R. Miller, M.D. Newton, D.R. Rolison, O. Sankey, K.S. Schanze, J. Yardley and X. Zhu, "Charge Transfer on the Nanoscale: Current Status", J. Phys. Chem., 2003. 107: 6668-6697.

J.K. Tomfohr, O.F. Sankey and S. Wang, "Rapid tunneling transit times for electrons and photons through periodic fragments", Phys. Rev. B, 2002. 66: 235105.

B. Xu and NJ. Tao, "Measurement of Single-Molecule Resistance by Repeated Formation of Molecular Junctions", Science, 2003. 301: 1221-1223.

F. Chen, J. He, C. Nuckolls, T. Roberts, J. Klare and S.M. Lindsay, "A molecular switch based on potential-induced changes of oxidation state", Nano Letters, 2005. 5: 503-506.

J. He, F. Chen, P.A. Liddell, J. Andreasson, S.D. Straight, D. Gust, T.A. Moore, A.L. Moore, J. Li, O.F. Sankey and S. M. Lindsay, "Switching of a photochromic molecule on gold electrodes: single molecule measurements", Nanotechnology, 2005. 16: 695-702.

J. He, F. Chen, J. Li, O.F. Sankey, Y. Terazono, C. Herrero, D. Gust, T.A. Moore, A.L. Moore and S.M. Lindsay, "Electronic Decay Constant of Carotenoid Polyenes from Single-Molecule Measurements", J. Am. Chem. Soc. (Communication), 2005. 127: 1384-1385.

J. He and S. Lindsay, "On the mechanism of negative differential resistance in ferrocenylundecanethiol self-assembled monolayers", J. Am. Chem. Soc, 2005. 127: 11932-11933.

J. Tomfohr, G. Ramachandran, O.F. Sankey and S.M. Lindsay, "Making contacts to single molecules: Are we nearly there yet? In Introducing Molecular Electronics", G. Fagas and K. Richter, Editors. 2005, Springer: Berlin, p. 301-312.

J. He, Q. Fu, S.M. Lindsay, J.W. Ciszek and J.M. Tour, "Electrochemical Origin of Voltage-Controlled Molecular Conductance Switching", J. Am. Chem. Soc, 2006. 128: 14828-14835.

I. Visoly-Fisher, K. Daie, Y. Terazono, C. Herrero, F. Fungo, L. otero, E. Durantini, JJ. Silber, L. Sereno, D. Gust, T.A. Moore, A.L. Moore and S.M. Lindsay, "Conductance of a biomolecular wire", Proc. Nat. Acad. Sci., 2006. 103:8686-8690.

X. Li, J. He, J. Hihath, B. Xu, S.M. Lindsay and NJ. Tao, "Conductance of Single Alkanedithiols: Conduction Mechanism and Effect of Molecule-Electrode Contacts", J. Am. Chem. Soc, 2006. 128: 2135-2141.

J. He and S.M. Lindsay, "Measuring Single Molecule Conductance with Break Junctions", Faraday Discussions, 2006. 131: 145-154. 87.

L. Venkataraman, Klare, J.E., Tarn, I. W., Nuckolls, C, Hybertsen, M.S., Steigerwald, M.L., "Single-Molecule Circuits with Well-Defined Molecular Conductance", Nano Lett., 2006. 6: 458-462.

L. Venkataraman, J.E. Klare, C. Nuckolls, M.S. Hybertsen and M.L. Steigerwald, "Dependence of single-molecule junction conductance on molecular conformation", Nature, 2006. 442: 905-907.

S.M. Lindsay, "Molecular wires and devices: Advances and issues", Faraday Discussions, 2006. 131 : 403-409.

J. He, L. Lin, P. Zhang and S.M. Lindsay, "Identification of DNA base-pairing via tunnel-current decay", Nano Letters, 2007. accepted for publication.

K. A. Henningfeld, T. Arsian and S.M. Hecht, Alteration of DNA primary structure by DNA topoisomerase I. Isolation of the covalent topoisomerasel—DNA binary complex in enzymatically competent form, J. Am. Chem. Soc, 1996. 118: 11701-11713.

K.E. Yelm, "A Simple Method for in situ Generation of Thiols from Thioacetates", Tetrahedron Letters, 1999. 40: 1101-1102.

T.-C. Zheng, M. Burkart and D.E. Richardson, "A General and Mild Synthesis of Thioesters and Thiols from Halides", Tetrahedron Letters, 1999. 40: 603-606.

(56) References Cited

OTHER PUBLICATIONS

NJ. Tao, J.A. DeRose and S.M. Lindsay, "Self Assembly of Molecular Superstructures studied by in situ STM: The DNA bases on Au(111)", J. Phys. Chem., 1993. 97: 910-919.

T.A. Early, J. Olmsted and D.R. Kearns, "Base pairing structure in the poly d(G-T) double helix: wobble base-pairs", Nucleic Acid Research, 1978. 5: 1955-1970.

A. Vaught, T. W. Jing and S.M. Lindsay, "Non-exponential tunneling in water near an electrode", Chemical Physics Letters, 1995. 236: 306-310.

B. Xu, X. Xiao and NJ. Tao, "Measurements of Single-Molecule Electromechanical Properties", J. Am. Chem. Soc, 2003. 125: 16164-16165.

S.M. Lindsay, T. Thundat and L.A. Nagahara, "Adsorbate deformation as a contrast mechanism in STM images of biopolymers in an aqueous environment: Images of the unstained, hydrated DNA double helix", J. Microscopy, 1988. 152, Pt 1: 213-220.

H.T. Allawi and J. John Santalucia, "Thermodynamics of internal C<">T mismatches in DNA", Nucleic Acids Research, 1998. 26(11 ): 2694-2701.

Y.-F. Yong, J.F. Kowalski and M.A. Lipton, "Facile and Efficient Guanylation of Amines using Thioureas and Mukaiyama's Reagent, Journal of Organic Chemistry", 1997. 62: 1540-1542.

V.A. Bloomfield, DNA condensation by multivalent cations, Biopolymers, 1998. 44: 269-282.

E. Shapir, H. Cohen, N. Borovok, A.B. Kotlyar and D. Porath, "High-Resolution STM Imaging of Novel Poly{G}- Poly(C) DNA Molecules", J. Phys. Chem B, 2006. 110: 4430-4433.

CR. Clemmer and T.P. Beebe, "Graphite: A mimic for DNA and other Polymers", Science, 1991. 251: 640-642.

CA. Mirkin and M. A. Ratner, "Molecular Electronics", Annu. Rev. Phys. Chem., 1992. 43: 7389-7396.

A. Aviram and M.A. Ratner, eds. "Molecular Electronics: Science and Technology (Annals of the New York Academy of Sciences)." vol. 852. 1998, New York Academy of Sciences, NY.

G. Fagas and K. Richter, in "Introducing Molecular Electronics", ed .. 2005, Berlin: 107.

S.M. Lindsay and M.A. Ratner, "Molecular Transport Junctions: Clearing Mists," Advanced Materials, 2007. 19: 23-31.

J. Park, A.N. Pasupathy, J.I. Goldsmith, C. Chang, Y. Yaish, J.R. Petta, M. Rinkoski, J.P. Sethna, H.D. Abruna, P.L. McEuen and D.C. Ralph, "Coulomb Blockade and the Kondo Effect in single atom transistors", Nature, 2002. 417:722-725.

W. Liang, M.P. Shores, M. Bockrath, J.R. Long and H. Park, "Kondo Resonance in a single molecule transistor", Nature, 2002. 417: 725-728.

L.H. Yu and D. Natelson, "Transport in single-molecule transistors: Kondo physics and negative differential resistance", Los Alamos National Laboratory, Preprint Archive, Condensed Matter, 2004: 1-15, arXiv: cond-mat/0405568.

D. Natelson, in. Single-Molecule Transistors in press ed, ed. N.S. Nalwa. Vol. Handbook of Organic Electronics and Photonics. 2006: American Scientific Publishers.

A. A. Houck, J. Labaziewicz, E.K. Chan, J. A. Folk and L. Chuang, "Kondo effect in electromigrated gold break junctions", Nano Lett., 2005. 5: 1685-1688.

M.D. Fischbein and M. Drndic, "Nanogaps by direct lithography for high-resolution imaging and electronic characterization of nanostructures", App. Phy. Lett., 2006. 88: 063116.

CZ. Li and NJ. Tao, "Quantum transport in metallic nanowires fabricated by electrochemical deposition/dissolution", Applied Physics Letters, 1998. 72: 894-896.

J.G. Simmons, "Generalized formula for the electric tunnel effect between similar electrodes separated by a thin insulating film", J. Appl. Phys., 1963. 34(6): 1793-1803.

J. Sanchez-Quesada, A. Saghatelian, S. Cheley, H. Bayley, M.R. Ghadiri and M. Reza, "Single DNA Rotaxanes of a transmembrane pore", Angew. Chem. Int. Ed., 2004. 43: 3063-3067.

H.B. Gamper, K. Arar, A. Gewirtz and Y.M. Hou, "Unrestricted Hybridization of Oligonucleotides to Structure-Free DNA", Biochemistry, 2006. 45: 6978-6986.

X.C. Zhao, CM. Payne, P.T. Cummings and J. W. Lee, "Single-strand DNA molecule translocation through nanoelectrode gaps", Nanotechnology, 2007. 18(42).

A. Aksimentiev, J.B. Heng, G. Timp and K. Schulten, "Microscopic kinetics of DNA translocation through synthetic nanopores", Biophysical Journal, 2004. 87(3): 2086-2097.

J. Jeon and M.S. Chun, "Structure of flexible and semiflexible polyelectrolyte chains in confined spaces of slit micro/ nanochannels", Journal of Chemical Physics, 2007. 126(15).

W.D. Cornell, P. Cieplak, C.I. Bayly, LR. Gould, K.M. Merz, D.M. Ferguson, D.C. Spellmeyer, T. Fox, J. W. Caldwell and P.A. Kollman, "A second generation force field for the simulation of proteins, nucleic acids, and organic molecules", Journal of the American Chemical Society, vol. 117, No. 19, 1995, pp. 5179-5197.

D.L. Ermak and J. A. Mc Cammon, "Brownian Dynamics with Hydrodynamic Interactions", Journal of Chemical Physics, 1978. 69(4): 1352-1360. 178.

R.S. Graham and R.G. Larson, "Coarse-grained brownian dynamics simulations of electrophoresis of DNA molecules from generalized reptation models", Macromolecules, 2007. 40(2): 366-378.

M. Muthukumar, "Mechanism of DNA transport through pores", Annual Review of Biophysics and Biomolecular Structure, 2007. 36: 435-450.

CR. Cantor, P.R. Schimmel, Biophysical Chemistry (W.H. Freeman, San Francisco, 1980).

V. Mujica, M. Kemp, M.A. Ratner, J. Chem. Phys. 101, 6849 (1994).

R. Landauer, J. Phys. Condens. Matter 1 , 8099 (1989).

Y. Imry, R. Landauer, Revs. Mod. Phys. 71 , S306 (1999).

A. M. Kuznetsov, J. Ulstrup, Electron transfer in chemistry and biology (Wiley, New York, 1999).

G. A. Jeffrey, W. Saenger, Hydrogen bonding in biological structures (Springer, Berlin, 1991).

P. de-las-Santos-Alvarez, M. J. Lobo-Castan[omicron]n, A. J. Miranda-Ordieres, P. Tufi[omicron]n- Blanco, Anal Bioanal Chem 378, 104-118 (2004).

K. A. Schug, W. Lindner, Chem. Rev. 105, 67 (2005).

C. A. McDermott, M. T. McDermott, J. B. Green, M. D. Porter, J. Phys. Chem. 99, 13257 (1995).

H. Tanaka, C. Hamai, T. Kanno, T. Kawai, Surface Science 423, L611 (1999).

Nilsson, J., Lee, J. R. I., Ratto, T. V. and Letant, S. E. (2006), "Localized Functionalization of Single Nanopores." Adv. Mater., 18: 427-431. doi:10.1002/adma.200501991.

Takashi Ito, et al. "Observation of DNA transport through a single carbon nanotube channel using fluorescence microscopy", Chemical Communications, 2003, pp. 1482-1483.

Rong Fan, et al., "Nano Letters", "DNA Translocation in Inorganic Nanotubes", Sep. 2005, pp. 1633-1637.

Jin He, et al. "Identification of DNA Basepairing via Tunnel-Current Decay", Nano Letters 7(12)(2007), 3854-3858.

Muenier, et al. "Enhancement of the transverse conductance in DNA nucleotides. "The Journal of Chemical Physics, published online Jan. 29, 2008, 128: 1-4, Fig. 1; p. 1, col. 2, para 2; p. 2, para 1.

He et al. "Functionalized Nanopore-Embedded Electrodes for Rapid DNA Sequencing," The Journal of Physical Chemistry C Letters 2008, 112, 3456-3459 (published on Web Feb. 14, 2008).

International Search Report and Written Opinion, dated Nov. 2, 2009, for International Application No. PCT/US2009/037563.

Loakes et al., "5-Nitroindole as a universal base analogue," Nucleic Acids Research, 1994, vol. 22, No. 20. pp. 4039-4043.

Fox, K.R. and T. Brown. An extra dimension in nucleic acid sequence recognition. Quarterly Reviews of Biophysics, 2005, 38, pp. 311-320.

Nishino T. et al. "Carbon Nanotube Scanning Tunneling Microscopy Tips for Chemically Selective Imaging", Analytical Chemistry, American Chemical Society, US, vol. 74, No. 16, Aug. 15, 2002, pp. 4275-4278.

(56) References Cited

OTHER PUBLICATIONS

Akeson et al. "Microsecond Time-Scale Discrimination Among Polycytidylic Acid, Polyadenylic Acid, and Polyuridylic Acid as Homopolymers or as Segments Within Single RNA Molecules." Biophys. J. 77.6(1999): 3227-3233.
Aksimentiev et al. "Microscopic Kinetics of DNA Translocation through Synthetic Nanopores." Biophys. J. 87.3(2004): 2086-2097.
Ashkenasy et al. "Recognizing a Single Base in an Individual DNA Strand: A Step Toward DNA Sequencing in Nanopores." Angew. Chem. Int. Ed. Engl. 44.9(2005): 1401-1404.
Branton et al. "The Potential and Challenges of Nanopore Sequencing." Nat. Biotechnol. 26.10(2008): 1146-1153.
Cui et al. "Reproducible Measurement of Single-Molecule Conductivity." Science. 294.5542(2001): 571-574.
Lagerqvist et al. "Influence of the Environment and Probes on Rapid DNA Sequencing via Transverse Electronic Transport." Biophys. J. 93.7(2007): 2384-2390.
Meller et al. "Rapid Nanopore Discrimination Between Single Polynucleotide Molecules." PNAS.97.3(2000): 1079-1084.
Meller et al. "Voltage-Driven DNA Translocations Through a Nanopore." Phys. Rev. Lett. 86.15(2001): 3435-3438.
Muthukumar et al. "Simulation of Polymer Translocation Through Protein Channels." PNAS. 103.14(2006): 5273-5278.
Tomfohr et al. "Theoretical Analysis of Electron Transport Through Organic Molecules." J. Chem. Phys. 120.3(2004): 1542-1554.
Zikic et al. "Characterization of the Tunneling Conductance Across DNA Bases." Phys. Rev. E. Stat. Nonlin. Soft Matter Phys. 74.1(2006): 011919.
Zwolak et al. "Colloquium: Physical Approaches to DNA Sequencing and Detection." Rev. Mod. Physics. 80.1(2008): 141-165.
Zwolak et al. "Electronic Signature of DNA Nucleotides via Transverse Transport." Nano Lett. 5.3(2005): 421-424.
John W. Lawson, et al. "Transport in Molecular Junctions with different molecular contacts," Physical Review B74, 125401 (2006).
Mohammad, MM et al. "Controlling a Single Protein in a Nanopore through Electrostatic Traps" Journal of the American Chemical Society 2008, vol. 130, No. 12; pp. 4081-4088; abstract; figure 1; p. 4082, paragraph 2; p. 4083, paragraphs 5-7; p. 4087, paragraph 5.
Chen et al., (2007). "Subfemtomole level protein sequencing by Edman degradation carried out in a microfluidic chip." Chem. Commun. 24: 2488-2490.
Yan-Fei et al., (2007). "Development of C-Terminal Sequencing Analysis Protein and Peptide." Chin. J. Anal. Chem. 35: 1820-1826.
Bandeira et al., (2008). "Beyond Edman Degradation: Automated de novo protein sequencing of monoclonal antibodies." Nature Biotechnology 26: 1336-1338.
Sutherland et al., (2004). "Structure of Peptides Investigated by Nanopore Analysis." Nano Letters 4(7): 1273-1277.
Stefureac et al., (2006). "Transport of α-Helical Peptides through α-Hemolysin and Aerolysin Pores." Biochemistry 45(30): 9172-9179.
Kang et al., (2006). "Stochastic Detection of Enantiomers." J. Am. Chem. Soc. 128, 10684-10685.
Astier et al., (2006). "Toward Single Molecule DNA Sequencing: Direct Identification of Ribonucleoside and Deoxyribonucleoside 5'-Monophosphates by Using an Engineered Protein Nanopore Equipped with a Molecular Adapter." J. Am. Chem. Soc. 128: 1705-1710.
Mohammad et al. "Controlling a Single Protein in a Nanopore through Electrostatic Traps" J. Am. Chem. Soc. 2008, 130, 4081-4088; abstract, Fig. 1 B, p. 4083, col. 1, para 2-3.
International Search Report and Written Opinion, dated May 29, 2015, for International Application No. PCT/US2015/017519.
E. S. Lander et al., Initial sequencing and analysis of the human genome, Nature, 2001. 409,: 860-921.
AJ. Sharp, Z.C. Cheng and E.E. Eichler, Structural variation of the human genome, Annu. Rev. Genomic Hum. Genet., 2006. ARI: 407-442.
B.E. Stranger, M.S. Forrest, M. Dunning, CE. Ingle, C. Beazley, N. Thorne, R. Redon, CP. Bird, A. de Grassi, C Lee, C Tyler-Smith, N. Carter, S.W. Scherer, S. Tavare, P. Deloukas, M.E. Hurles and E.T. Dermitzakis, Relative Impact of Nucleotide and Copy Number Variation on Gene Expression Phenotypes, Science, 2007. 315: 848-853.
M. Margulies, M. Egholm, W.E. Airman, S. Attiya, J.I.S. Bader and L.A. Bemben, Genome sequencing in microfabricated high-density picolitre reactors, Nature, 2005. 437: 376-380.
I. Braslaysky, B. Herbert, E. Kartalov and S.R. Quake, Sequence information can be obtained from single DNA molecules, Proc. Natl. Acad. Sci. (USA), 2003. 100: 3960-3964.
P. Williams, M.A. Hayes, S.D. Rose, L.B. Bloom, LJ. Reha-Krantz and V.B. Pizziconi USA U.S. Pat. No. 7,037,687 May 2.
G. Spencer, NHGRI News Release, Oct. 4, 2006.
S. M. Lindsay, T. Thundat, L.A. Nagahara, U. Knipping and R.L. Rill, Images of the DNA double helix in water, Science, 1989. 244: 1063-1064.
T. Jing, A.M. Jeffrey, J.A. DeRose, YX. Lyubchenko, L.S. Shlyakhtenko, R.E. Harrington, E. Appella, J. Larsen, A. Vaught, D. Rekesh, F.X. Lu and S.M. Lindsay, Structure of hydrated oligonucleotides studied by in-situ scanning tunneling microscopy, Proc. Natl. Acad. Sci. (USA), 1993. 90: 8934-8938.
A.M. Jeffrey, T. W. Jing, J.A. DeRose, A. Vaught, D. Rekesh, F.X. Lu and S.M. Lindsay, Identification of DNA-cisplatin adducts in a blind trial of in-situ scanning tunneling microscopy., Nucleic Acids Research, 1993. 21: 5896-5900.
D. Lampner, PhD Thesis in Physics, Arizona State University, (1995).
T. Ohshiro and Y. Umezawa, Complementary base-pair-facilitated electron tunneling for electrically pinpointing complementary nucleobases, Proc. Nat. Acad. Sci., 2006. 103: 10-14.
JJ. Kasianowicz, E. Brandin, D. Branton and D. W. Deamer, Characterization of individual polynucleotide molecules using a membrane channel, Proc. Nat. Acad. Sci., 1996. 93: 13770 13773.
A. Meller, L. Nivon, E. Brandin, J. Golovchenko and D. Branton, Rapid nanopore discrimination between single polynucleotide molecules, Proc. Natl. Acad. Sci. (USA), 2000. 97: 1079-1084.
J.B. Heng, V. Dimitrov, Y. V. Grinkova, C Ho, T. Kim, D. Muller, S. Sligar, T. Sorsch, R. Twesten, R. Timp and G. Timp. The detection of DNA using a silicon nanopore. in Electron Devices Meeting, 2003. IEDM '03 Technical Digest. 2003: IEEE International.
D.W. Deamer and D. Branton, Characterization of nucleic acids by nanopore analysis, Acc. Chem. Res, 2002, 35:817-825.
J.B. Heng, A. Aksimentiev, C. Ho, P. Marks, Y.V. Grinkova, S. Sligar, K. Schulten and G. Timp, The electromechanics of DNA in a ysnthetic nanopore, Biophysical Journal, 2006, 90(3): 1098-1106.
Timp, The electromechanics of DNA in a ysnthetic nanopore, Biophysical Journal, 2006, 90(3): 1098-1106.

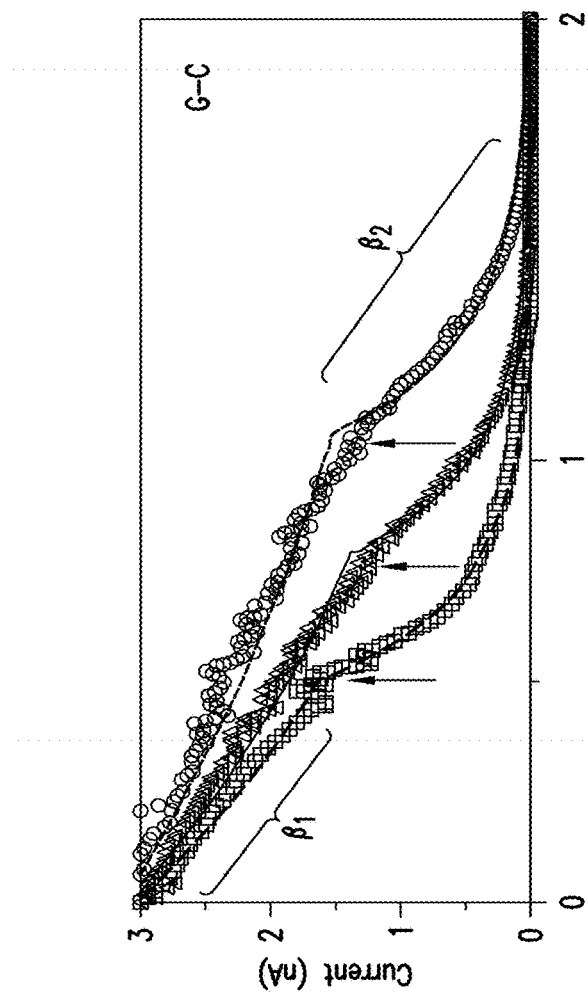
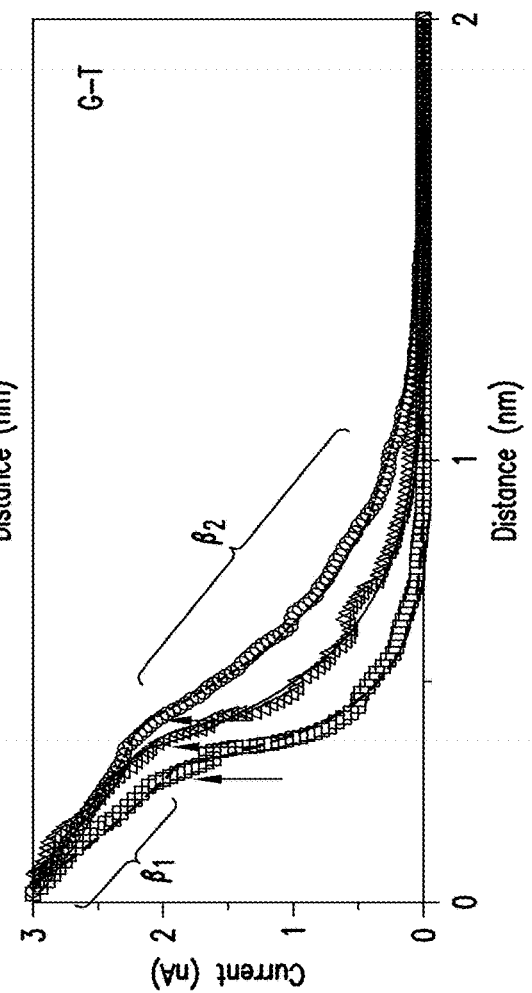
FIG. 7A
FIG. 7B

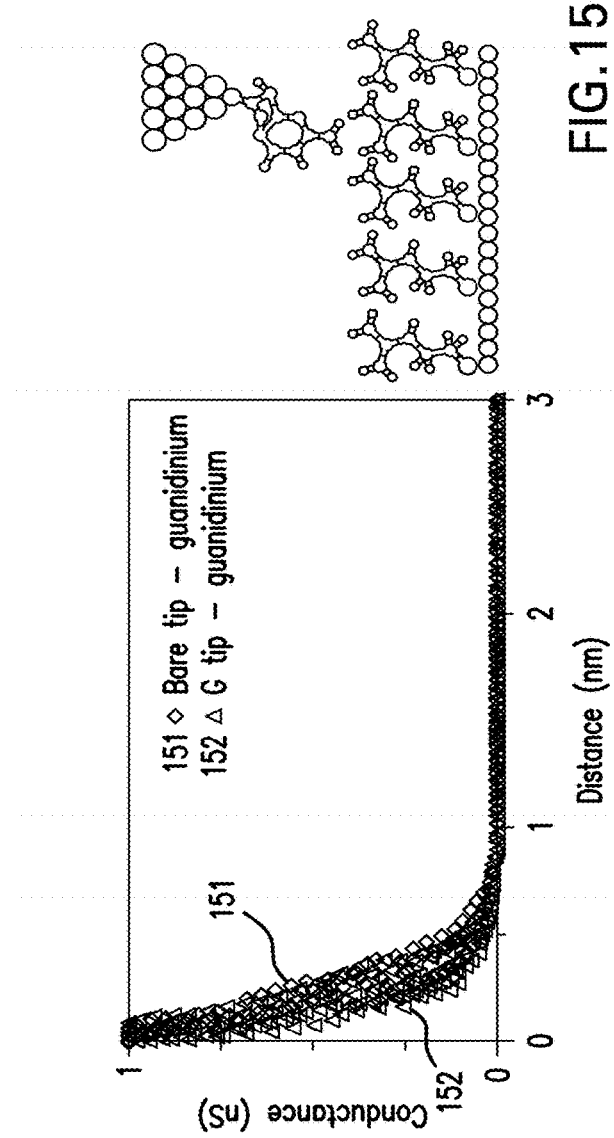
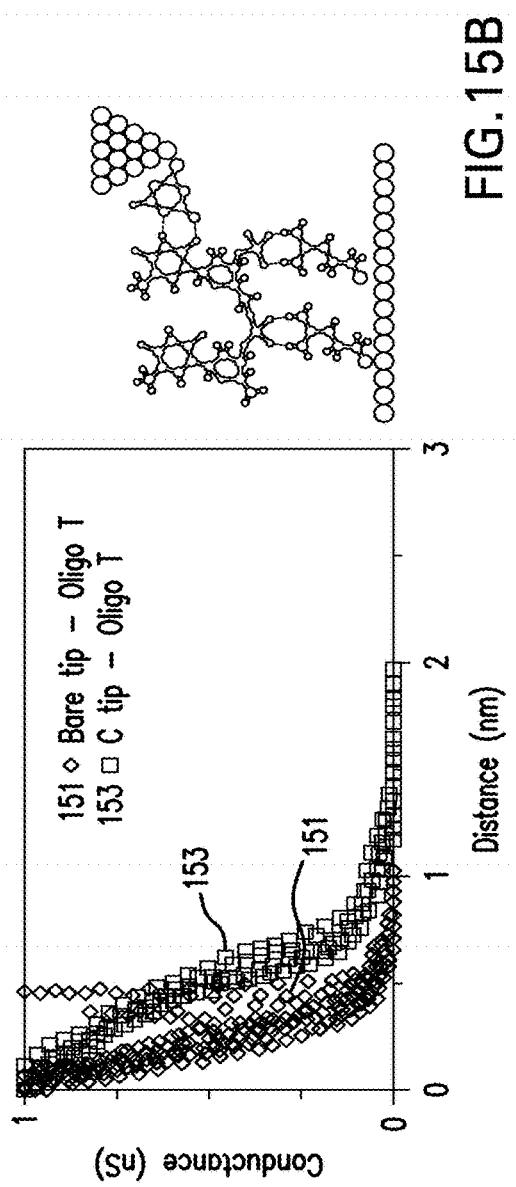

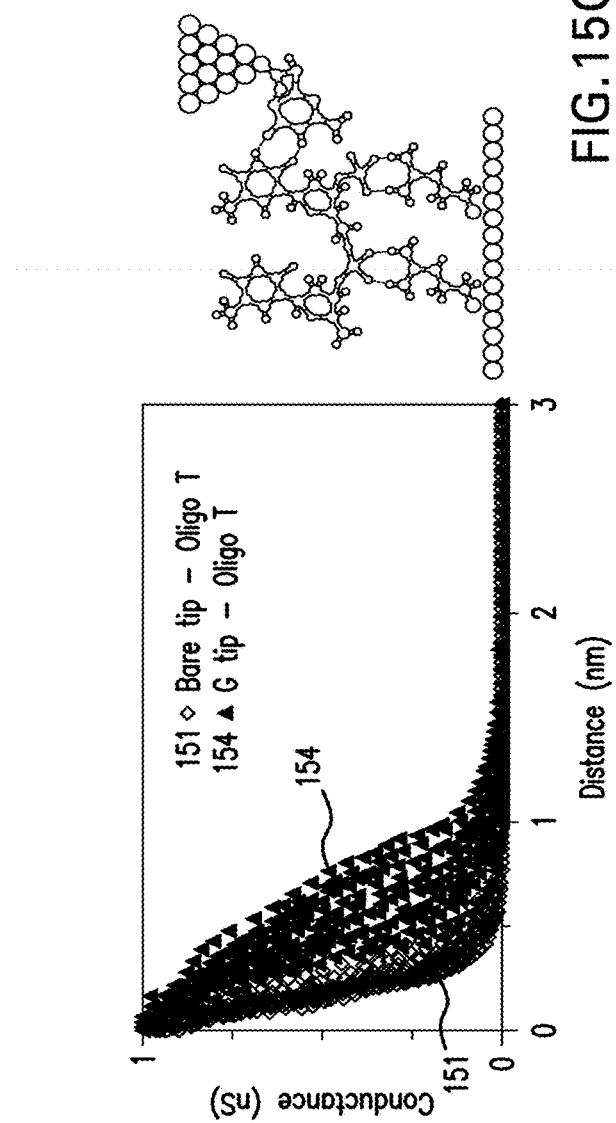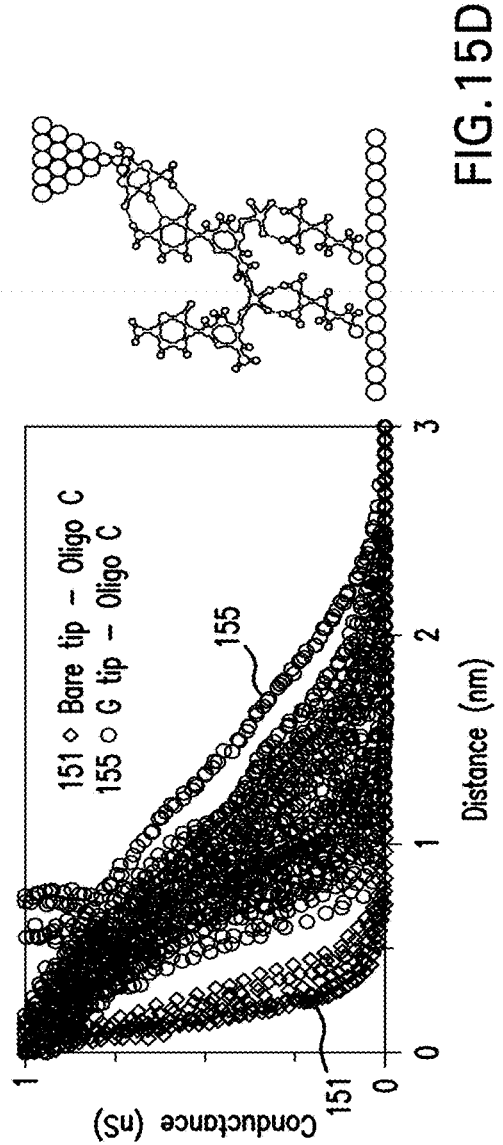

View into trench

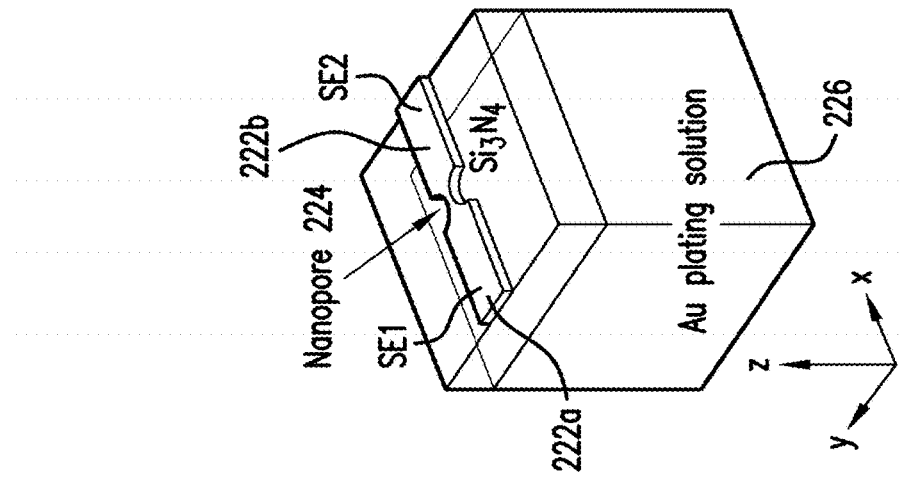
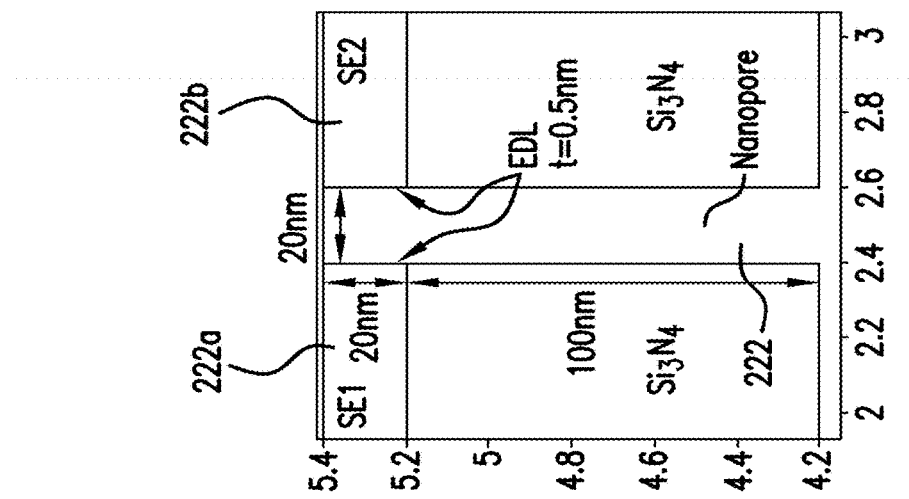
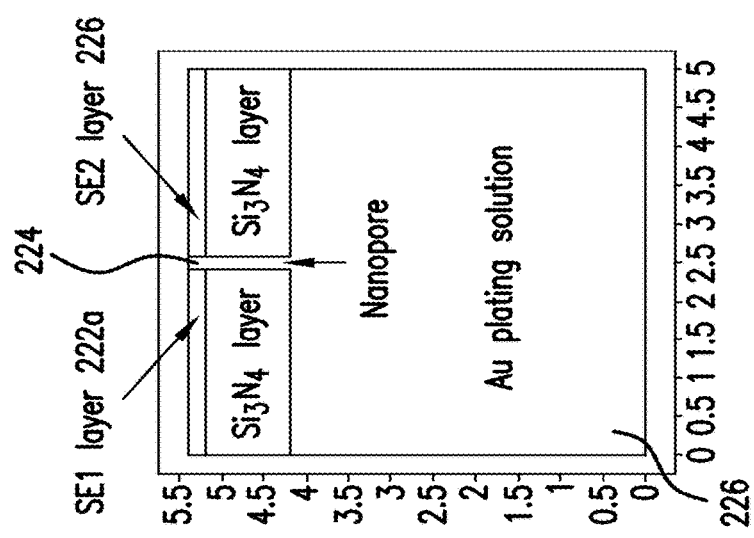
FIG. 22C
FIG. 22B
FIG. 22A

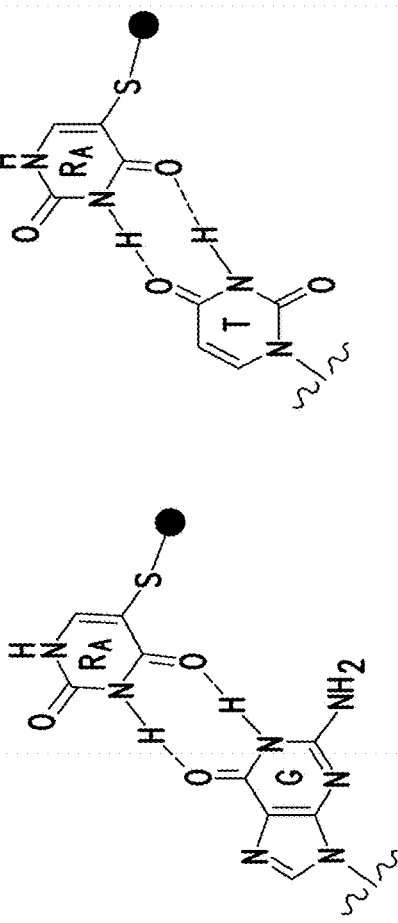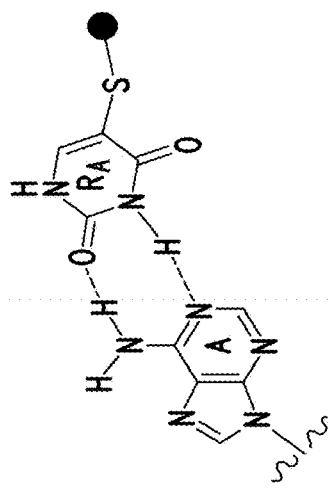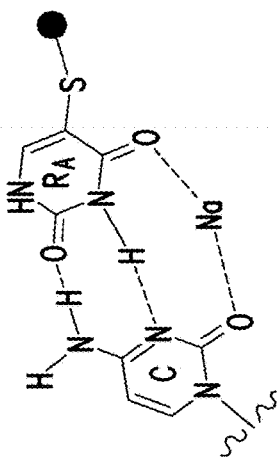
FIG. 24

Thymine Reader: 2,6-amino-8-mercaptopurine($R_T$)
The Watson-Crick base pair
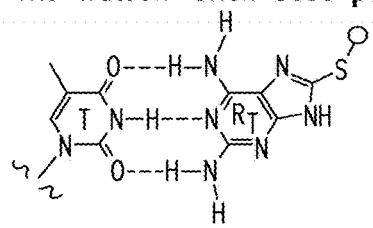
Mismatched base pairs
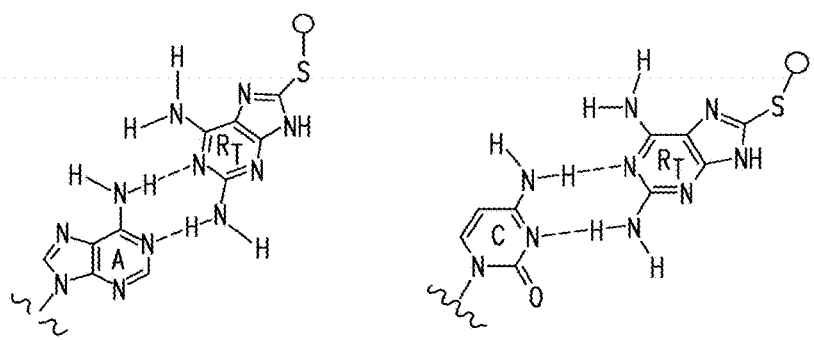
Analogues of 2-diaminoadenine
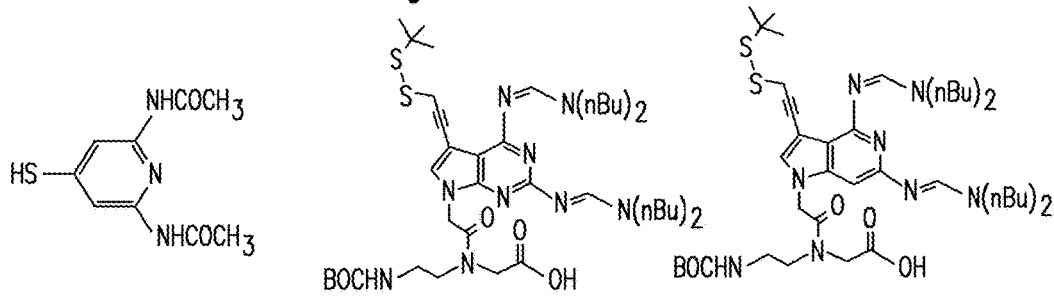
2,6-diacetamido-4-mercaptopyridine
7-deaza-2-aminoadenine PNA monomer
3,7-dideaza-2-aminoadenine PNA monomer
FIG.30

| Structure | $\beta_{max}$ (Å$^{-1}$) | L(Å) | G |
|---|---|---|---|
| 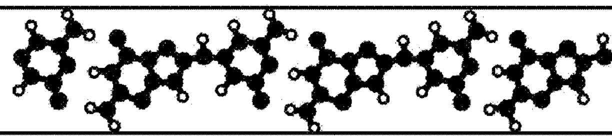 | 0.70 | 12.8 | 9.8 nS |
| 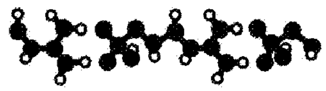 | 1.63 | 9.9 | 8.4 pS |
| 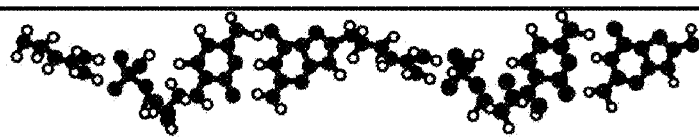 | 1.16 (1.03) | 24 | 0.056 fS (1.32 fS) |

FIG. 42

DEVICES AND METHODS FOR TARGET MOLECULE CHARACTERIZATION

CROSS-REFERENCE TO RELATED APPLICATIONS

The present application is a continuation of U.S. Utility application Ser. No. 12/594,366 filed Oct. 2, 2009, which is a national stage filing of PCT Application No. PCT/US2008/059602 filed Apr. 7, 2008, and claims priority to U.S. Provisional Application Nos. 60/922,288 filed Apr. 6, 2007, 60/989,089 filed Nov. 19, 2007 and 61/022,155 filed Jan. 18, 2008. The contents of each of these provisional applications is incorporated by reference in their entirety.

STATEMENT REGARDING FEDERALLY SPONSORED RESEARCH & DEVELOPMENT

This invention was made with government support under NHGRI Grant Nos. 1R21 HG3061, 1R21 HG004378-01 and GM 21966, awarded by the National Institute of Health. The government has certain rights in this invention.

FIELD OF THE INVENTION

The present invention is directed to systems, devices and methods for identifying biopolymers, such as strands of DNA, as they pass through a constriction, such as a nanopore. More particularly, the invention is directed to such systems, devices and methods in which the constriction is provided with a functionalized unit which, together with a newly translocated portion of the biopolymer, forms a temporary electrical circuit that can be used to characterize that portion of the biopolymer.

BACKGROUND OF THE INVENTION

One goal in the DNA sequencing industry is to reduce the cost and increase the speed for sequencing an individual's genome. A target accuracy of 99.99%[1] is also important. Another vital goal is long contiguous reads. Array technology is revealing a remarkable long range complexity in the genome, some of which is summarized in Table 1 below, taken from the review by Sharp et al.[2]. This complexity is difficult to retrieve through the assembly of contigs much shorter than the size ranges referred to in the table. Copy number variations are particularly vexing, yet they have important phenotypes owing to gene-dose variations. These clinically-important copy number variations are almost completely uncorrelated with the SNPs extracted by conventional re-sequencing.[3]

TABLE 1

| Long-range structures in the genome (from Sharpe et al. Ann. Rev. Hum. Gen. 17 407 2006) | | |
|---|---|---|
| Variation | Rearrangement type | Size range[a] |
| Single base-pair changes | Single nucleotide polymorphisms, point mutations | 1 bp |
| Small insertions/deletions | Binary insertion/deletion events of short sequences (majority < 10 bp in size) | 1-50 bp |
| Short tandem repeats | Microsatellites and other simple repeats | 1-500 bp |
| Fine-scale structural variation | Deletions, duplications, tandem repeats, inversions | 50 bp to 5 kb |
| Retroelement insertions | SINEs, LINEs, LTRs, ERVs[b] | 300 bp to 10 kb |
| Intermediate-scale structural variation | Deletions duplications, tandem repeats, inversions | 5 kb to 50 kb |
| Large-scale structural variation | Deletions, duplications, large tandem repeats, inversions | 50 kb to 5 Mb |
| Chromosomal variation | Euchromatic variants, large cytogenetically visible deletions, duplications, translocations, inversions, aneuploidy | ~5 Mb to entire chromosomes |

Sequencing by extension relies on detection of a signal owing to nucleotide addition by a polymerase and instruments using many molecules in picoliter wells are already in commercial use.[4] For example, the 454 Life Sciences instrument exploits energetic pyrophosphates to give label-tree optical signals, but the length of the read is limited by the dephasing problem as individual clones in a well fall behind owing to errors in nucleotide addition. Single molecule measurements present a way around this problem[5,6] and this is the basis of the Helicos system. However, the chemistry required to do this is for from trivial and the use of non-natural nucleotides limits the length of the extensions. An interesting variant is the proposal to sequence by ligation (Xiaohua lab, UCSD[7]).

The use of the scanning tunneling microscope (STM) for sequencing DNA (AFM and STM in novel approaches to sequencing) has been studied in the past. DNA has been imaged at high resolution in water[8-10] but sequencing was not possible. In part, this is because the magnitude of the tunneling current through DNA in terms of base composition has not been easy to interpret. In addition, the STM images themselves are not amenable to ready interpretation. These images often reflect where the structure makes contact with the underlying metal and not the real high points of the molecule.[11] This complication may also affect the recent STM imaging work of Oshiro and Umezawa.[12] this difficulty rules out sequencing by imaging.

The nanopore approach[13-25] has the great advantage of only allowing one base to pass a particular point at a time (if the orifice is small enough). It can also be highly precessive (moving from one base to the next without "stuttering") if the driving force is high enough. For instance, if one were to assume that an allowable limit on stuttering misreads of 1 part in $10^4$ (99.99% accuracy), this would require a driving free-energy of 9.3 $k_BT$. To achieve this requires either a voltage drop across a base of 0.23V (a field of $4 \times 10^8$ V/m) or a force of 55 pN (where a base-to-base separation of 0.6 nm for stretched DNA was used[26]). These conditions are readily achieved and demonstrable.

Since Kasianowicz[13] employed a biological nanopore, the alpha-hemolysin ion channel as a sensor to characterize DNA, nanopore based biosensors have attracted much attention.[21,27,28] However, biological nanopores have several shortcomings as they are unstable, fragile and fixed in size. Synthetic single nanopores[29-33] were developed as alternatives to biological nanopores. These artificial single nanopores have been successfully used to characterize DNA translocation, folding, and conformational changes,[34-37] the effects of high pH,[38] low temperatures,[39] multiple DNA lengths,[40] the effects of electric field strength,[41] the effects of surface modification by atomic layer deposition (ALD)[42] and also for mimicking ion channel activity.[43] Solid-state single nanopores now have a real track record. They have the following advantages: (1) the pore size is comparable to that of a single molecule; (2) the pore size is tunable to fit a wide range of molecules; and (3) robust single channels between cis and trans reservoirs are readily achieved. They also have the following strengths as a manufacturable device; (1) they are chemically and thermally stable; (2) their surfaces are readily modified; (3) they are mechanically robust; and (4) they are readily incorporated into integrated circuit (IC) technology.

It was hoped originally that the DNA bases could be identified directly via distinctive variations in the ionic current through the nanopore as each base occluded the pore on transit of the smallest part of the pore. However, the ionic current signal has proved difficult to interpret. As a result, several new schemes have been proposed. One method relies on electronic measurement of tunnel current as the DNA bases pass through a tiny gap between a pair of electrodes[44-46] though there is some debate about the feasibility of this approach.[47] Another proposes to exploit the distinctive dipoles of the bases with measurement of dielectric response on the molecular scale.[48] Yet another proposes to measure the optical response as dye-labeled complimentary strands are "peeled off" the main template strand by passage through the nanopore.[49] A group associated with the present inventors has focused on measuring the force associated with translocation.[50] At the time of writing, there are no published reports of a signal with single-base resolution.[49]

FIG. 2 shows the layout of a proposed sequence reader that relies on differences in the tunnel-transport of electrons through bases (taken from a recent review by Zwolak and Di Ventre[49]). To understand the obstacles laying in the way of operating a reader such as this one, it is useful to take a look at the history of single molecule electronic measurements. When it comes to the conductance of a molecule placed between metal electrodes, published experimental data are all over the map[51] and DNA is a wonderful illustration of the problem. DNA has been reported to be an insulator,[52] semiconductor,[53] conductor[54] and even superconductor[55] (though the issue is now probably resolved[56]). With the exception of one datum[52] these results are for conduction along the strand, but the problems inherent in making these measurements are the same no matter what the geometry is. Some of these problems include:

(1) Tunnel transport is exponentially sensitive to the atomic arrangement of atoms in the tunneling path and even a bond rotation can change transport by a significant amount[57, 58]

(2) Outside of ultrahigh vacuum, metal surfaces are covered with (unknown amounts of) adventitious contamination leading to dramatic variations in contact.[59]

(3) Base sequence, fluctuations of structure, and very importantly, counter ions, can dominate the electronic properties of a polyelectrolyte like DNA.[60]

FIG. 3 shows an experimental arrangement that captures some of the elements that would be required for any electronic sequencing of DNA. The experimental arrangement permits reproducible determination of single molecule conductance, albeit practicing the art on a rather simple octanedithiol molecule.[61] The target molecule was chemically-contacted (to a planar bottom electrode and a nanoparticle top electrode) using gold-thiol chemistry to form a metal-chemical bond-molecule-chemical bond-metal sandwich. The resulting reproducible data showed, very clearly, the effects of having different numbers of molecules in the gap. The experiment works because the tip is not well-connected to the surrounding monolayer of octane monothiols, at best touching the terminal methyl groups, but most likely interacting via a layer of contaminant molecules. But the contamination is displaced by the chemical bonding in the case of the desired thiolated top-contact. FIG. 3A shows a single dithiolated octane molecule 31 inserted into a defect in a monolayer 32 of octane-monothiol molecules on a gold electrode 33 and a gold nanoparticle 34 is chemically attached as a top electrode. A metal-coated APM probe 35 makes contact with the nanoparticle 34 to complete the circuit. As seen in FIG. 3B, different contacts produce different current-voltage curves 36a-c, but these are all integral multiples of each other, interpreted as integer numbers of molecules (1, 2, 3 . . . ) in the gap. FIG. 3C shows the superposition 37 that occurs when each curve is divided at all points by the appropriate integer. FIG. 3D shows the effective multiplier for thousand of curves—over 1000 contacts fell in the 'single molecule' bin.

FIG. 4 shows that the conductance through the desired path 44 is over a thousand times higher than the conductance through the non-bonded path 46. The conductance measured for a single molecule was quite close to what was predicted by a first principles theory 42 with no adjustable parameters[61] (and the remaining small discrepancy is now explained[62]). This is to be contrasted with a "best case" agreement of a factor of 500 achieved in previous reports of single molecule electronic properties.[51] Chemical bonds, in and of themselves, only enhance tunnel current by a few times.[63] The most important factor is probably the role that bonding plays in displacing contamination from the tunnel junction, as metal surfaces are invariably coated with hydrocarbons outside of an ultra-clean, ultrahigh vacuum environment.[59] Subsequent to the above-described experimental arrangements for measurement of single molecule conductance, a variety of measurements and techniques have evolved.[34,51,57,58,61,64-82 83-86] In addition, there have been very significant contributions to the methods from the Tao group[77] and the Columbia group.[87,88] Many issues remain to be resolved, and it is important to point out that, even with the best current methods, different atomic arrangements of the contact at the electrode can lead to differences in the measured conductance.[85,86,89]

Hydrogen-bond mediated STM image-enhancement has been reported.[12] In addition, it is now known that one may directly measure hydrogen bond enhanced tunneling. Therefore, one area of study is to build an electrical readout system that incorporates a pair of electrodes in a nanopore. Nanopores with electrical contacts are being constructed by several groups pursuing sequencing by tunneling[44-46] or capacitance measurement.[48] An electrical readout would be difficult with biomolecular nanopores[13] and almost certainly requires the use of a solid state nanopore. Registration of a pair of electrodes with a small (about 2-3 nm diameter) nanopore is not an easy task. Little material exists in the literature, but the two leading groups working in this area are the Harvard Nanopore Sequencing Group, where Golovchenko leads an effort towards solid state nanopore sequencing[29] and Timp's group at UIUC, which is pursuing dielectric nanopore sequencing.[48] The Harvard group is using a carbon nanotube placed across the nanopore that is judiciously cut so that a nm-scale gap in the electrodes lies just above the pore. The Timp group is working to build a layered semiconductor capacitor, with conductive elements separated by a sub-nm insulating spacer.[48,49] The DNA would pass through a nanopore drilled perpendicular to these layers. However, sequencing of translocating DNA through such pores has proven to be elusive.

SUMMARY

In one aspect, the present invention is directed to a readout device and scheme for DNA sequencing through a constriction, such as a nanopore. The scheme utilizes the electron tunneling current mediated by specific hydrogen-bonding molecular recognition events.

In another aspect, the present invention is directed to the design and construction of a manufacturable instrument, constructed so as to allow for parallel operation of many constrictions for performing sequencing, such as of ssDNA or dsDNA.

The system employs at least one device having at least two sensing electrodes spaced apart by a gap and positions on either side of a constriction, such as a nanopore. The nanopore electrode gap construction may be achieved by electrochemical assembly to produce gaps that are reform able in-situ. Alignment of a nanogap sensing electrode pair with a constriction is achieved by means of novel 'though-pore' plating process. Thereafter, active gap control may be used to dynamically-control the gap. Since the natural DNA bases frequently form mismatched basepairs, custom recognition elements (referred to herein as "affinity elements") are used for molecular recognition. Each constriction is functionalized with at least one such custom affinity element. Electrophoresis, magnetic bead technology and the signal from the pore itself can be used to effect translocation through the constriction and characterization of the molecule. The system is thus configured to acquire data related to the locations of specific bases in a single strand of DNA.

In the device, a pair of spaced apart sensing electrodes border the constriction. The first sensing electrode is connected to a first affinity element (e.g., a phosphate grabber when the target molecule is ssDNA) while the second sensing electrode is connected to a second affinity element. Each affinity element may be connected to its corresponding electrode via one or more intermediary compounds, such as a linker molecule, which itself typically is connected to the electrode via an electrode attachment molecule, such as a thiol. The first and second affinity elements are configured to temporarily form hydrogen bonds with first and second portions of the molecule as the latter passes through the constriction. During translocation, the electrodes, affinity elements and first and second portions of the target molecule complete an electrical circuit and allow a measurable electrical current to pass between the first and second electrodes. The time-varying nature of this electrical current and the specific affinity elements employed, allow one to characterize the first and second portions of the target molecule.

The present invention's approach to nanopore electrode construction is directed to mimicking the scanning tunneling microscopy that has proved effective and successful in experiments with hydrogen-bond-based electronic recognition. Three elements of this are: 1) self-aligned metal-gap-metal junctions capable of being reformed in-situ; 2) active control of the tunnel gap; and 3) manufacturability. The metal used in these junctions can be gold. Trials with gold electrodes have indicated that the "blinking" of contacts made to soft metals is not a significant problem.[71]

BRIEF DESCRIPTION OF THE DRAWINGS

For a better understanding of the present invention and to show how the same may be carried out in practice, reference will now be made to the accompanying drawings, in which:

(FIG. 3A) Arrangement for contacting single molecules. A single dithiolated octane molecule is (spontaneously) inserted into a defect in a monolayer of octane-monothiol molecules on a gold electrode and a gold nanoparticle is chemically attached as a top electrode. A metal-coated AFM probe makes contact with the nanoparticle to complete the circuit. (FIG. 3B) Different contacts produce different current-voltage curves, but these are all integral multiples of each other, interpreted as integer numbers of molecules (1, 2, 3 . . . ) in the gap. (FIG. 3C) shows the superposition that occurs when each curve is divided at all points by the appropriate integer. (FIG. 3D) shows the effective multiplier for thousand of curves—over 1000 contacts fell in the 'single molecule' bin.

FIG. 6A shows raw current vs. distance data for a bare Au tip (green), thiophenol (Tp)-modified tip (orange) and G-modified tip (black) on bare gold. FIG. 6C shows this on a thymidine SAM and FIG. 6D shows this on a deoxycytidine SAM. FIG. 6B shows data taken with a C-functionalized probe on a thymidine SAM (blue lines, green lines are data for the bare probe). Initial conditions are i=3 nA, V=0.5V, retraction speed=133 nm/s. Data were taken in trichlorobenzene.

FIGS. 7A-7B. Some typical curves for a G probe and a deoxycytidine surface (a) or a thymidine surface (b) showing fits to equations 1a and 1b. Arrows point to the transition between the slow decay ($\beta_1$) and the rapid decay ($\beta_1$) regions at a distance $z_c$.

FIGS. 8D-8G show histograms of the charge transferred in each retraction (all data are used here) for (8D) bare gold, (8E) a deoxycytidine SAM, (8F) a thymidine SAM and (8G) a SAM made with an equimolar mix of C and T. Black bars are for an 8-mereaptoguanine functionalized tip, orange bars are for a thiophenol functionalized tip and green bars are for a bare tip. The green shaded block indicates the region of unambiguous signals for G-C basepairs.

FIG. 11A shows monolayer-covered gold single-atom steps. FIG. 11B shows a zoom-in showing the pits (some marked by arrows) that form owing to the thiol-driven reconstruction of the Au surface. FIG. 11C shows molecular resolution (some pits marked by arrows). FIGS. 11A-11C were taken in tris-HCl. As seen in FIG. 11D, addition of phosphate causes the surface to reconstruct.

FIG. 12A shows SPR data for adsorption of dsDNA onto the guanidinium functionalized surface. The trace in FIG. 12B shows that even acid treatments do not remove the DNA.

FIG. 13A shows 300 superimposed force curves for a PEG-tethered 15 base DNA oligomer interacting with a guanidinium functionalized surface. Most of the pulls indicate adhesion at one point (sharp peaks) but an example of an "adhesion plateau" is indicted. FIG. 13B is a scatter plot of peak force vs. pulling distance. Note that most of the larger forces lie in the PEG region and not the DNA region.

FIGS. 14A and 14B show the same region of the substrate before (FIG. 14A) and after (FIG. 14B) injection of DNA into the STM imaging cell (data taken in tris-HCl). The pits (arrows, FIG. 14A) disappear after DNA adsorption and some reconstruction of the underlying gold is evident in the shape changes of the small islands. Close inspection reveals a highly ordered monolayer of DNA. This is more obvious in the high contrast images shown in FIG. 14C of dsDNA and in FIG. 14D of ssDNA (Fourier transforms inset upper right).

FIGS. 15A-15D show current-decay curves obtained with a bare (green trace 151) or functionalized tip over various guanidinium surfaces. FIG. 15A; a guanidinium-functionalized surface (G-tip, pink traces 152); FIG. 15B: an oligo-T ($T_{45}$) adsorbed onto the guanidinium surface (C-tip, pink traces 153); FIG. 15C: an oligo-T ($T_{45}$) adsorbed onto the guanidinium surface (G-tip, orange traces 154); FIG. 15D: an oligo-C ($C_{45}$) adsorbed onto the guanidinium surface (G-tip, black traces 155). Data were obtained in Tris-HCl with a pH of 6.8.

FIG. 16A shows part of the infinite "chain; " FIG. 16B shows the energy levels; and FIG. 16C shows $\beta$ as a function of energy.

FIG. 17A shows a high-resolution imaging of a prior art nanogap. FIG. 17B shows a prior art nanogap sculpted by e-beam ablation (from Fischbein and Drndić, 2006 and 2007).

FIG. 18A shows a schematic layout, including a covering layer of $SiO_2$. FIG. 18C shows a cross section of gap. FIG. 18B shows a SEM image of a real device with another view into the nanogap shown in FIG. 18D.

FIG. 22A-C: Models for finite element analysis. 22A—2D model of the electrodeposition setup. 22B—A close-up including the double layer (EDL). 22C—Full 3D model of the electrodeposition setup including EDL structure.

FIG. 24. Base pairing of the adenine reader ($R_A$) with natural DNA bases.

FIG. 30. Base pairing of DAP with DNA bases and proposed analogues of DAP as candidates for the T reader.

FIG. 42 is Table 2 showing the calculated maximum inverse electronic decay length ($\beta$) for a unit cell length L in an infinitely repeated lattice of the structures shown here. Numbers in parenthesis are for the smaller $\beta$ resulting from the Fermi level alignment predicted by DFT.

DETAILED DESCRIPTION OF THE INVENTION

Figure 1:
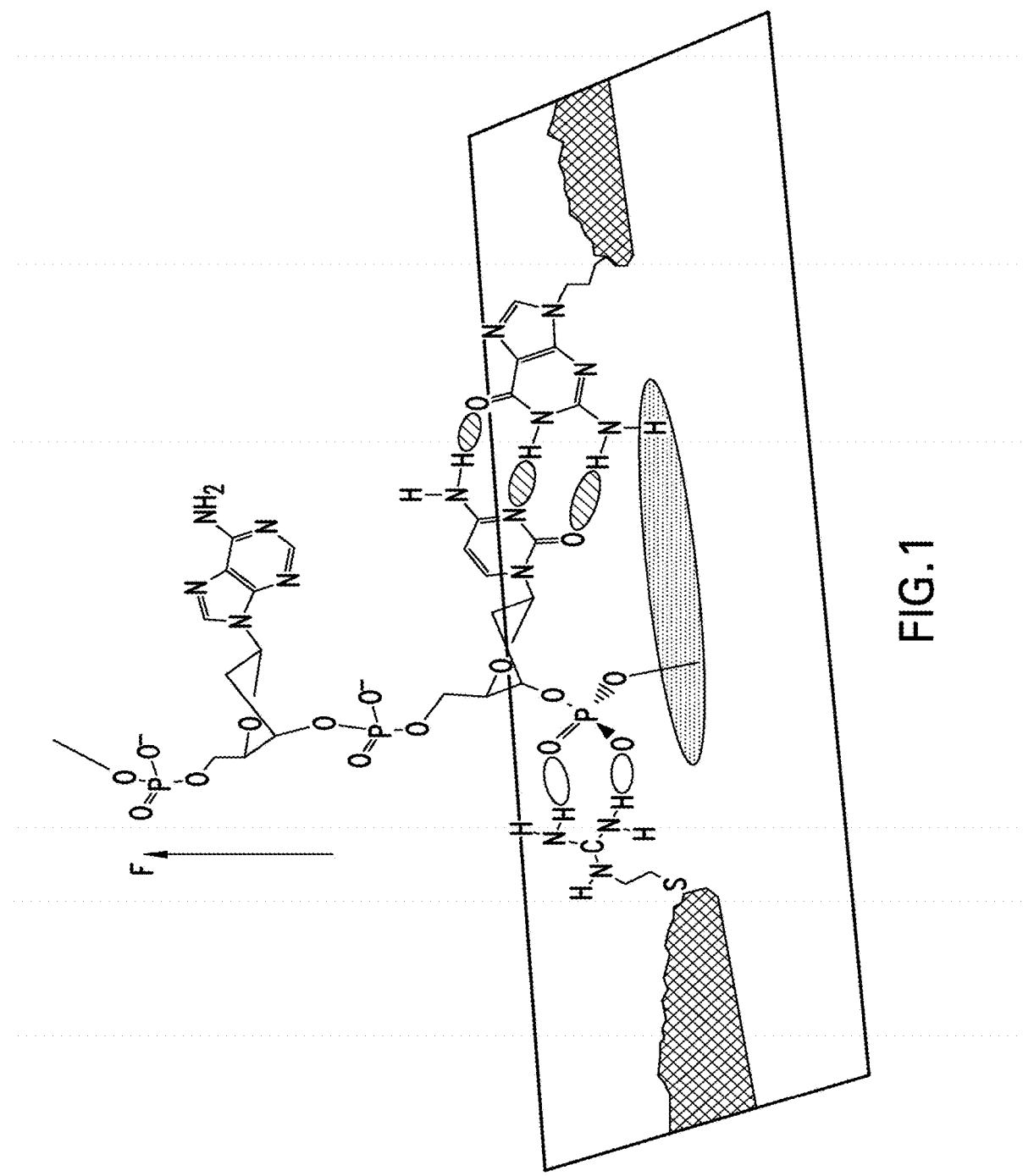
FIGS. 1 and 1A: Sequencing by recognition through affinity elements, showing one of four types of reader (this one is for C). A guanidinium ion tethered to one electrode via a flexible linker, hydrogen bonds (yellow H-bonds) onto the nearest passing phosphate on an ssDNA translocating a nanopore. If a flexibly tethered base on a second electrode finds it's Watson-Crick complement on the other side of the DNA (red H-bonds) a large current passes between the two electrodes, signaling a base recognition event. The components require an electrode gap of about 3 nm and an electrode height of no more than 0.6 nm or 0.7 nm. The H-bonding also serves to align the DNA in the device, while the flexible linkers provide alignment tolerance. Translocation is controlled via electrophoresis and magnetic beads (with net force F) an arrangement compatible with a parallel assembly of many reading heads.

FIG. 1 shows one embodiment of a device for sequencing single-stranded DNA (ssDNA) by hydrogen-bonding recognition, in accordance with the present invention. In its simplest form, each recognition-molecule (referred to as a 'base-reader') reads a specific DNA base, the full sequence being assembled by juxtaposing data from four different readers. As the ssDNA passes the electrodes via a constriction (e.g., a nanopore), a guanidinium ion grabs the nearest phosphate (depicted in FIG. 1 by the two yellow hydrogen bonds), while a base reader recognizes its Watson-Crick complement (depicted in FIG. 1 by the three red hydrogen bonds) when it is present. So long as both molecular recognition events overlap in time, a large current will flow, with the consequent charge pulse signaling identification of the target base.

Figure 1A:
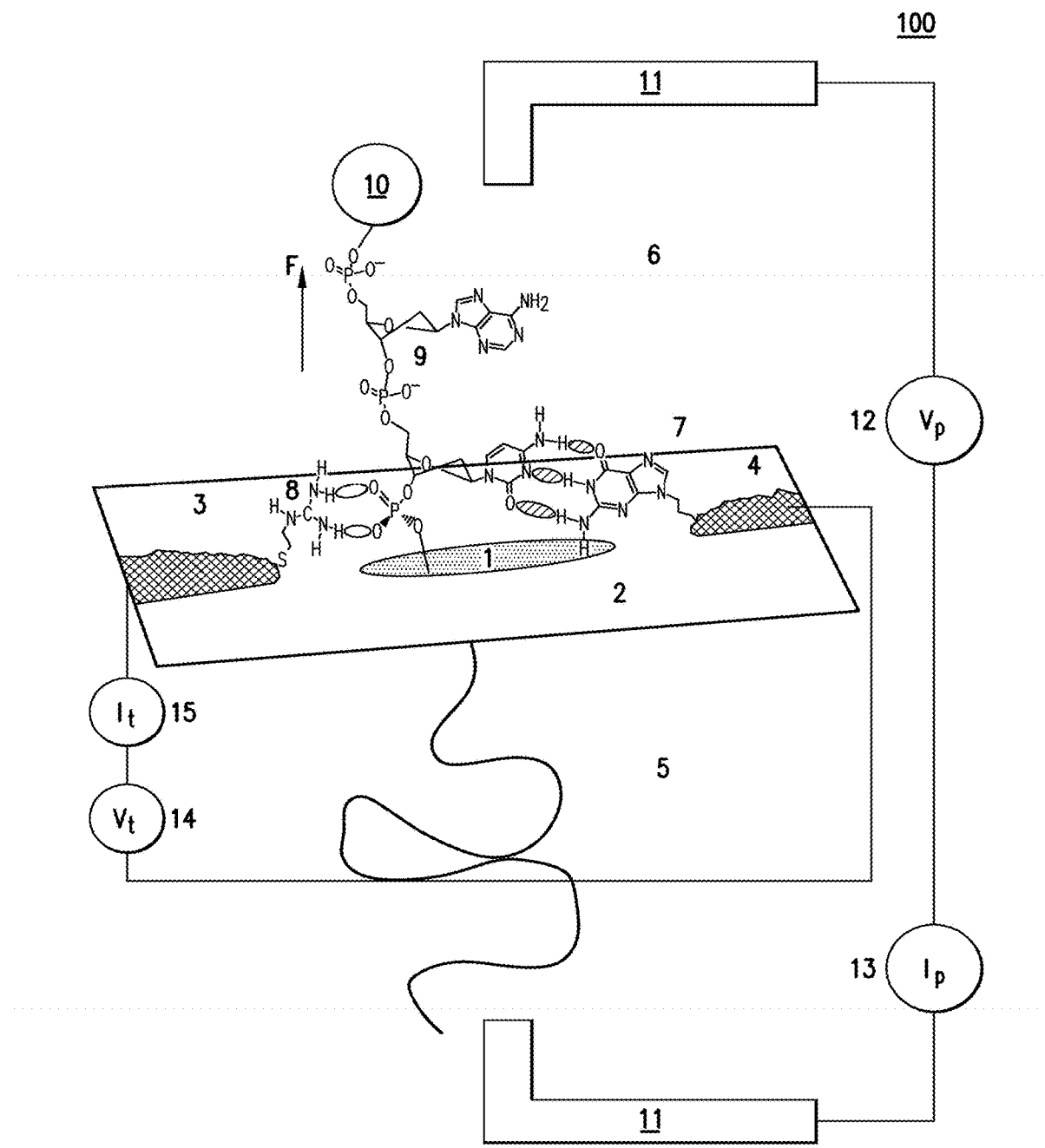

FIG. 1a shows the device 2 of FIG. 1 arranged in an apparatus 100 configured to read bases in ssDNA, by measuring tunneling current. A constriction in the form of a nanopore 1, is formed in the device 2. In one embodiment, the device 2 is comprises a chip 2 which, in turn, comprises a substrate provided on a thin $Si_3N_4$ membrane. The top of the chip 2 seen in FIG. 1A comprises a first side while the bottom of the chip 2, which is hidden from view in FIG. 1A, comprises a second side. Thus, the device 2 may be considered to comprise a partition having a first side and a second side, and the ssDNA translocates from one side of the partition to the other side of the partition, via the constriction 1. First and second electrically conductive sensing electrodes, 3, 4 which are spaced apart from one another by a gap, are provided adjacent the nanopore 1 on the first side of the chip 2. In one embodiment, the gap between the first and second electrodes is between 1.0-5.0 nm, though larger gaps may be possible. The first and second sensing electrodes are preferably formed of gold, though they may instead be formed of other electrically conductive materials.

The chip 2 is mounted in the device 100 such that the chip's first side (top) is exposed to a first fluid chamber 6 ("upper chamber") and the chips second side (bottom) is exposed to a second fluid chamber ("lower chamber"). As seen in FIG. 1A, the second fluid chamber 6 contains the ssDNA 9 to be read, while the first fluid chamber receives the ssDNA 9 translocating through the nanopore 1 which forms a passage between the two fluid chambers 5, 6.

On the first side of the nanopore 1, a first affinity element 8 is tethered to the first sensing electrode 3 via a first flexible linker. Generally speaking, a "linker" is a chemical designed so as to permit adequate motion of the affinity element to self-assemble on the target while remaining in electrical communication with an electrode. The first flexible linker itself may be bonded to the first electrode via an electrode attachment molecule, such as a thiol. In one embodiment, the first affinity element 8 comprises guanidinium or a guanidinium derivative such as guanidinoethyldisulfide. Guanidinium performs the function of grabbing the phosphate backbone of the ssDNA 9 and thus serves as "phosphate grabber."

On the second side of the nanopore, a second affinity element 7 is tethered to the second sensing electrode 4 via a second flexible linker. The second flexible linker itself may be bonded to the second electrode via an electrode attachment molecule, as described above. In one embodiment, the second affinity element 7 comprises a base reader which is configured to recognize one of the four bases on the ssDNA 9. In general, both the phosphate grabber and the base reader form chemical bonds that are readily broken at room temperature. Thus, the bonds formed during translocation are made and broken on a timescale that permits rapid binding and release of the target while still allowing for detection and measurement of a tunneling current.

In one embodiment, the flexible linkers associated with either or both sensing electrodes may comprise an alkane. A thiol serves as the electrode attachment molecule, and so the combined linker-electrode attachment molecule may comprise —$CH_2$—$CH_2$—SH.

As also seen in the embodiment of FIG. 1A, a first magnetic bead 10 may be affixed to a leading end of the ssDNA 9 and used to pull the ssDNA 9 through the nanopore 1. Optical tracking of the bead allows transit of the ssDNA to be followed to within 20 nm. It is understood, however, that a second magnetic bead may be used on the second side of the device (i.e., in second fluid chamber 5) to help untangle the secondary structure of the DNA.

A pair of polarization electrodes 11 are used to polarize the nanopore 1 for electrophoretic transport of the ssDNA 9. A voltage bias 12 and a current monitor 13 are used to control the electrophoretic transport.

The first and second sensing electrodes 3, 4 are connected to a sensing electrode bias 14 and also to current measuring circuitry 15 to gauge the tunneling current as each nucleotide is detected during translocation of the ssDNA 9. It is from the measured tunneling current at one or more nanopores that the corresponding portion of the ssDNA can be identified.

The chip 2 of the device 100 seen in FIG. 1A may be fabricated in a number of ways. In one embodiment, a number of such chips 2 may be created at the same time using a single wafer in conjunction with the following principal steps:

Step 1. Grow 100 nm $Si_3N_4$ on the top side of the Si wafer.

Step 2. Photolithographically pattern sensing wires on top of the $Si_3N_4$ using lift-off. The sensing wires will later be cut into two electrodes for each chip.

Step 3. Photolithographically pattern a reference electrode (RE) and a counter electrode (CE) on the underside, the RE and the CE being brought to the edge of the windows (see, e.g., FIGS. 18 & 21).

Step 4. Grow 200 nm $SiO_x$ on both top and bottom to insulate the various electrodes.

Step 5. Pattern and cut windows through SiOx and Si with HF and KOH etches, exposing part of CE and RE on underside.

Step 6. On FIB, cut through $SiO_x$ and cut sensing wires and shape ends. The gap between the electrodes is about 20 nm. Exposed metal area should be less than a few square microns to minimize leakage current from sensors.

Step 7. Turn chip and FIB mill nanopore through $Si_3N_4$ centered on gap between electrodes. The thus-formed pore is 5 to 10 nm at electrodes. Steps 5 and 6 can be done automatically under computer control for many devices.

Step 8. Clean excess Ga ions from FIB milling with nitric acid.

Step 9. Place gold plating solution below the chip (Si side) and salt solution above it ($Si_3N_4$ side).

Step 10. Plate Au onto sensing electrodes until a predetermined tunnel current is obtained between the two sensing electrodes. If this is coincident with a drop in the pore ionic current ($I_P$) then the electrodes are centered. The parameters may be adjusted so that this process can be automated for production.

Step 11. Open gap by stripping Au to achieve optimal size.

Step 12. Rinse.

Step 13. Functionalize the chips by exposing them to equimolar mix of phosphate grabber and base reader.

Step 14. If specific functionalization is necessary, hold one electrode at >–1V Ag/AgCl and load a first recognition reagent comprising the first affinity element. Rinse and then expose to the second recognition reagent which comprises the second affinity element. Rinse again.

Step 15. Mount chip in device so as to form the lower chamber 5 and upper chamber 6.

It is understood that the wafer may have an large array of such nanopores. In some embodiments, all the nanopores on a wafer may be functionalized in the same exact manner. In other embodiments, however, the nanopores on a wafer need not all be functionalized with the same exact affinity elements.

In one embodiment, the wafer may be considered to comprise an array of 2×2 sub-arrays. Each nanopore in a 2×2 subarray may then have a phosphate grabber (such as guanidinium) as the first affinity element and a different one of the four base readers as the second affinity element. This way, each 2×2 subarray comprises all four base readers for use in devices configured for "parallel" DNA sequencing.

The wafer may then be cut into chips, each chip having a single 2×2. Alternatively, the wafer may be cut into larger chips, each such chip comprising a plurality of such 2×2 subarrays. This redundancy on a chip can increase the certainty of recognition, as discussed further below.

It is understood that multiple 1×4 sub-arrays may be formed instead of 2×2 subarrays. In such case, the wafer may be considered to comprise rows of nanopores whose members are similarly functionalized. For instance, the wafer may comprise a number of rows that is a multiple of four. Each nanopore in a given row may then have a phosphate grabber as the first affinity element, and the same base reader as the second affinity element. Four rows that are adjacent to one another, may then have a different base reader as the second affinity element in all their nanopores. This allows one to cut up such a wafer into chips comprising a single 1×4 subarray, or even into larger chips comprising a plurality of such 1×4 subarrays.

Each nanopore 1 is functionalized by its associated second affinity element 7 to recognize one of the four bases. Therefore, to sequence DNA, it is understood that either: (a) a single copy of the DNA must pass through a "gauntlet" comprising four differently functionalized nanopores ("serial read"), or (b) four identical copies of ssDNA must pass through four distinct, differently functionalized nanopores ("parallel read").

When a single copy of DNA is used, the nanopores belong to different chips and the DNA is threaded through the four chips. Readouts of the electrical current detected from each of the four nanopores can be aligned, using the known rate of translocation and peak current values signifying a match to determine the DNA sequence.

When four identical copies of DNA are used, it is desirable that they translocate in synchrony. Readouts of the electrical current detected from each of the four nanopores can then be compared to look for peak values signifying a match.

Thus, in one embodiment, a device may be used to sequence DNA by the following set of principal steps:

Step 1. A plurality of such nanopores, each functionalized to recognize one of the four bases, should be provided. This can be done using either serial reads or parallel reads, as described above.

Step 2. Place DNA in lower chamber associated with each such nanopore. Optionally modify the DNA so as to allow entry into the pore from one direction only. In one embodiment, this may be done by tethering the DNA to a bead.

Step 3. Electrophorese the DNA through the pore. If extra pulling force is needed, functionalize the end that passes through pore (after having been modified with e.g., biotin) and attach magnetic bead.

Step 4. Pull DNA through by electrophoresis and/or magnetic bead.

Step 5. Record current pulses ($I_t$) as a function of time.

Step 6. Align data from a plurality of reads for each type of base reader.

Step 7. Align data from all 4 reads.

Figure 4:
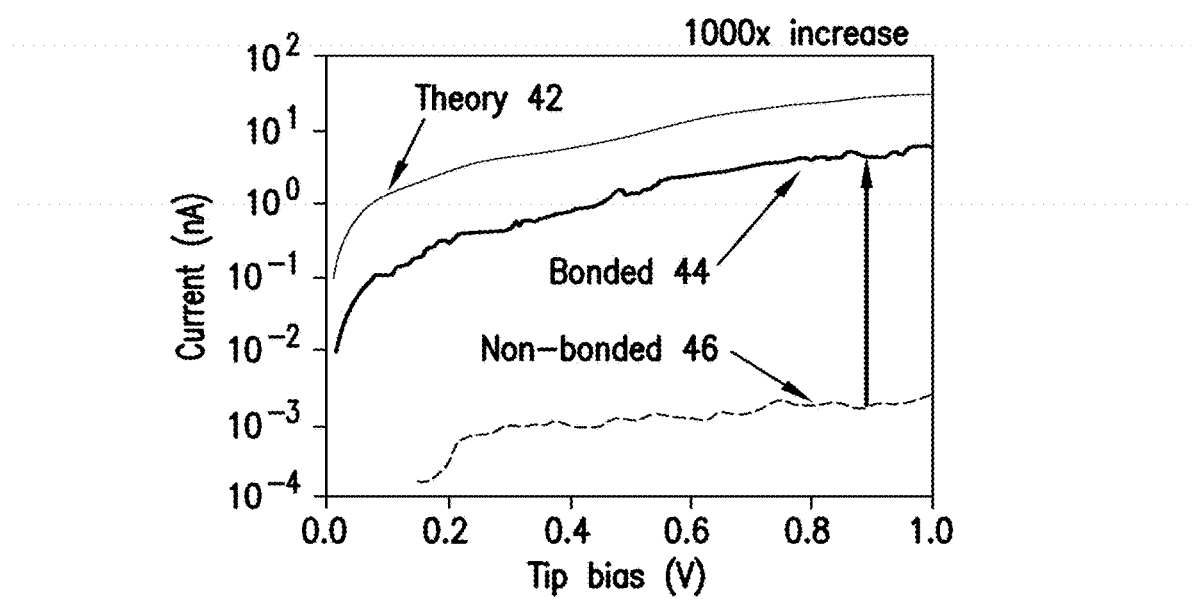
FIG. 4: Current (log scale) vs. bias for the probe pushed against an alkane monothiol monolayer ("Non-bonded"), bonded to a gold nanoparticle ("Bonded") and, as calculated from first-principles ("Theory").

FIG. 4 illustrates that the current through a "good chemical contact" can be thousands of time larger than current through a simple physical contact. When the bonding in question is carried out by means of hydrogen bonds, it is both (a) reversible and (b) capable of molecular recognition.

The present invention utilizes the principle of hydrogen bonding for molecular recognition. A number of measurements of hydrogen-bond mediated tunneling using various combinations of bases that form Watson-Crick or mismatch hydrogen bonding have demonstrated the feasibility of this readout.[90]

Figure 5:
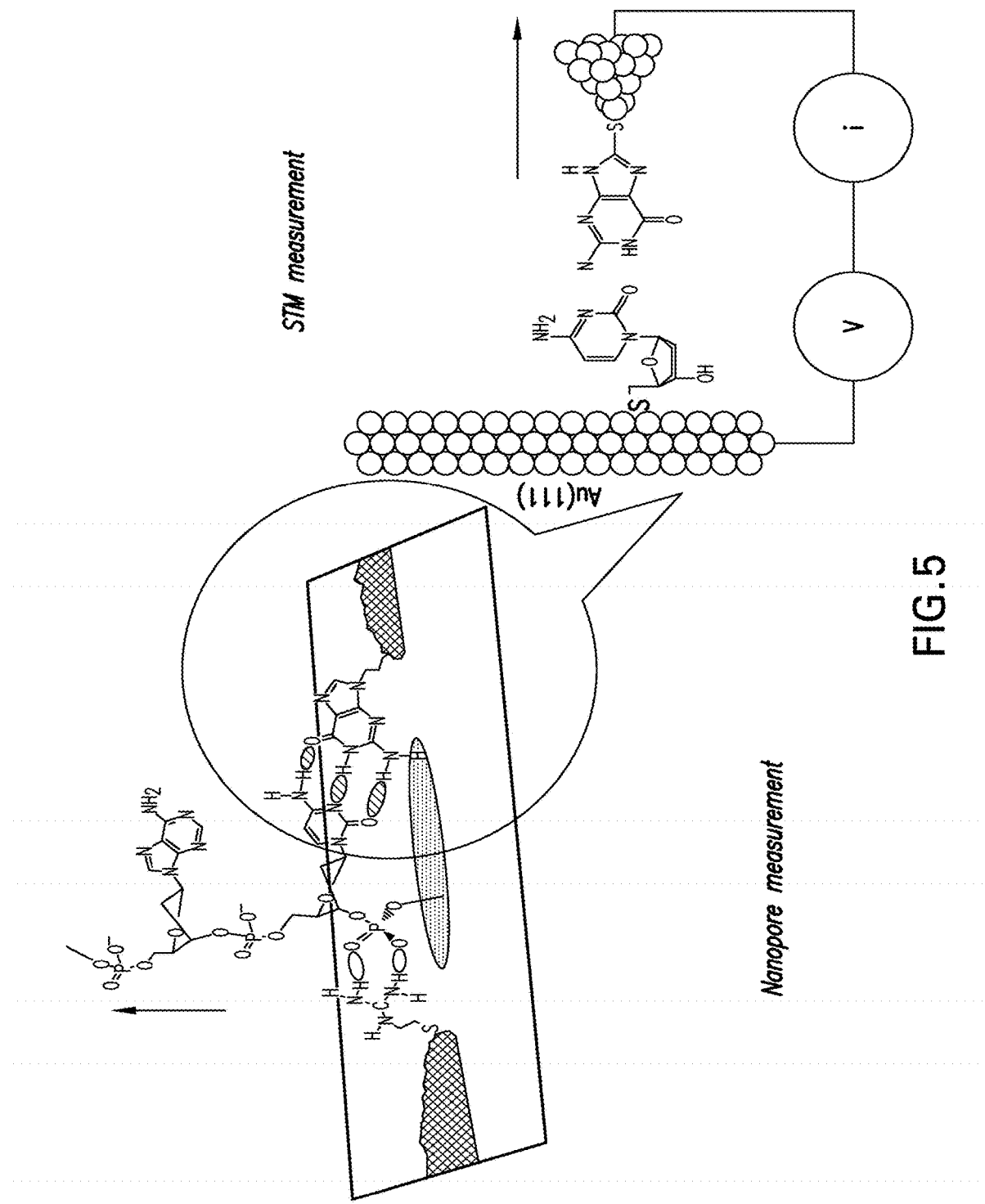
FIG. 5: Shows how half of the nanopore measurement is modeled in an STM measurement (a moving, functionalized, electrode moves away from a fixed DNA base), whereas in FIG. 1 the DNA base moves away from a fixed, functionalized, electrode.

FIG. 5 shows the way in which STM measurements map onto a preferred embodiment of nanopore measurement. Monolayers of bases on gold using thiolated nucleosides are formed for the purpose.[91-93] Thiolated nucleosides were chosen to overcome the tendency of bases to lie flat on gold.[94] Both 5'-mercaptode oxycytidine (i-referred to as "C") and 5'-mercaptothymidine (ii—referred to as "T") have been shown to be effective for this purpose. They form Watson-Crick (i) and G-T wobble (ii) base pairs with guanine[95].

STM images of monolayers of these nucleosides confirm the phenomenon reported by Ohshiro and Umezawa:[12] The contrast obtained in images taken with a complementary base on the probe (e.g., 8-mercaptoguanine imaging a 5'-thio-deoxycytidine monolayer) was approximately double that obtained with a thio-phenol functionalized probe used as a control (see the appendix[90]). However, measurements of tunnel current as a function of distance (as illustrated in FIG. 6) are much more striking and relevant to the present invention.

Figure 6A:
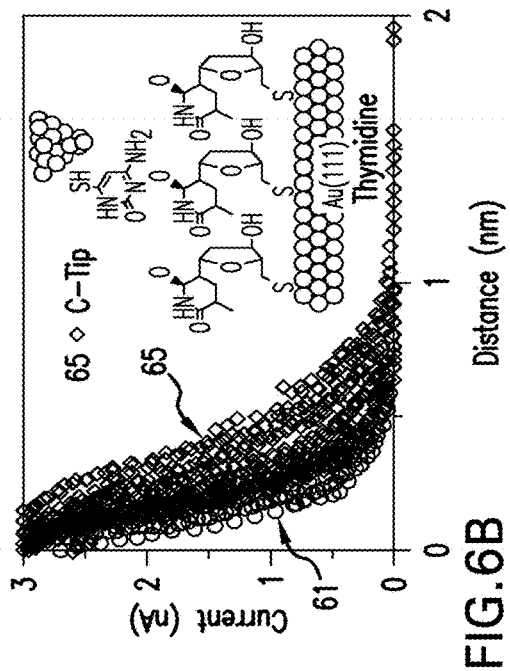
FIGS. 6A-6D.
Figure 6B:
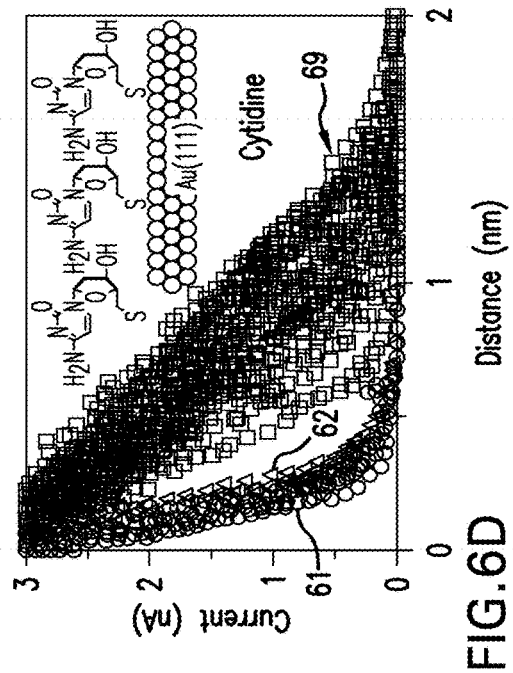
Figure 6C:
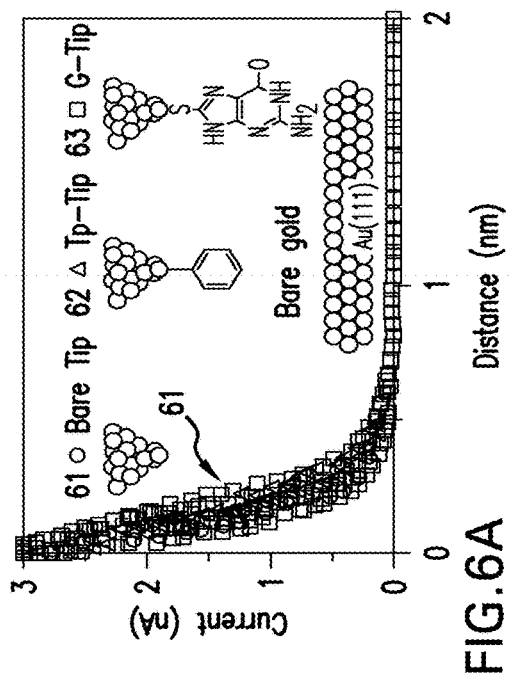
Figure 6D:
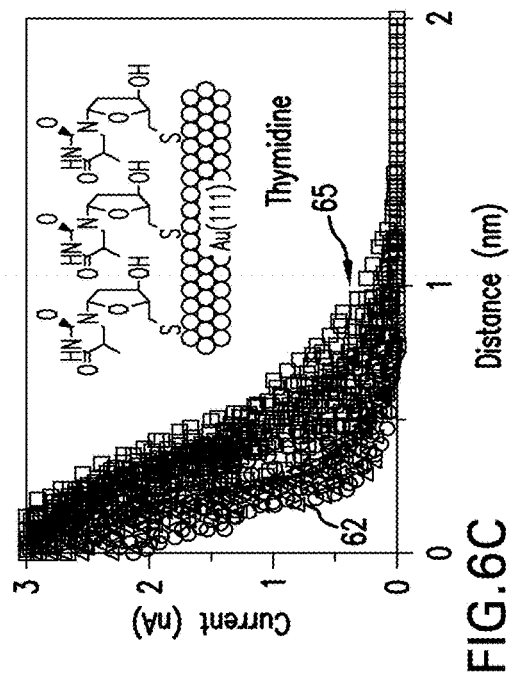

FIGS. 6A-6D show data measurements of tunnel current as a function of distance. In order to appreciate the significance of these results, it must be understood that these are raw, unselected data. Individual curves have simply been superimposed, with different colors corresponding to different experimental conditions. The separation of data from the various types of measurement is immediately obvious even with this presentation of overlapped, multiple traces. FIG. 6A shows the effect of the controls (a bare Au tip 61, a thiophenol functionalized tip 62 or a G-functionalized tip 63 on bare gold. All of these produce rapid decays of the tunnel current, and the resulting curves overlap, making them difficult to distinguish from one another. FIG. 6B shows that data for a C-functionalized probe on a T monolayer produces curves 65 that extend somewhat further in distance than curves 61 from the bare Au. As seen in FIG. 6C, curves 65 for the wobble-basepair (G-T) extend yet further. As seen in FIG. 6D, the data for the Watson Crick G-C basepairs are distinguished by a remarkable extension of the distance over which tunnel current is sustained (upper traces 69). Thus, curves that correspond to the Watson Crick basepairing are immediately identifiable in the raw data. Initial conditions are i=3 nA, V=0.5V, retraction speed=133 nm/s. These data were taken in trichlorobenzene.

FIGS. 7A and 7B show a selection of just a few curves from each of the G-C experiments (FIG. 7A) and G-T experiments (FIG. 7B) to illustrate subsequent analysis. Curves can be fitted to two separate regions of exponential decay;

$$i = i_0 \exp(-\beta_1 z) \quad 0 < z < z_c \quad (1a)$$

$$i = i(z_c) \exp(-\beta_2 (z - z_c)) \quad z_c < z \quad (1b)$$

The fits are shown by the solid lines in FIGS. 7A and 7B and they lie on top of the experimental data. The important features of this process are:

The slopes, characterized by $\beta_1$ and $\beta_2$ are not very different between G-C and G-T basepairs.

The values for $\beta_1$ (about 0.1 Å$^{-1}$) are much too small to correspond to true electronic decay constants.

The values for $\beta_2$ (about 0.4 Å$^{-1}$) are typical of decay in the solvent alone and in line with previous measurements of decay in a liquid medium.[96]

The distance at which the decay transitions from behavior characterized by pi to behavior characterized by $\beta_2$ ($z_c$) depends strongly on the type of basepair (G-C vs. G-T). Arrows point to the transition between the slow decay ($\beta_1$) and the rapid decay ($\beta_1$) regions at a distance $z_c$.

One interpretation of these data is that the first region corresponds to stretching of the hydrogen bonded complex. The small apparent decay length is readily explained if other components of the system (e.g., bond rotations) are weaker than hydrogen bonds by a factor often or so.[90] This is because the probe motion corresponds to the strain of the complete system (including a deformable STM probe[97]) while the tunneling is likely controlled by the actual strain of the hydrogen bonds (see below) which will be much less if they are "stiffer."[98] Because the decay in the second region is similar to that in solvent, it can be ascribed to the response of the system after the hydrogen bonds have broken. Therefore the breakpoints, $z_c$, are a measure of H-bond strength.

Figure 8A:
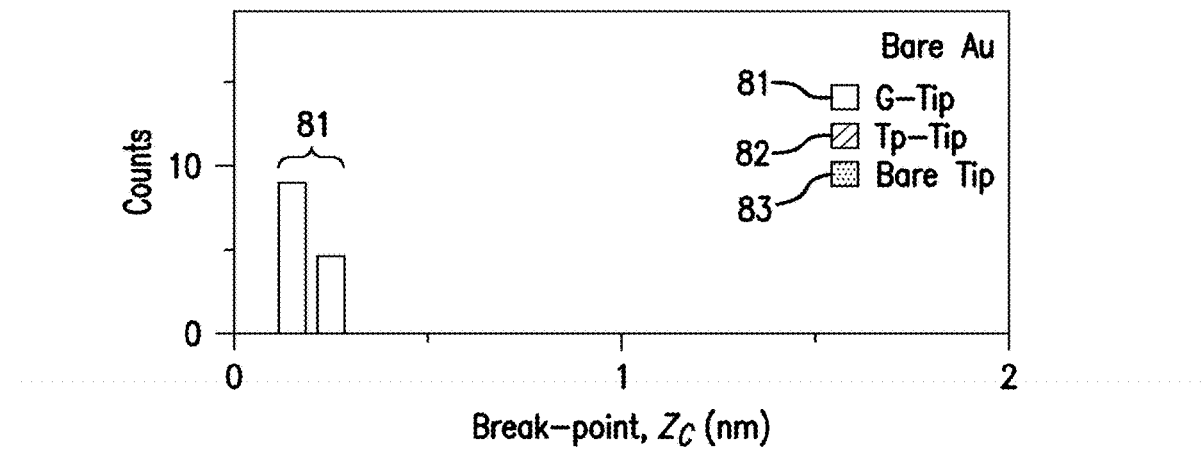
FIGS. 8A-8G 8A-8C: Histograms (black bars) of the values of the breakpoint, $z_c$, for bare Au (a), a deoxycytidine SAM (b) and a thymidine SAM (c) for the i-z curves shown in FIG. 1 (80% of data are fitted).
Figure 8B:
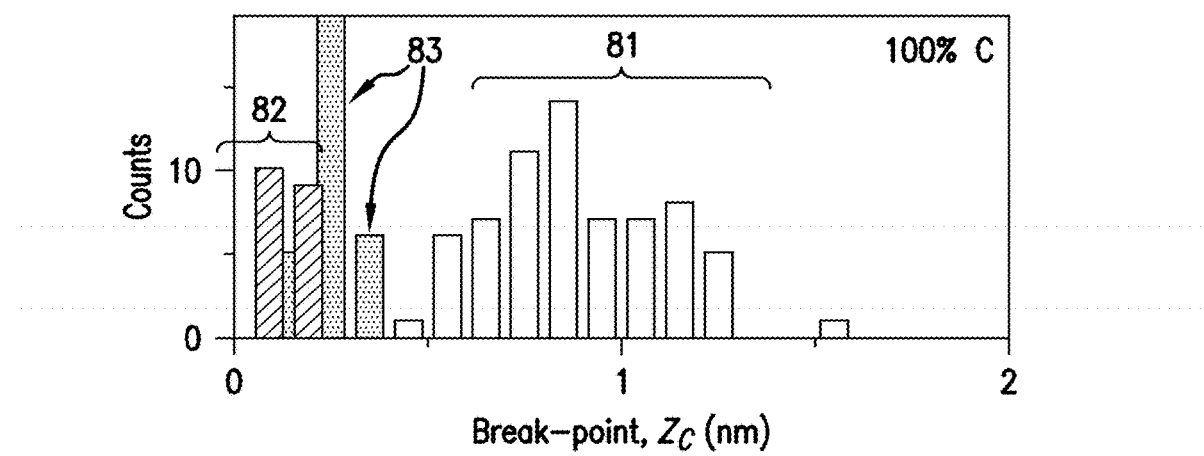
Figure 8C:
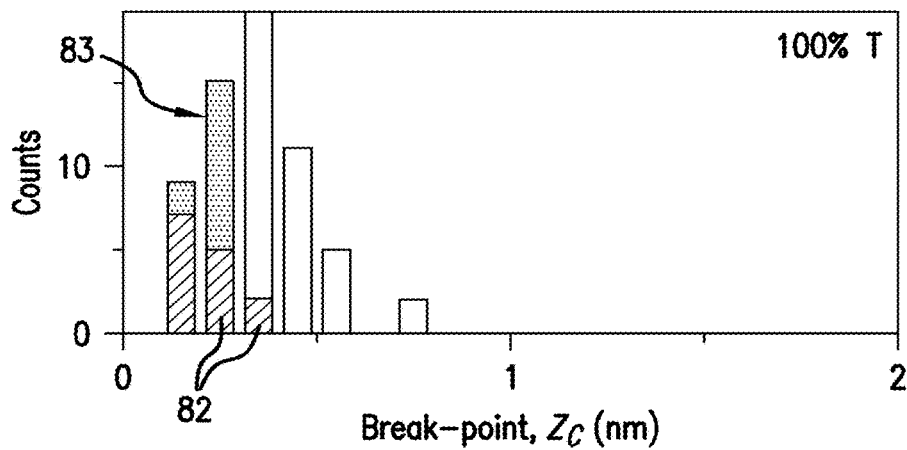
Figure 8D:
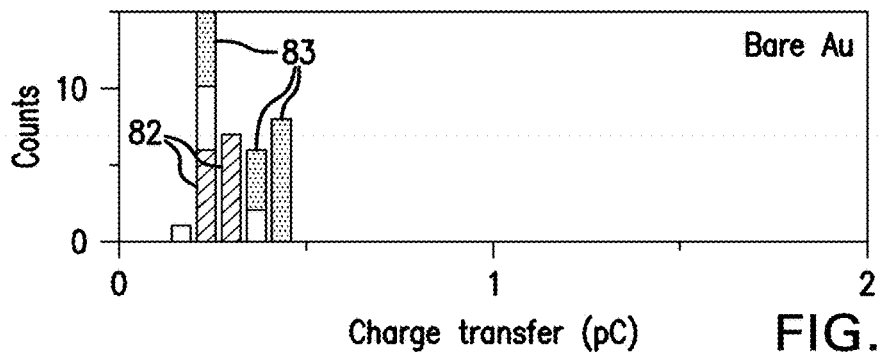
Figure 8E:
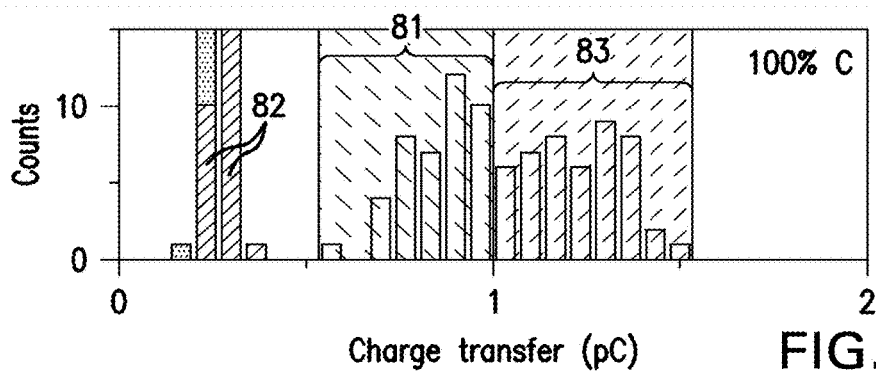
Figure 8F:
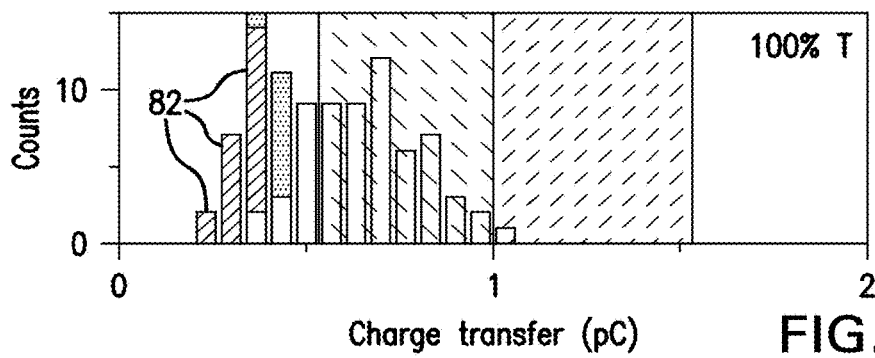

FIGS. 8A-8C show histograms of the values of $z_c$ for the various experiments, using each of a G-Tip 81, a Tp-Tip 82 and a Bare Tip 83. It is clearly an excellent parameter with which to distinguish G-C from G-T basepairs in single molecule measurements. Only about 80% of the curves are amenable to the analysis just described. The remaining 20% are too noisy, or show no obvious breakpoint. Nonetheless, as is clear from FIG. 6, all of the data appear to be useful. A second, much simpler approach is to integrate each curve. The horizontal axis corresponds to time, when converted using the known retraction velocity of the probe. Thus, the area under each curve (time×current) corresponds to the total charge transferred in each interaction.

Figure 8G:
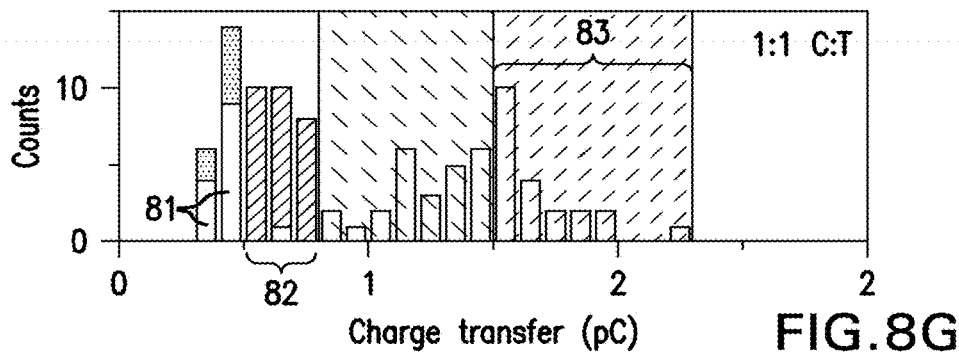

FIGS. 8D-8G histogram this total charge in picoCoulombs (pC). In addition to control data with bare AU (FIG. 8D), C-G data (FIG. 8B) and G-T data (FIG. 8F), also shown is data taken from monolayers made with an equimolar mix of C and T (FIG. 8G). The green shading on the figure illustrates how values of charge transfer above 15 pC uniquely identify G-C pairing. This occurs in about half the reads.

These data have four qualitative characteristics.

First, these data appear to be robust even though tunneling spectroscopy is known to be strongly affected by contamination and geometry. This may be a consequence of the bonded nature of the tunneling assembly. The H-bonds appear to work just like the gold-thiol bonds that generated the data shown in FIGS. 3 and 4, as explained herein.

Second, these results reflect single molecule interactions and so equivalent geometry can also be realized using a nanopore having translocated ssDNA passing therethrough. The reproducible data shown in FIG. 6 is obtained using sharp probes, specifically probes that are sharp enough to give single molecule resolution in an STM image. In the nanopore, where electrodes would be densely functionalized with, e.g., guanidinium or the base reader, the presence of only one ssDNA strand will guarantee single molecule interactions, with the caveat that the electrode gap and affinity element reach be no more than the gap between two bases in stretched DNA (ca 1.2 nm flanking the central base).

Third, the fidelity of the readout is adequate for detecting individual nucleotides. The data presented in FIG. 8 show that an unambiguous positive signal can be obtained in about half of the reads. Since $(0.5)^{13} \ll 10^{-4}$, the target, of 99.99% base calling accuracy could be obtained with as few as 13 independent reads. Even though the numbers may be somewhat less favorable when all the types of cross reactions are measured (a situation that might be mitigated with "designed base-readers"), a small unambiguously positive signal can be handled with an adequate number of independent reads.

Finally, the magnitude of the signal in these figures is not extraordinary. The magnitudes show that the H-bond mediated conductance is rather high. However, simulations show that the magnitudes of these signals are on the order of magnitude to be expected for H-bond mediated tunneling.

In the foregoing experiments. Tricholorobenzene (TCB) was chosen as a medium since the hydrogen bonding interaction between DNA bases and the base-reader would be too weak to be measured in water, owing to competition from H-bonds with water molecules. However, in a preferred embodiment water is the medium, since it is most often used dissolving DMA. The novel technique works almost as well in water as it does in TCB.

Figure 9A:
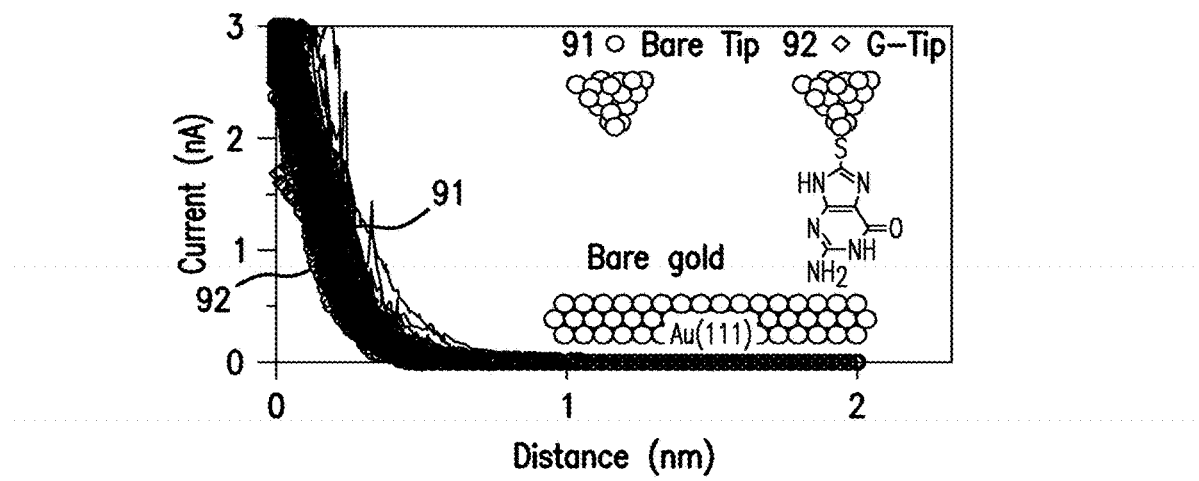
FIGS. 9A-9C. Raw current vs. distance data taken in water. Color coding for the curves and experimental conditions are otherwise as in FIG. 6.
Figure 9B:
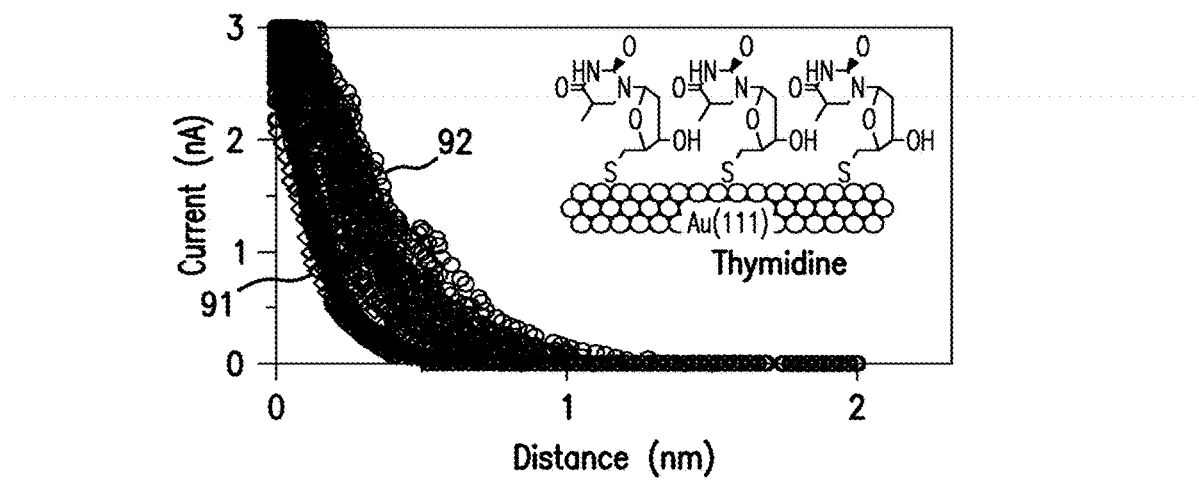
Figure 9C:
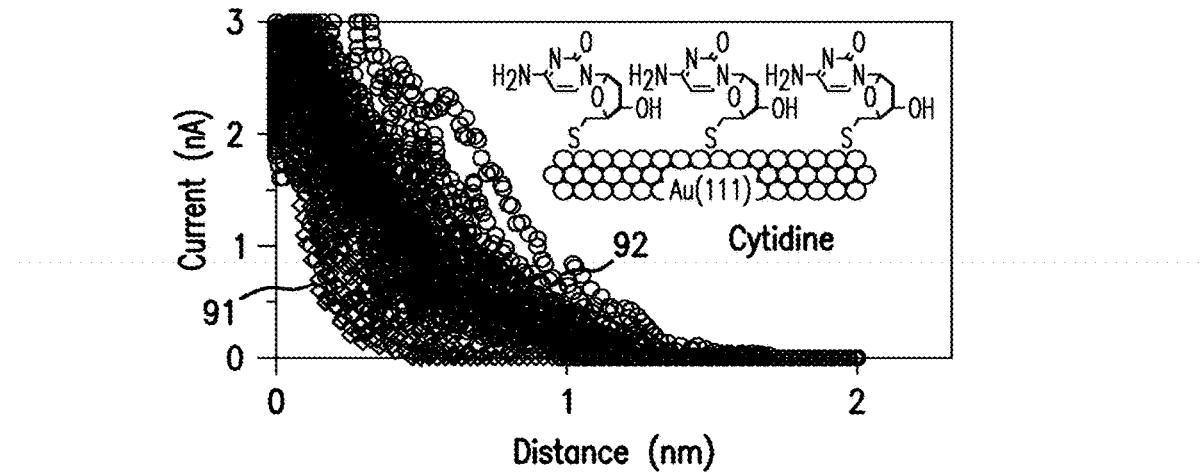

FIG. 9 presents raw current-distance data when water is used as the medium. Once again, the signature of H-bonding is clear and G-C pairs (black curves 92 FIG. 9C) are readily distinguished from G-T pairs (black curves 92 FIG. 9Bb).

Figure 10A:
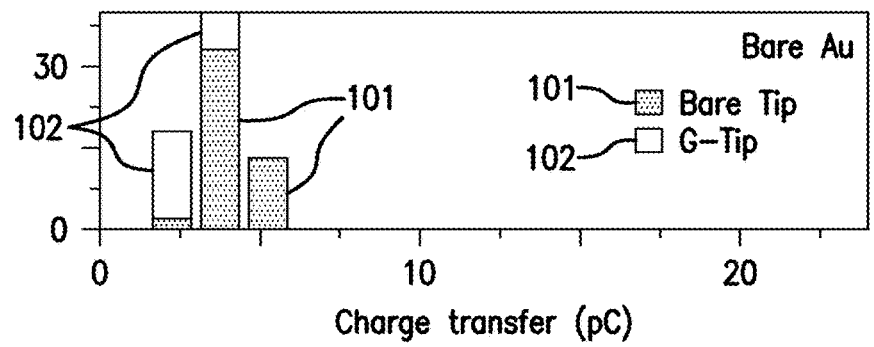
FIGS. 10A-10G. Analysis of decay curves taken in water. Histograms of the charge transferred in each retraction are shown in FIG. 10A (bare Au), FIG. 10B (deoxycytidine SAM) and FIG. 10C (thymidine SAM). Black bars 102 are for an 8-mercaptoguanine functionalized tip and green bars 101 are for a bare Au tip. Typical i-z curves in water (FIGS. 10E & 10G) are compared with their counterparts in trichlorobenzene (FIGS. 10D & 10F) showing the complex structure of the data obtained in water (green curves are control data obtained with bare tips).
Figure 10B:
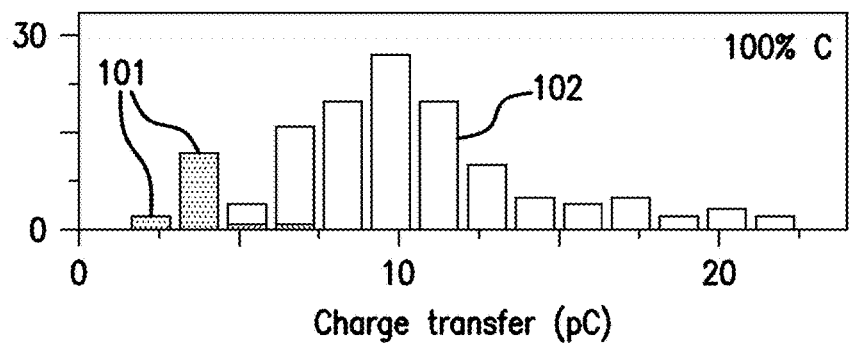
Figure 10C:
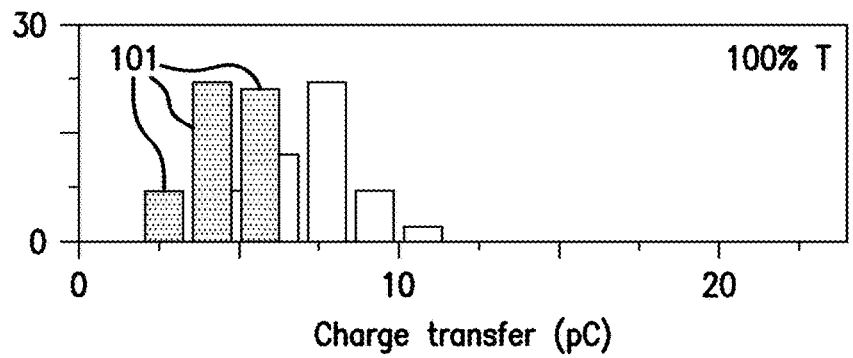
Figure 10D:
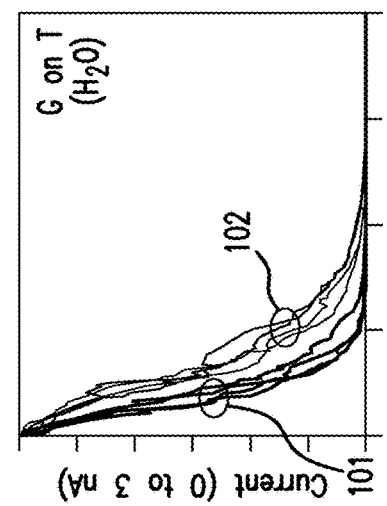
Figure 10E:
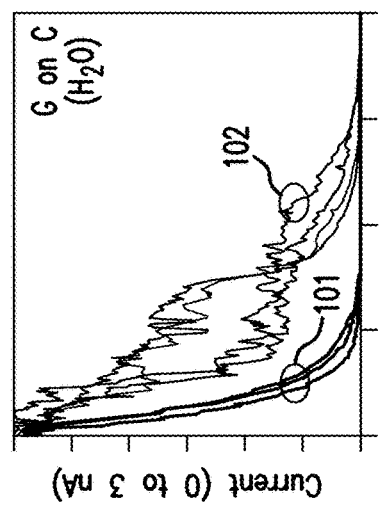
Figure 10F:
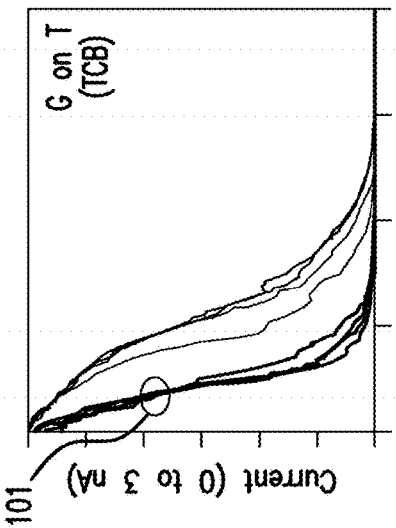
Figure 10G:
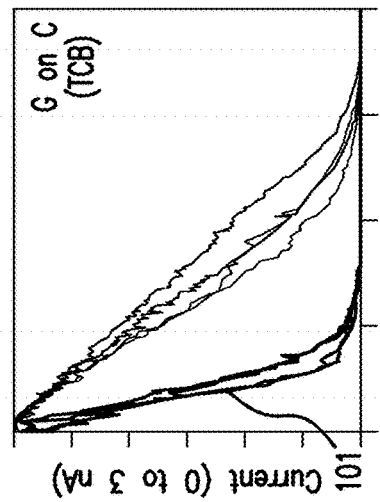

FIGS. 10A, 10B and 10C show histograms of the corresponding charge transfer signals and contrast the results using a bare tip 101 and a G-tip 102. As seen in FIGS. 10D-10G, C-T base-pairs are less readily distinguished in water than in TCB in these conditions. This result in water may be explained by looking at individual curves in detail, especially as seen in FIGS. 10E and 10G. The curves show features that suggest that the H-bonds do indeed break sooner in water, but the current signal has a complex shape and persists for a relatively long time. This may reflect the formation of water bridges between the bases. This would account for the increased signal from C-T pairs which are known to involve the formation of water bridges[99].

Forming Guanidinium Contacts to DNA

Figure 11A:
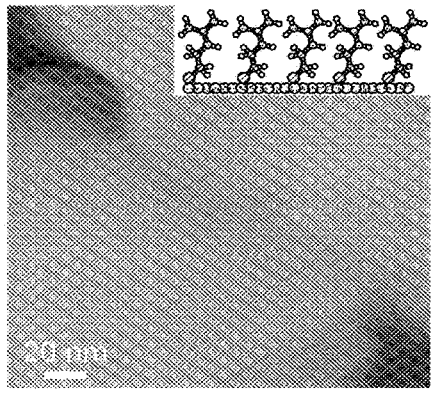
FIGS. 11A-11D: Guanidinium monolayer on Au(111).
Figure 11B:
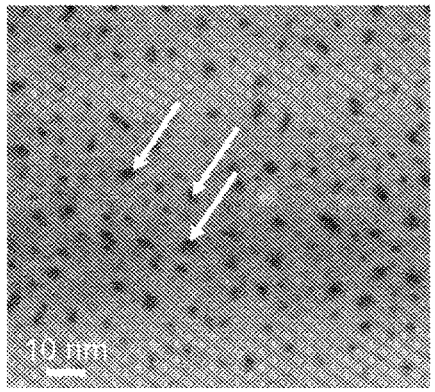
Figure 11C:
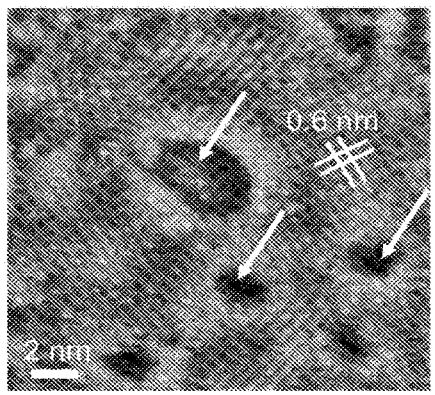
Figure 11D:
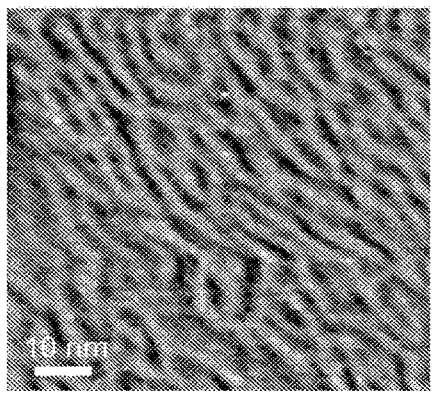

FIG. 11A shows a monolayer of guanidinium monolayer on AU(111), 1,1'-(dithiodiethylene) diguanidine was synthesized by reacting cystamine with N,N-bis(tert-butoxycarbonyl)thiourea in the presence of 2-chloro-1-methylpyridiniumiodide (in dimethylformamide at room temperature),[100] followed by acid treatment. This reagent was converted to β-mercaptoethylguanidinc (inset. FIG. 11A) on a TCEP (tris(2-carboxyethyl) phosphine)-immobilized gel immediately before use. The guanidinium monolayer on Au was verified by Fourier transform infrared reflectance (FTIR) spectroscopy and ellipsometry. STM images of these monolayers are shown in FIGS. 11A, 11B and 11C. The guanidinium molecule forms a square lattice with a lattice constant of about 6 Å (FIG. 11C). These images were taken in tris-HCl (pH 7) but the surface was found to be very sensitive to the presence of other ions. In particular, addition of phosphate buffer (pH 7) causes the surface to reconstruct completely, removing the single atom deep "pits" in the gold (arrows in FIGS. 11B and 11C) and forming ribbon-like structures on the surface (FIG. 11D).

Figure 12A:
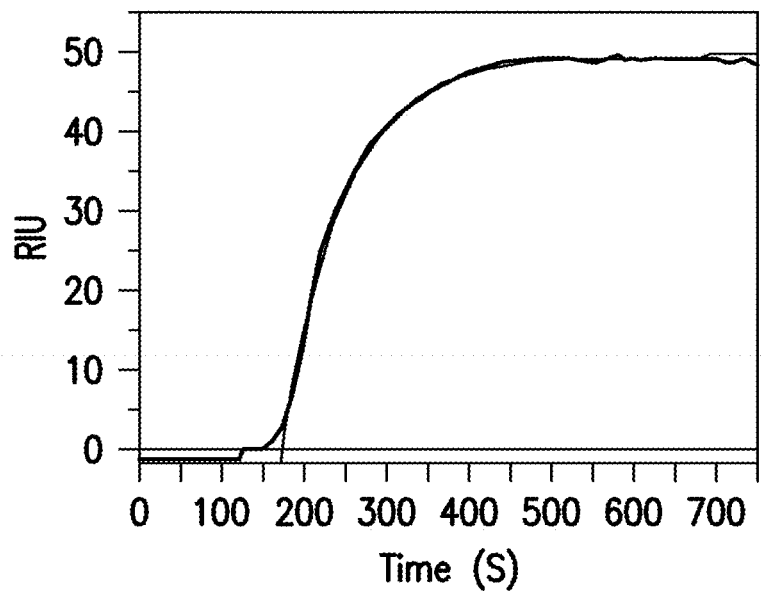
FIGS. 12A-12B.
Figure 12B:
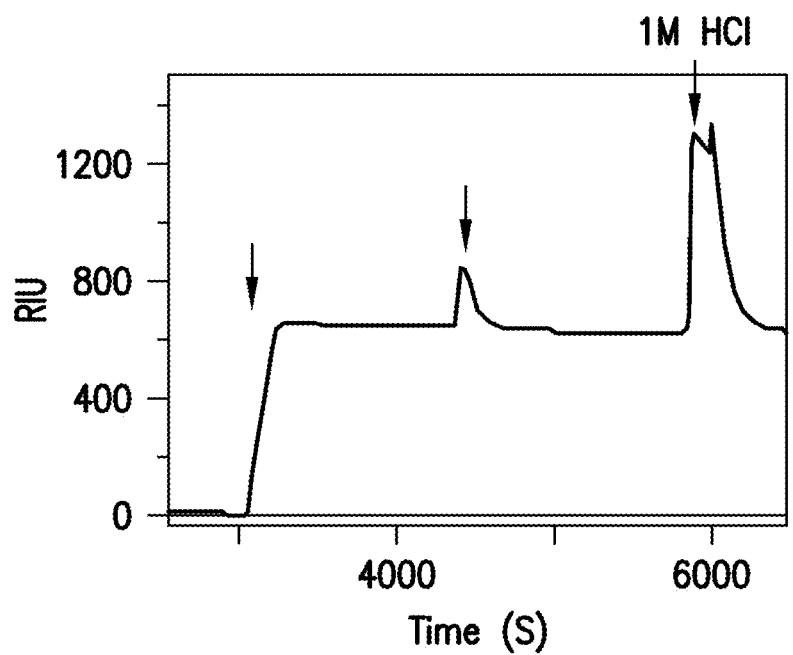

FIGS. 12A-12B illustrate surface plasmon resonance (SPR) data, which shows that DNA is rapidly and irreversibly adsorbed onto this surface. The adsorption is specific because it is blocked in the presence of phosphate. Interestingly, the interaction of a single DNA molecule with the surface is reversible. Single molecule interaction was tested by tethering a 15 base oligomer to an AFM probe with a polyethyleneglycol (PEG) linker and measuring the adhesion as the probe was pushed into the surface and then retracted. FIG. 12A shows SPR data for adsorption of dsDNA onto the guanidinium functionalized surface. The trace in FIG. 12B shows that even acid treatments do not remove the DNA.

Figure 13A:
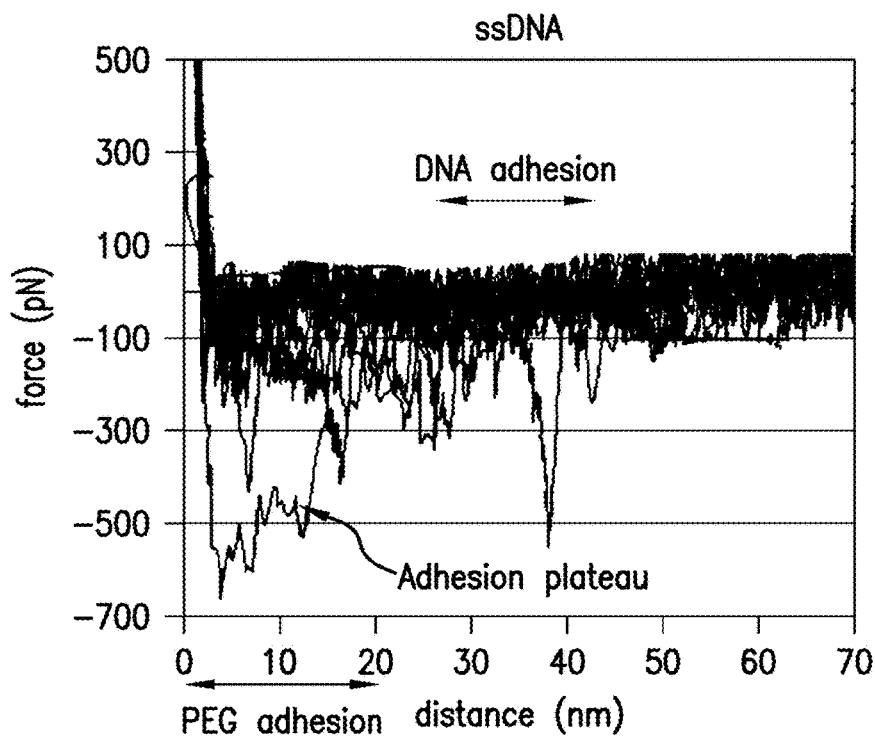
FIGS. 13A-13B.
Figure 13B:
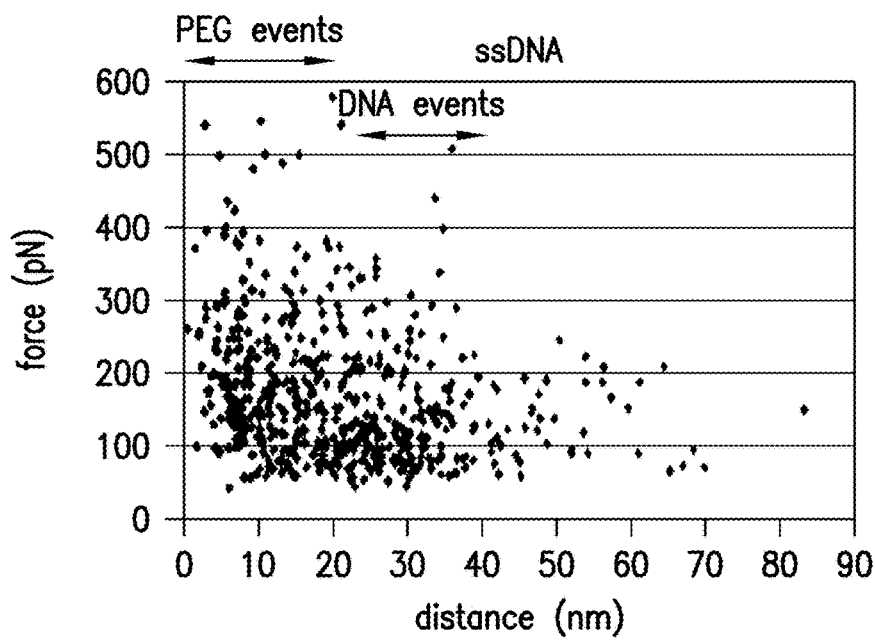

FIG. 13A shows 300 superimposed force curves (A) for a PEG-tethered 15 base DNA oligomer interacting with a guanidinium functionalized surface. Most of the pulls indicate adhesion at one point (sharp peaks) but an example of an "adhesion plateau" is indicted. FIG. 13B is a scatter plot of peak force vs. pulling distance. Note that most of the larger forces lie in the PEG region and not the DNA region. Thus, while FIG. 13A shows an accumulation of typical force curves, FIG. 13B shows a scatter plot of force peak height vs. the distance at which the event occurred. Events in the first 20 nm correspond to the PEG-tether length, while events between 20 and 30 nm correspond to interactions with the DNA at the end of the PEG (there are a small number of weak, non-specific interactions at larger distances). The PEG adhesion is generally larger than the DNA adhesion. The DNA features are generally consistent with the formation of one, or a few H-bonds. Thus the irreversible adsorption of DNA to the guanidinium surface is a consequence of a cooperative interaction between the DNA molecules, analogous to DNA condensation by multivalent ions.[101]

Figure 14A:
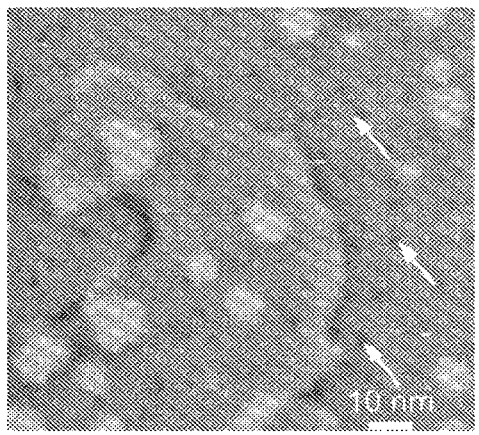
FIGS. 14A-14D: DNA adsorption onto the guanidinium monolayer.
Figure 14B:
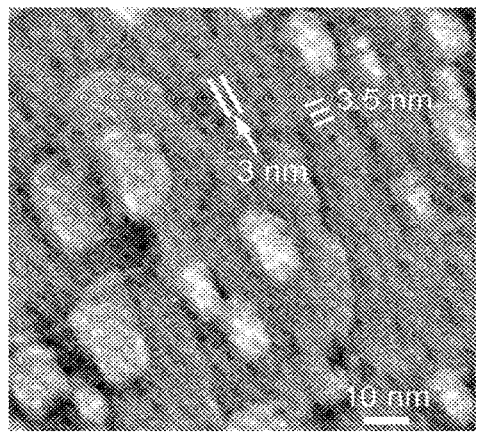
Figure 14C:
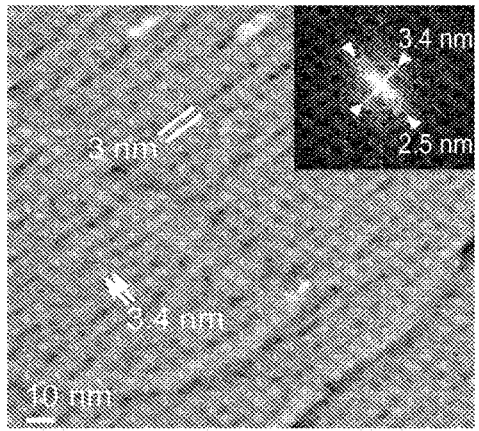
Figure 14D:
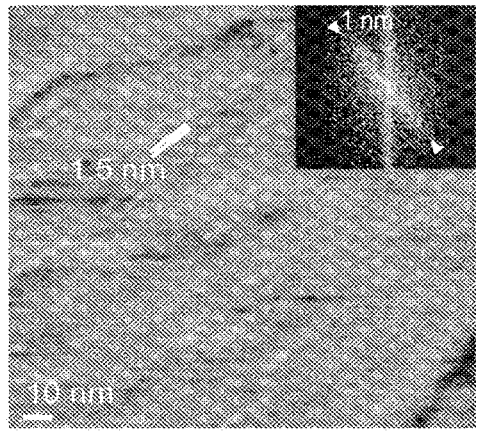

FIGS. 14A-14D shows STM images of DNA adsorption onto the guanidinium surface. The work of Ohshiro and Umezawa[12] (who used peptide nucleic acid, not DNA) and some recent studies in vacuum[102] notwithstanding, STM imaging of DNA is controversial.[103] Therefore, FIG. 14 shows the results of imaging the same region of the substrate before and after injection of DNA into the liquid cell of the microscope. The results are summarized in FIGS. 14A (pre-DNA injection) and 14B (post DNA injection). Just as in the case of phosphate ion (FIG. 11D), adsorption of DNA lifts the reconstruction of the gold, leading to a loss of the "pits". The movement of the underlying gold is clear from the shape changes in the small gold islands. Close inspection of FIG. 14B shows that DNA strands appear to have been adsorbed in a highly ordered monolayer in which the long axis of the strands makes an angle of about 30° with respect to the vertical axis of the image. This spontaneous alignment does not occur for short molecules, or mini-circles that can't pack side by side, indicating further similarities with bulk DNA condensation by multivalent ions.[101] Images of a flatter region show the DNA structure much more clearly. FIG. 14C shows a region of dsDNA in which the repeat of the double helix is quite clear (arrows and note the 3.4 nm feature in the Fourier transform, inset). The lateral packing distance, as evaluated by the Fourier transform perpendicular to the long axis is about 2.5 nm. When an ssDNA is used, the images are quite different, as shown in FIG. 14D. There is no evidence of periodic structure along the chain direction (at this resolution) and the lateral spacing falls to about 1 nm (see the Fourier transform inset). It can be seen from these results that DNA can be imaged with an STM on this surface, and thus, that "good electrical contacts" are made by the phosphate-guanidinium H-bonds. The specific role of guanidinium can be verified using an amine-functionalized gold surface (of similar charge density to the guanidinium surface) as a control. The formation of matched hydrogen bonds is a key factor in enhanced electron transport.

Reading Base Composition from Adsorbed DNA

FIGS. 15A-15D show examples of current-distance curves obtained over DNA adlayers on top of guanidinium in tris-HCl buffer. These curves show current-decay curves obtained with a bare (green trace 151) or functionalized tip over various guanidinium surfaces. FIG. 15A: a guanidinium-functionalized surface (G-tip, pink traces 152); FIG. 15B: an oligo-T (T45) adsorbed onto the guanidinium surface (C-tip, pink traces 153); FIG. 15C; an oligo-T (T45)

adsorbed onto the guanidinium surface (G-tip, orange traces 154); FIG. 15D: an oligo-C (C45) adsorbed onto the guanidinium surface (G-tip, black traces 155). Data were obtained in Tris-HCl with a pH of 6.8. It can be seen thorn FIGS. 15A-15D that hydrogen bond mediated tunnel current is capable of generating high level signals (corresponding to a conductance on the order of 1 nS) that yield single-base recognition sisals of high fidelity and contrast. Thus, one may likewise expect tunnel conductance of a metal-linker-guanidinium-ssDNA-base reader-metal sandwich that is on the order of 1 nS. This can provide signals compatible with CMOS (the semiconductor technology used in most integrated circuits) readout. Interestingly, the C-T mismatches produce less signal in these conditions than they did in measurements made on nucleosides.[90]

Theoretical Confirmation of Experimental Results

One simple approach for calculating tunnel-conductance for a complex system is to make an infinite chain of repeating elements and use the methods of electronic bandstructure developed for solid state physics. The usual output of bandstructure calculations is a plot of energy vs. wavevector of the electrons, but, by solving for complex wavevectors (which correspond to tunnel decay outside of the allowed bands) the electronic decay constant, $\beta$, can be estimated from the maximum value of this complex wavevector along the lines that connect allowed states. This is called the method of complex bandstructure.[57]

Figure 16A:
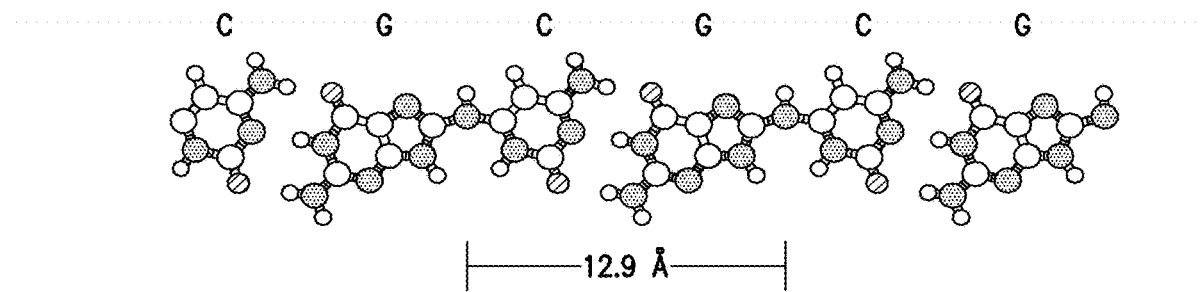
FIGS. 16A-16C: Complex bandstructure estimate of the electronic decay length, $\beta$, for G-C basepairs.

FIG. 16A shows a portion of an infinite polymer of G-C basepairs connected by Watson-Crick H-bonds formed by joining (in a computer) C and G bases with a nitrogen atom. The length of the "unit cell" in this polymer was 12.9 Å.

Figures 16B, 16C:
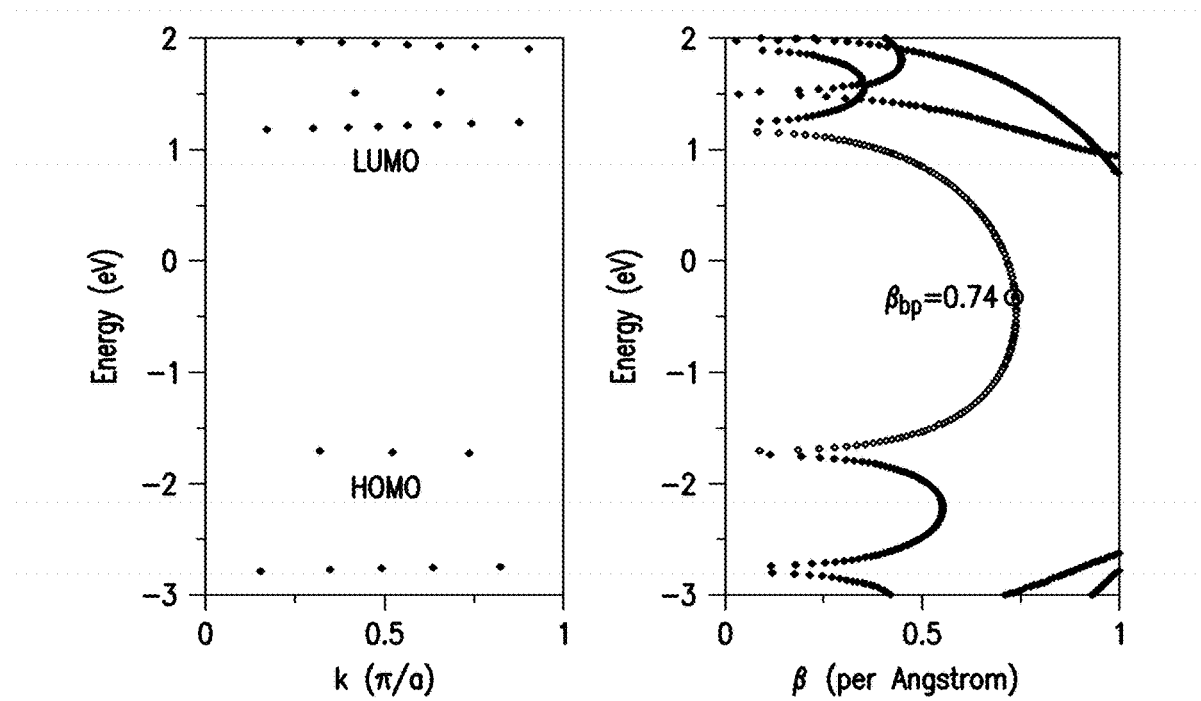

FIG. 16B shows a plot of the allowed energy levels for this polymer, pursuant to using a plane wave basis to solve for the electronic structure of this base-pair. The allowed energy levels appear as flat lines (not dependent on k) because the states are highly localized in this molecular system. The midpoint between the highest molecular orbital (HOMO) and the lowest unoccupied molecular orbital (LUMO) is the most likely energy at which the electrons would be injected from a metal contact (the Fermi level).

FIG. 16C shows curves representative of the complex (forbidden) states for which the transport must be by tunneling, using the same simulation. The semi-elliptical curve (red in the figure) connecting the HOMO and LUMO is the most penetrating state and the maximum value of $\beta$ is 0.74 $\text{Å}^{-1}$. This means the transmission probability through a single molecular unit (a cytosine-guanine base-pair connected by a nitrogen) is $e^{-\beta L}=e^{-0.74 \times 12.9}=e^{-9.5}$. A simple estimate for the conductance, Q of the cytosine-guanine basepair is $G \approx G_0 \, e^{-\beta L}=77 \, \mu S \times e^{-9.5}=5.5$ nS, where $G_0$ is the quantum of conductance. Thus the theoretical estimate of the conductance of a base-pair is of the same order of magnitude as the conductances used to obtain experimental data. These data illustrate that, despite being thought of as "weak bonds," the average electronic overlap near the HOMO-LUMO gap including H-bonds can be quite strong. The average is as strong as a sigma bond in terms of electron transport (though a sigma bond is, of course, a much stronger bond in terms of bond energy).

Generation of Molecular Recognition Signals in a Tunnel Gap Fabricated on a Chip; Optimization of Electrode Design and Fabrication The problem of how to make 'molecular alligator clips' has consumed the molecular electronics community for decades.[104-106] The problem now appears to have been solved in flexible junctions (like the STM where one electrode is controlled with sub Å precision)[107] but it is extremely difficult for fixed junctions, at least in the case of single molecules. One reason is that the outermost atoms of each electrode must be in precisely the correct position to satisfy the bonding requirements of the molecule that spans the gap. Some successful experiments have been reported[108-111] using electromigration, a technique in which a nanogap is formed by "blowing" a fuse consisting of nano-scale neck in a wire. But the same technique has been shown to mimic molecular electronic effects in the absence of molecules owing to the presence of complex metal structures in the gap.[112] The requirements for atomic precision in bonding molecules are mitigated in the embodiment of FIG. 1 because of the use of flexible linkers as part of the tunnel junction. This is possible because the embodiment of FIG. 1 depends on a binary "signal-no signal" output rather than on an absolute conductance of the gap. Thus, reliable manufacture of "clean" gaps of about 2 to 3 nm in size range and chemical functionalization of these gaps for reliable readout, are both realizable.

Figure 17A:
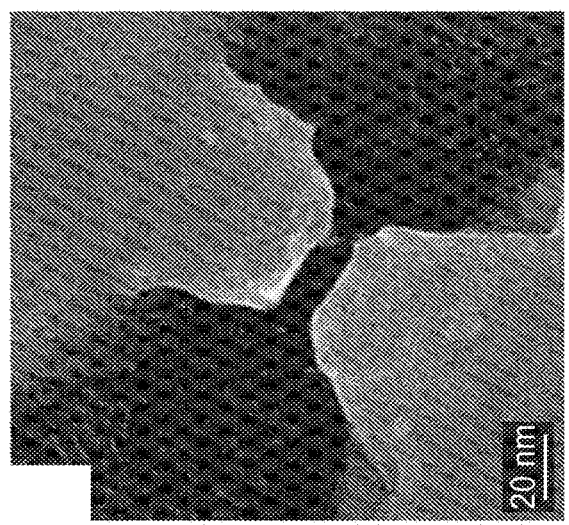
FIGS. 17A-17B.
Figure 17B:
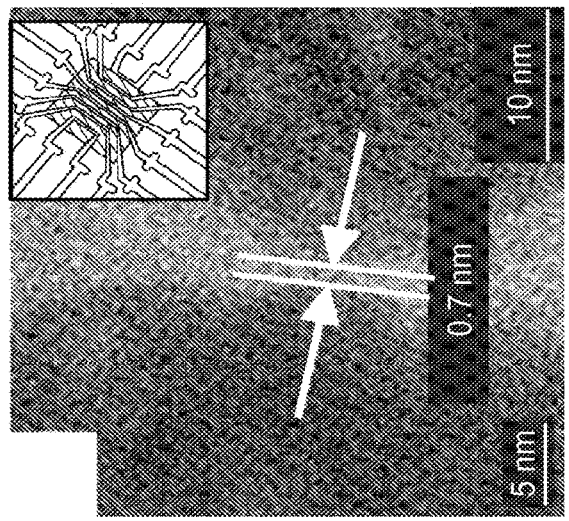
Figure 18A:
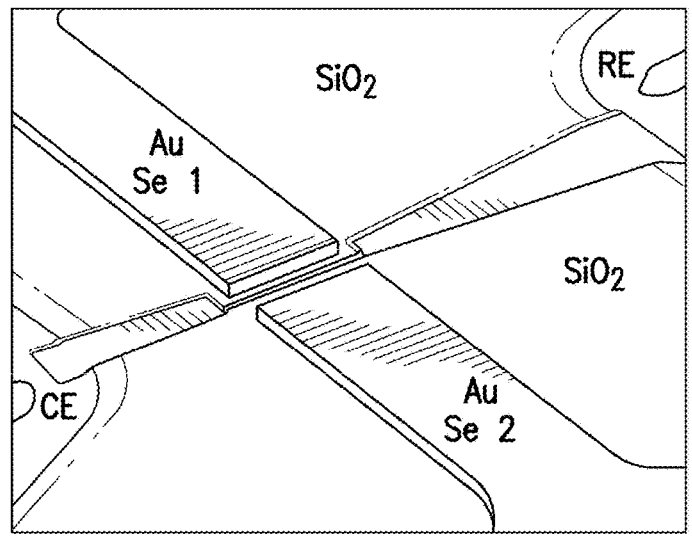
FIGS. 18A-18D: Testbed nanogap made by lithography and FIB.
Figure 18B:
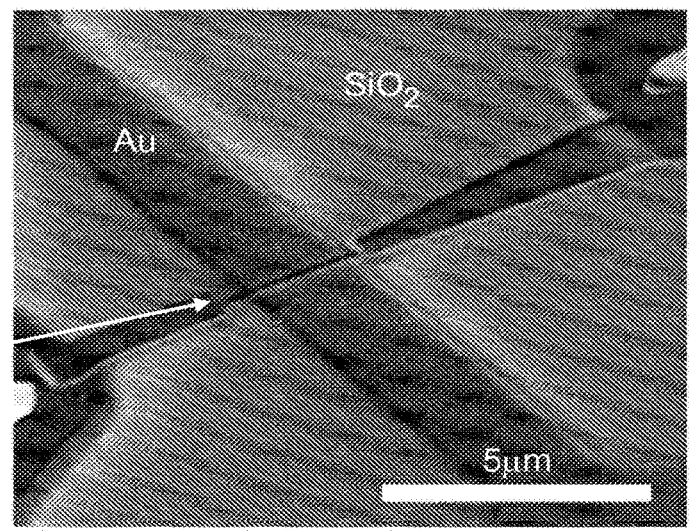
Figure 18C:
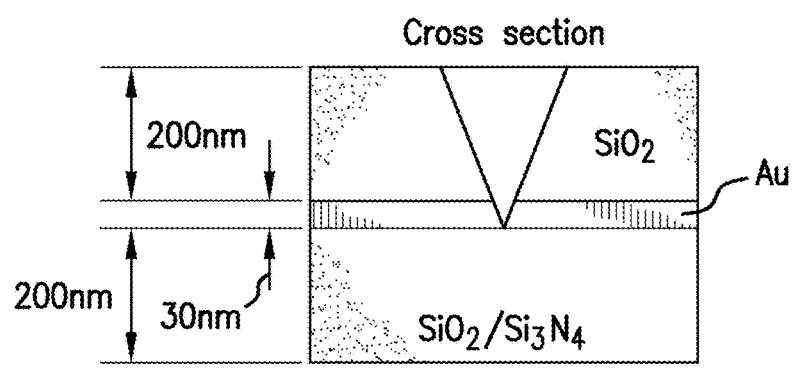
Figure 18D:
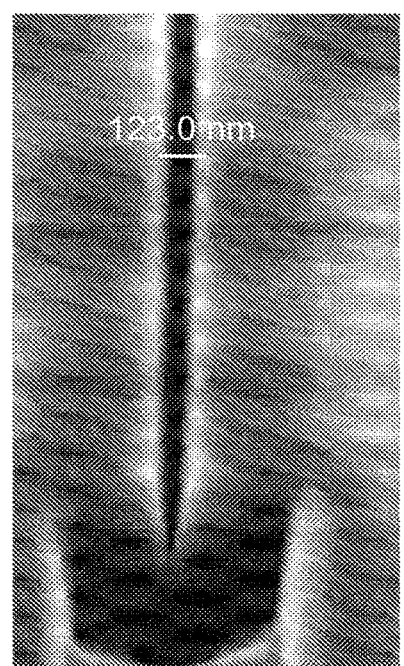

FIGS. 17A-B shows the results of one prior art approach to electrode design and the formation of gaps between electrodes. The technology employed to manufacture and inspect such "clean gaps" has undertaken a significant leap as a result of the work of Marija Drndić at the University of Pennsylvania. By using electrodes placed on very thin membranes (exactly as required for nanopores) Drndić's group has been able to image junctions using transmission electron microscopy (TEM) to atomic precision.[113] Moreover, Drndić's group has shown that the lack of electron backscatter in thin-film supports permits very high resolution electron-beam ablation of metal structures.[114]

Another approach to electrode design and the manufacture of nanogaps is electrochemical deposition and stripping. Electrochemical generation of nano-gaps has been in use for some years[115] but may sometimes be unreliable (see the supplementary material in He et al.[79]).

The present invention also takes advantage of a new approach to electrochemical generation. In one embodiment of the present invention, reference (RE) and counter (CE) electrodes are incorporated into the chip itself, spaced a few microns from the tunneling gap.

FIGS. 18A-18D shows a prototype testbed large-electrode junction (i.e., large electrodes, small gap) in accordance with one embodiment of the present invention. Gold electrodes that are 2 μm wide by 30 nm high are patterned by lift-off onto a 200 nm thick $SiO_2/Si_3N_4$ substrate in a cruciform pattern. One electrode is a continuous strip that is cut to form the two sensing electrodes (SE1, SE2), which also serve as the working electrodes for gold deposition and stripping. Two other electrodes (RE, CE) are separated from the central wire by gaps of 3 μm and they serve as built-in counter- and reference-electrodes. The electrodes are covered with a 200 nm thick layer of $SiO_2$. The wafer, containing 25 arrays, each of nine devices, is taken to the focused ion beam mill (FIB) where a trench is cut across the central wire to form the two sensing electrodes (SE1 and SE2). The trench is widened and continued out to the RE and CE electrodes to form microfluidic channels in communication with both, sensing electrodes and the CE and RE. As a consequence of the geometry of file ion-beam milling, a 100 nm wide trench at the top of the $SiO_2$ corresponds to about one to two nm gap in the gold electrodes. As a result, once the gap is chemically-cleaned of excess Ga ions, stable and somewhat reproducible tunnel gaps are formed.

Figure 19A:
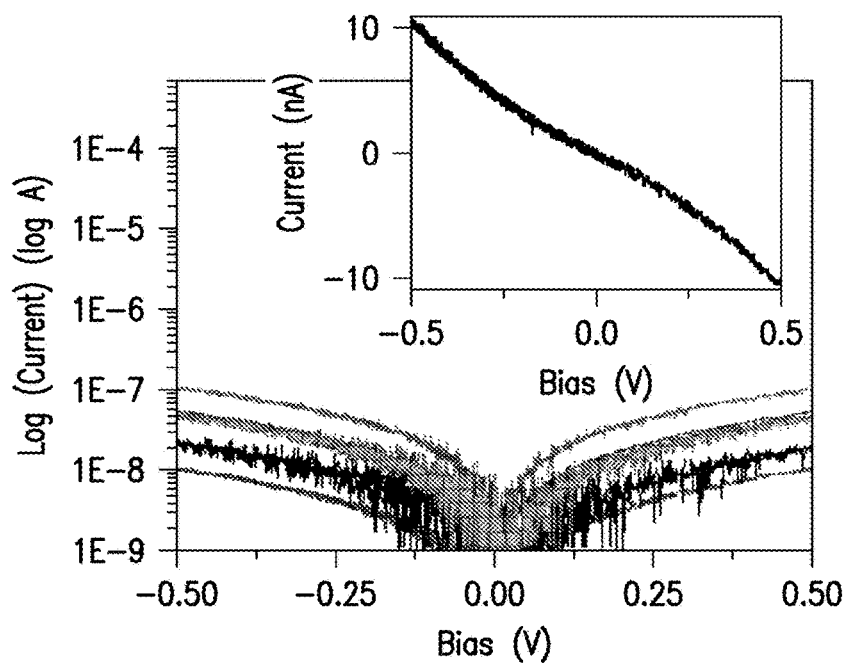
FIGS. 19A-19B: (19A) i-v plots for tunnel devices (as-made) similar to that shown in FIG. 18. (19B) Current vs. time after closing the gaps electrochemically and then stripping them open. Quantum-conductance steps (indicated by arrows) are clearly observed as Au is removed.

FIG. 19A, which plots the log-current vs. bias voltage data (and the linear data shown in the inset), confirms the presence of such tunnel gaps. Fits of these data to the Simmons formula[116] yield gap dimensions that are on the order of one nm. By placing a drop of gold-plating solution in the gap and controlling the deposition galvanostatically, while monitoring the tunnel current, $I_t$, it is possible to close the gap. Once closed (as detected by current between SE1 and SE2) controlled stripping opens the gap with atomic scale control.

Figure 19B:
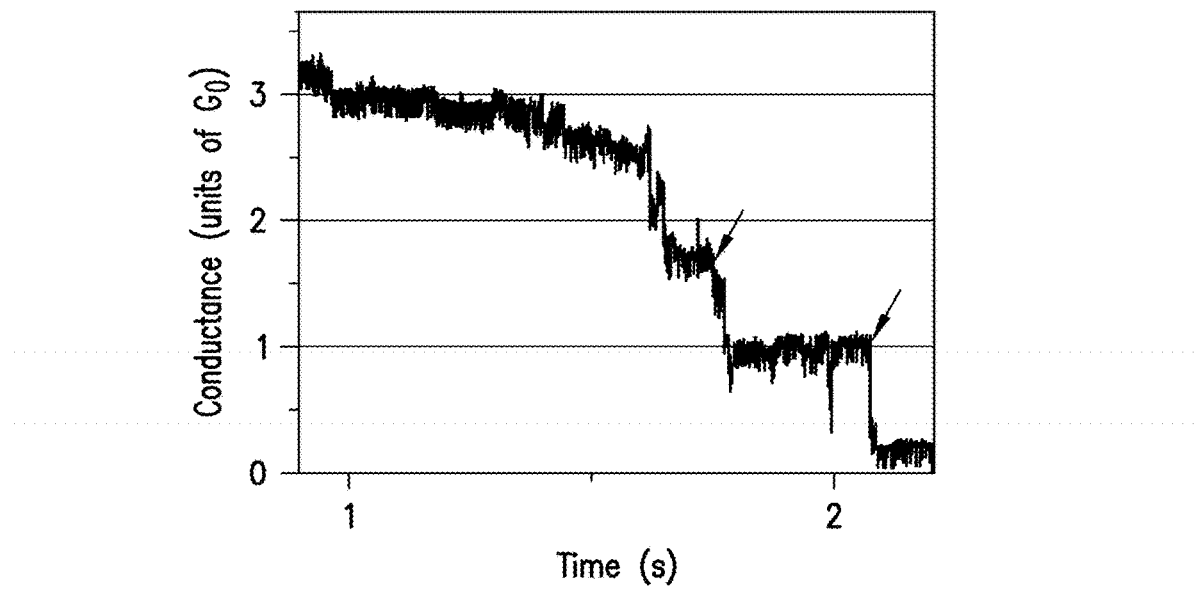

FIG. 19BB, which plots conductance as a function of time after the gaps are closed, shows quantum steps in conductance (indicated by arrows) that characterize atom-sized filaments of gold.[117] Thus atomic-scale control of gap size can be achieved by electrochemical deposition and stripping.

Manufacture and testing of nm wide tunnel gaps. Using electron ablation and TEM imaging on a 100 nm thick $Si_3N_4$ substrate (c.f. FIGS. 17A-17B) one may sculpt nm-wide tunnel gaps, correlating gap geometry with measured tunnel-current response. Optimal gap size for recognition (ca 2 nm to 3 nm) as measured by reproducible electrical characteristics and chemical response (see below) may thus be achieved.

Testing of gaps for recognition response. Gaps can be functionalized, in the first instance, by exposure to an equimolar solution of the guanidiniumthiolate and a mercapto-base. After rinsing, recognition can be tested by exposing the junctions to dilute solutions of nucleoside monophosphates and DNA dimers. The goal is to get current signals that track the STM data, i.e., the biggest signals occurring when Watson-Crick complementary nucleoside monophosphates are injected into the gap, smaller signals for mismatches and no signals at all for non-hydrogen bonding nucleoside monophosphate analogs. In the event that just one part of the gap dominates the tunneling (the desired result) each type of interaction should be characterized by a somewhat reproducible tunnel current. Though such testing is not the direct equivalent of the STM or nanopore geometry, the lifetime of the hydrogen bonding states generally correlate with bond stabilization energy $$\left(\propto \exp\frac{\Delta G}{k_B T}\right)$$

so that the two sets of signals should correlate well. Electrode design may be refined based on these data until the geometry is optimized. Molecular-recognition signals from the "macro-scale" testbed (FIG. 18) establish that the foregoing is achievable, even though the signals are difficult to interpret because many asperities contribute to tunneling.

Optimization of electrode functionalization. As seen in FIG. 1, the guanidinium phosphate-binder is formed on a first electrode and a base-reader is formed on the opposite, second electrode. The electric field in the gap is very large, so nucleotides may be drawn into the gap and oriented. Accordingly, one may compare the signals obtained from specifically functionalized electrodes (guanidinium on one, base reader on the other) with those obtained from electrodes randomly functionalized with a mixture of guanidinium and base-reader. Specific functionalization of nanoelectrodes has been demonstrated by adsorbing thiolates from an electrolyte with the electrodes held under potential control, relying on the reductive cleavage of the Au—S bond at −1V vs. Ag/AgCl to prevent adsorption onto one of the electrodes.[118] After rinsing, the previously uncovered electrode is functionalized with a solution of the second reagent.[118] In these experiments, one would expect to see signals at much lower concentrations of nucleoside monophosphate if the specific functionalization minimizes trapping of the target nucleoside monophosphate on one electrode or the other. Given the dielectrophoretic trapping capability of the gaps, one may obtain statistical signals even down to dilutions estimated to contain only one nucleoside monophosphate.

Optimization of electrochemical fabrication of electrodes. A method for electrochemical growth-assisted formation of electrode pains can be developed. Such a method may be automated and suitable for on-chip regeneration of the gaps. Lithographically defined electrode pairs on a 100 nm $Si_3N_4$ substrate may be used as a starting point. The electrode may then be used to assess electrode growth and stripping as a function of the electrochemical parameters (concentration, overpotential, starting electrode geometry, deposition and stripping times). TEM images may be used to analyze the resultant growth at close to atomic scale (c.f. FIG. 17A), and these results may be compared with predictions of simulations. Quantitative agreement between simulation and experiment validates the tools to be used in overall device formation.

Characterization of electrode stability. Reproducibility of the current-distance data indicates that the instability of gold-thiol connections, as manifested in an electronic "blinking" phenomenon[71] is not a problem on a pointed electrode. However, the long-term stability of fixed nanojunctions may still pose problems. While the on-off times for the H-bonded nucleoside monophosphates are on the order of milliseconds, "contact blinking" may be marked by loss and return of signals on a time scale of tens of seconds or more.[71] Such blinking, if it occurs, is not fatal, but does need to be figured into the calculation of the required reading redundancy.

Active control of the tunnel gap. Atomic scale control of the initial construction of the gap is necessary, as is atomic scale stability over long timescales. To help achieve the latter, active control of the tunnel gap may be implemented. This effectively mimics a scanning tunneling microscope on a chip. One scheme for fine gap control comes from an apparatus originally designed for controlled breaking of metal junctions ("break junctions"), and this may be used as a way of controlling a pre-fabricated gap.

Figure 20A:
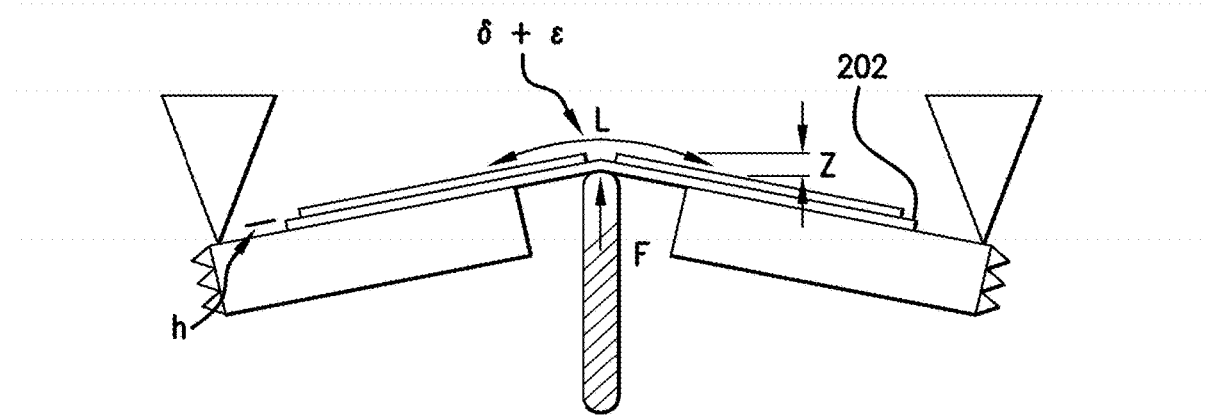
FIG. 20A-B: (20A) Electrodes on $Si_3N_4$ membrane incorporated into a break-junction apparatus (not to scale with some dimensions exaggerated). This version is for trial gaps without a nanopore. (20B) A buckling geometry that might prove suitable for use with a nanopore (buckling exaggerated).

FIG. 20A schematically illustrates such an apparatus 200 for line gap control. If a (originally flat) membrane 202, of thickness (h), width (w) and length (L), is subject to a point force (F) at its middle, two points on the upper surface move apart by an amount e owing to the induced curvature of the surface. Analysis of bending moments yields the following result:[119]

$$\varepsilon = \frac{3FL^2}{4Ewh^2}$$

where E is the Young's modulus of the material ($1.5 \times 10^{11}$ $N/m^2$ for $Si_3N_4$). In one embodiment, the target gap size, S, is likely be no more than 5 nm. With h=100 nm, L=w=5 mm, a 10% adjustment of δ ($\varepsilon$=0.5 nm) would require a force of 200 pN. Using the standard equation for a cantilever spring[120] shows that a motion (Z on FIG. 20A) of just 15μ would be adequate to achieve this. These parameters are compatible with MEMS fabrication processes, so that adjustable gaps could be mass-produced eventually. Adjustment of the electrochemical gaps in the present device may be accomplished by building a "break junction" like apparatus, comparing the measurements of the gap based on tunnel current to the predictions of finite element elastic analysis of the junctions. The data obtained from this exercise can be used to design a system integrated onto a chip using standard MEMS procedures.

Figure 2:
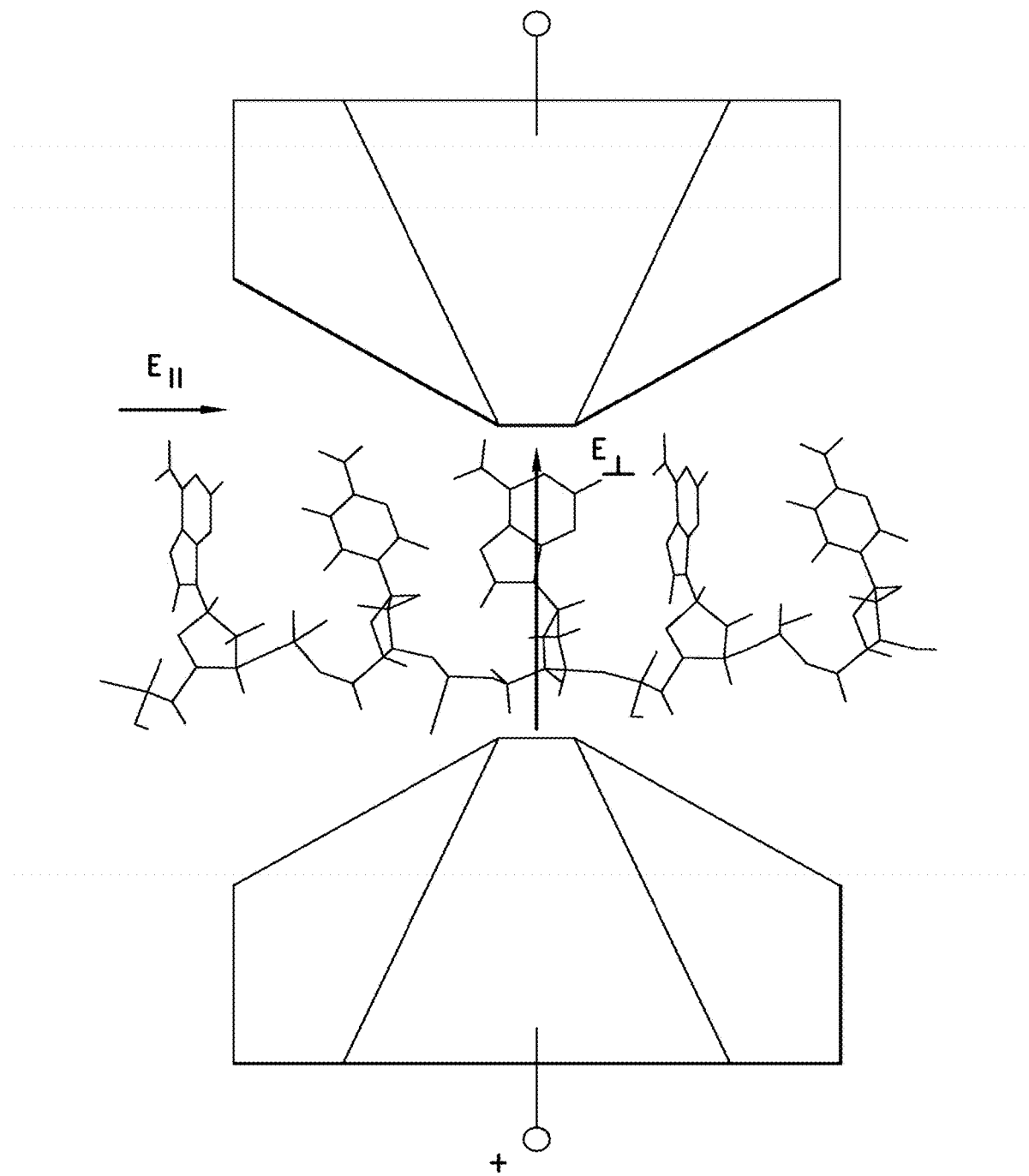
FIG. 2: Proposed tunnel current readout system (From the review by Zwolak and Di Ventra, 2007).
Figure 3A:
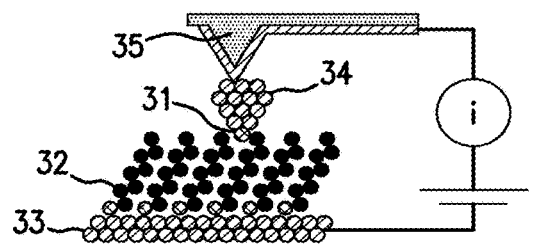
FIGS. 3A-3D.
Figure 3B:
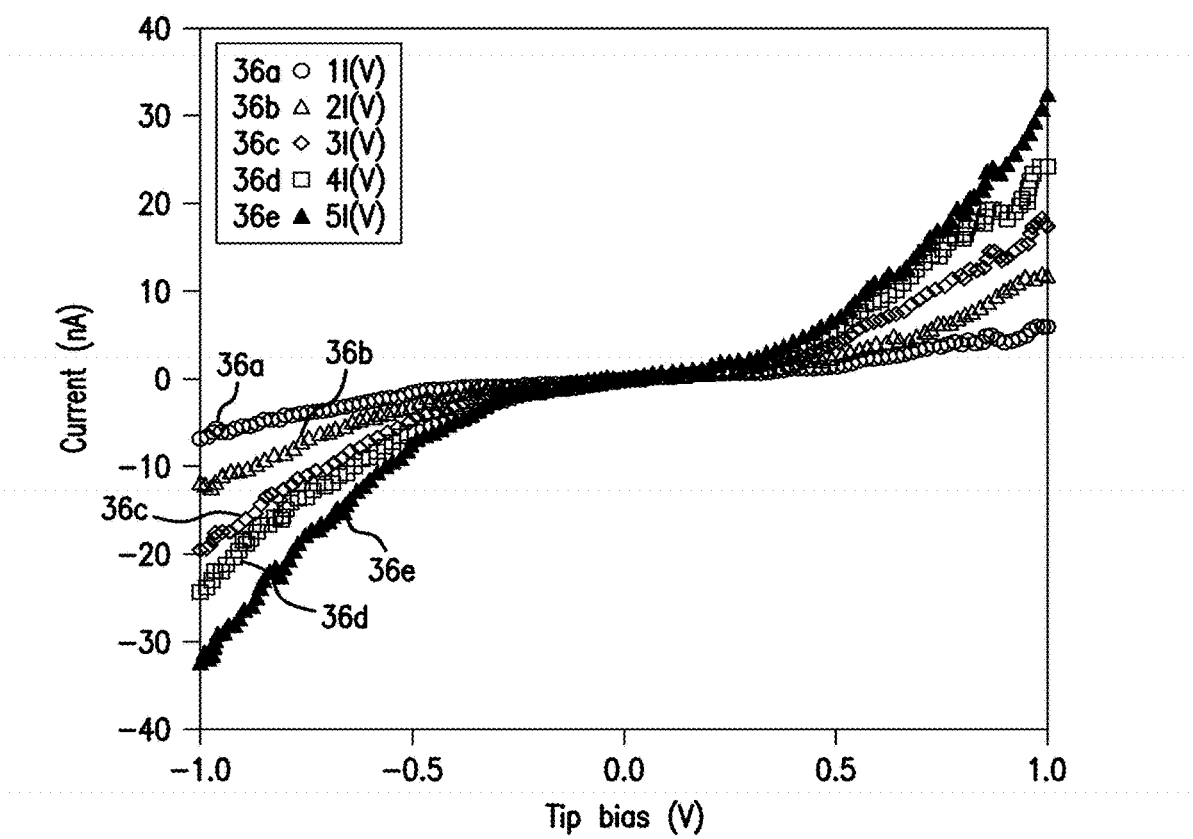
Figure 3C:
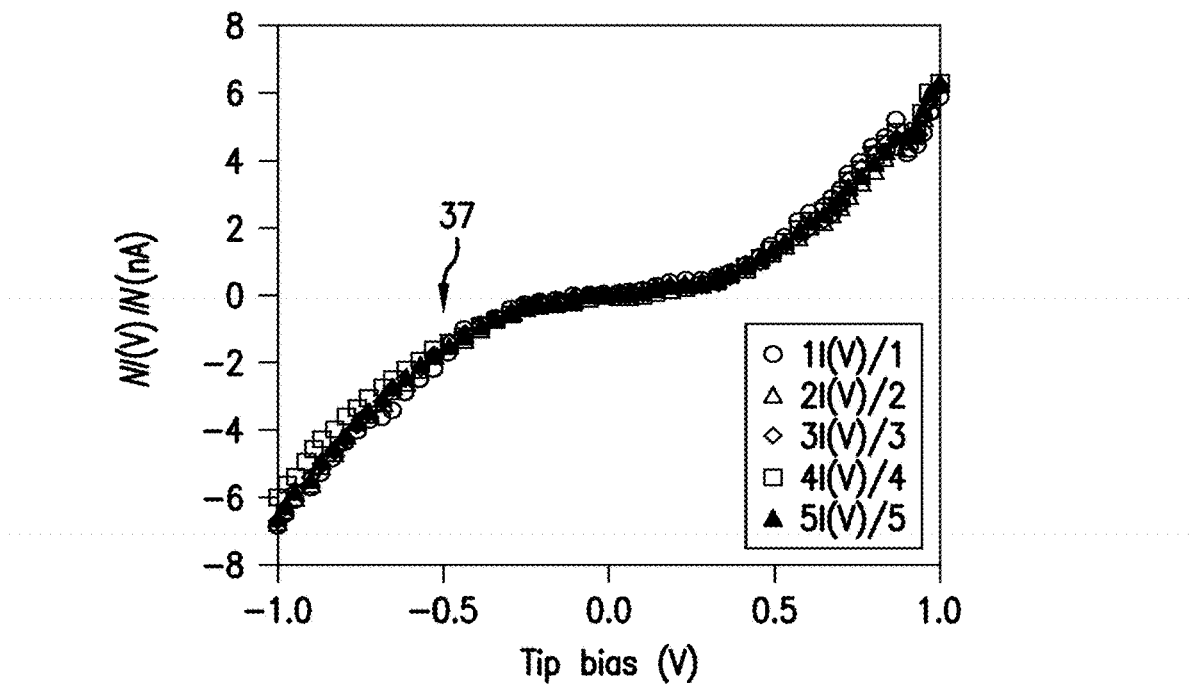
Figure 3D:
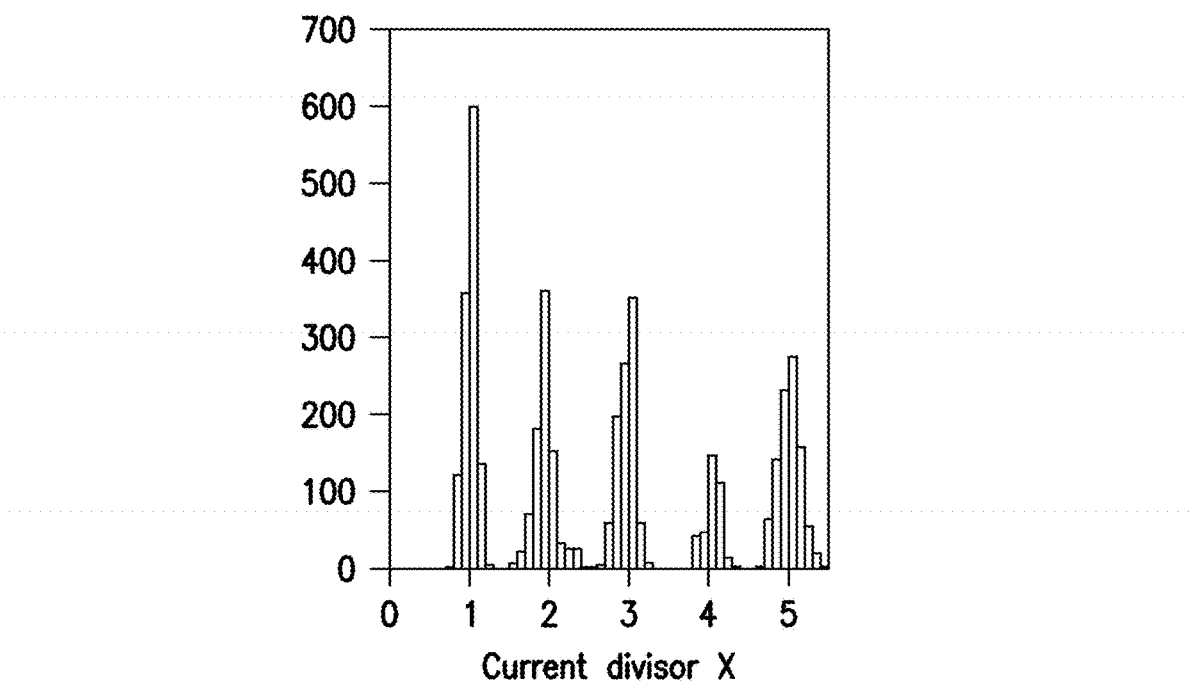

FIG. 2B shows a buckling geometry that may be implemented to actively control a gap that incorporates a nanopore 208, such as one that connects cis and trans fluid chambers.

Alignment of a Nanogap Electrode Pair with a Nanopore.

Overview: Assembly and alignment of the reading head, comprising a pore and electrodes can be achieved through electrochemical self-assembly of electrode pairs. Electrochemical deposition of electrodes minimizes the number of one-off nanofabrication steps, resulting in devices that are easier to manufacture. Furthermore an electrochemical approach makes it possible to strip and reuse electrodes, a possible cure for failure modes related to electrode geometry and functionalization. This also reduces costs and enhances reliability.

Figure 21:
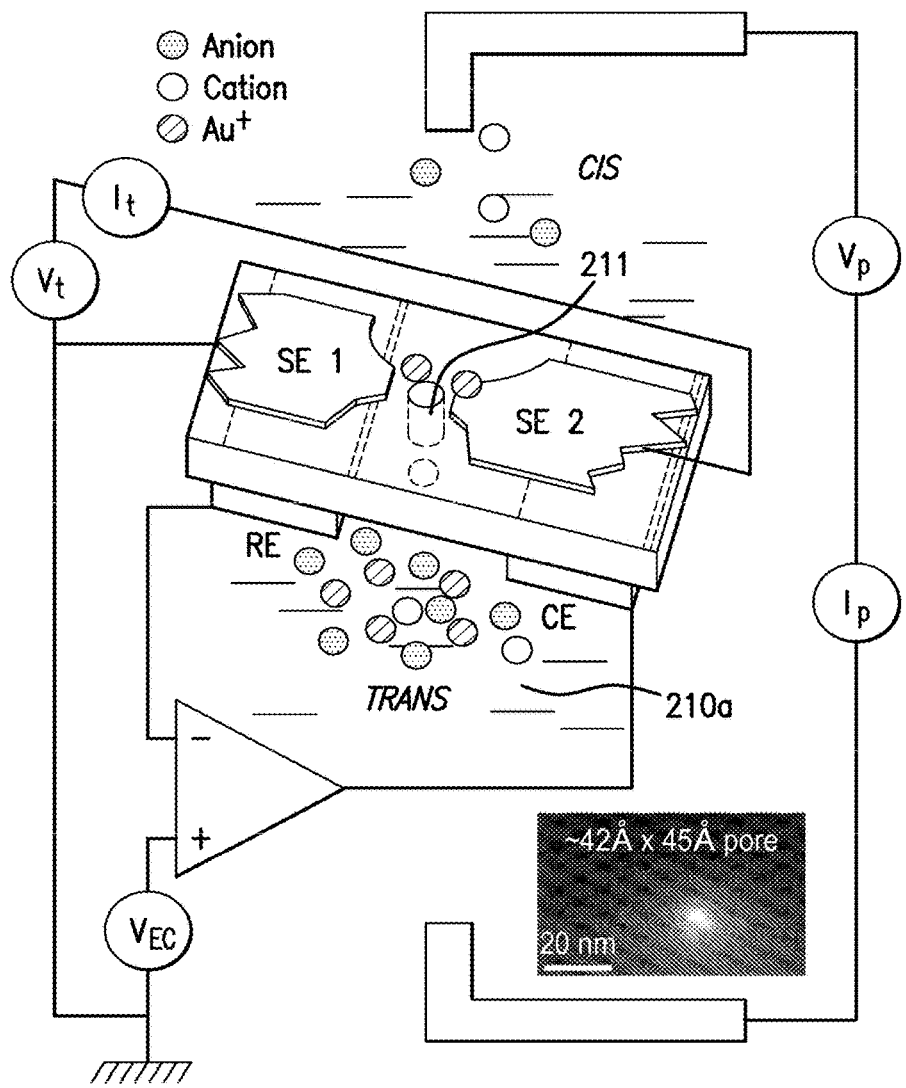
FIG. 21: Scheme for through-pore plating (showing a nanopore made by TEM shrinkage as an inset, lower right). The key feature is through-pore transport of $Au^+$ ions, localizing deposition to parts of the sensing electrodes (SE1, SE2) in close proximity to the pore. Metal deposition and stripping is controlled by the built in counter electrode (CE) using the built-in reference (RE) with the sensing electrodes serving as working electrodes (operated at a small potential difference, $V_t$). $V_{EC}$ sets the potential of the working electrodes. Measurements of pore current ($I_P$) and tunnel-current between the two working electrodes ($I_t$) is used as control parameters for final pore size and tunnel-gap size. The two data sets together can be used to center the electrodes in the pore.

FIG. 21 presents a strategy for controlled growth of electrodes into the gap, in accordance with one embodiment of the present invention. The deposition process is controlled from the trans solution 210a compartment so that deposition is localized to the region in the immediate vicinity of the pore 211. In addition to the electrode starting geometry (optimized in specific aim 1), other factors affecting this process are reagent concentrations, electrode potentials and pore geometry. The process is complicated by the high resistance of the pore. Simulations and TEM measurements can be used to characterize real junctions to optimize the process of forming the electrodes. Mellers TEM approach[33] can be advantageously employed to produce small pores, but it may also be possible to eliminate the TEM "filling" step. While the electrode gap can be quite large, the nanopore 211 must be small enough to permit only one DNA strand to pass at a time. Therefore, alternatives to TEM could greatly simplify the production of reading heads. Recent reports of controlled formation of pore as small as 5 nm by FIB[121] indicate that one may start with a 20 nm pore cut into a 20 nm constriction to form the two sensing electrodes (the starting geometry shown in FIG. 22C). One can mill through a thin $Si_3N_4$ from beneath the electrodes (which are visible in the dual-beam FIB through the membrane). The gold electrodes can then be electroplated out into the gap, narrowing both the gap and the pore to the desired size (~2 to 3 nm). Optimizing pore size can be advantageous given that smaller pores result in greater DNA-pore interaction while distinct ssDNA translocations have been observed in rather large pores.[38] In the event that a small (<2 nm) pore is required to ensure translocation of only single strands, or to remove secondary structure, one may start with pores that have been "shrunk" on the TEM.[33]

Simulations. A computational approach can be used to simulate the electrochemical processes in three stages: (1) 2D modeling of the electrodeposition process ignoring double-layer effects. (2) Subsequent inclusion of double layer effects. (3) Finally, a full 3D model including the double layer.

2D modeling (no double layer). FIG. 22A shows one embodiment of a 2D model of the electrochemical system that can be used to identify proper values for the processing parameters such as the deposition potential and duration. The electrodeposition process occurs via the reduction of Au+ ions at the surfaces of the two sensing electrodes (SE1 222a and SE2 222b) held at potentials V1 and V2. These must differ by at least 50 mV for tunneling to be detected, but this sensing potential could be switched during deposition if uneven growth is a problem. The reduction of Au+ (in the plating solution 226, e.g., KAu(CN)2) to Au causes a depletion of Au+ ions near the electrode surface, and this in turn builds up a concentration gradient driving more Au+ to the surface through the nanopore 224 by diffusion. Thus the electrodeposition is a process controlled by the reaction kinetics occurring at the electrodes and the mass transport of Au+ in the solution through the nanopore. To simulate this process, the combined problem of electrokinetic flow and electrodeposition can be considered based on the Butler-Volmer kinetic equation (which can take account of the irreversible kinetics generally observed at nanoelectrodes) and diffusive treatment of mass transport. The rate of Au deposition is defined as $dh/dWe*M_{Au}/d_{Au}/F$, where Je is the normal electron flux across the electrodes, $M_{Au}$ and $d_{Au}$ are the molecular weight and density of Au, respectively, and F is the Faraday constant. Running the electrokinetic flow mode with the "moving mesh" application in COMSOL Multiphysics, a finite-element based modeling software, can solve this modeling problem. This exercise provides initial values for the deposition potential and duration.

2D modeling of electrodeposition including double layer effects. The description of electrodeposition on the nanoscale requires explicit inclusion of the polarization that forms on the electrode surface in contact with the electrolyte (the electrical double layer, EDL). It has recently been reported that the EDL structure outside nanoscale electrodes (having a critical dimensional <100 nm) affects not only the electron transfer across the electrodes but also the ionic distribution in the solution.[122]

FIG. 22B shows a modification to the 2D model which includes the EDL structure outside the electrodes 222a, 222b. Because of the EDL, the Nemst-Planck equation can be used for the mass transport phenomena due to the combined diffusion and electromigration of Au+ ions. Furthermore, in the presence of the EDL, ionic electroneutrality does not hold inside the diffuse layer, thus an electrostatic problem governed by the Poisson equation can be solved at the same time. From this effort, proper values for the deposition potential and duration can be determined. Since the rate of Au deposition is related to the normal electron flux at the electrode surfaces and the normal flux is affected by the shape and curvature of the electrode surface, various types of surface shapes and curvatures for the electrodes may be considered to identify a proper electrode shape for achieving the best outcome for resizing the nanopore without occluding the nanopore, shorting the sensing electrodes in the electrodeposition process or having a gap height that is too thick to sense a single base (base-base separation is about 0.6 nm).

3D modeling of electrodeposition including the double layers. FIG. 22C shows a full 3D model of the deposition process. The foil 3D model evolves from the tools associated with the 2D model and thus produces an optimized set of process parameters including the electrodeposition potential, deposition duration, and surface shape for the electrodes in a 3D setting.

Figure 20B:
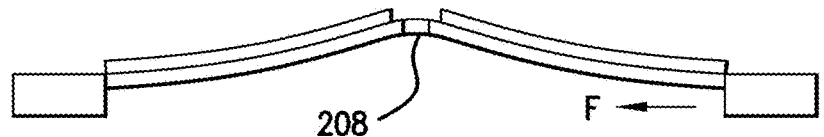

Gap optimization. The use of a thin $Si_3N_4$ support allow TEM examination of the gap, and independent monitoring of the orifice size and tunnel gap comes from measurements of the pore ion current and the tunnel current between sensing electrodes. The exact geometry may not be critical, provided that (a) the electrode height in the gap is <0.6 nm and (b) the widest passages through the structure are no more than 2 to 3 nm. The structure proves to be somewhat tolerant of local details because (1) the ionic current threads the DNA into the major part of the orifice, (2) the (flexibly) tethered guanidinium and base-reader orients the DNA by H-bonding. Devices can be tested both with nucleoside monophosphates and with homopolymers (for all bases bar oligo-G which is not well behaved). These tests determine whether or not one needs to apply active control to the gap. While active control of the gap is possible, it is complicated by the presence of both cis and trans solution chambers in place. FIG. 20b shows one candidate geometry (distortion greatly exaggerated) that one may implement, pending finite element mechanical analysis.

Design and Synthesis of DNA Base-Readers

Elimination or reduction of base-pairing mismatches simplifies the robustness of the sequencing. This can be realized by using more specific DNA Base-Readers. Better affinity elements based on chemical principles and theoretical modeling help with the design of recognition reagents. Once synthesized, affinity elements can be readily and rapidly characterized using STM methods, such as those described herein.[90]

Figure 23:
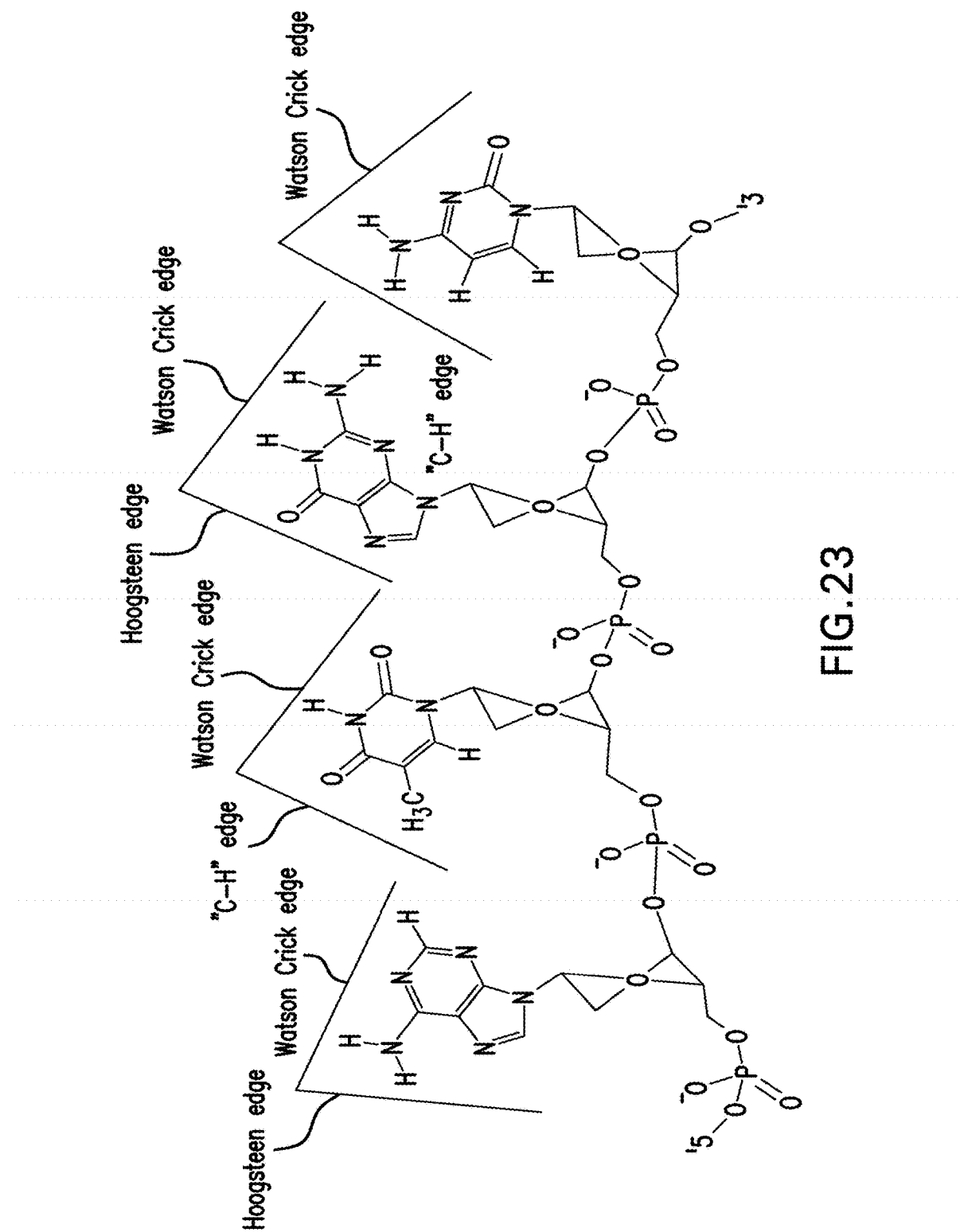
FIG. 23: Hydrogen bonding edges of DNA bases.

General Considerations. As shown in FIG. 23, each of the four bases has a distinguishable Watson-Crick edge, allowing one to design a reader for each of them. Four separate readers are likely to be required, although it may also be possible to employ a "universal reader" having a particular structure. A set of candidate structures can be screened to determine their specificity and immunity to mispairing. A DNA base reader should have the following chemical and structural features: (1) donor and acceptors sites for formation of stable hydrogen bonds; (2) planar n system capable of stacking interactions and efficient mediation of tunneling; (3) the molecules must be constructed such that the Watson-Crick base pairing occurs with high specificity; (4) they could incorporate steric obstruction of mismatches; and, (5) should be stable to oxygen, light, water, and electrochemical reactions, once coupled to the electrodes. It is best to reduce manipulations of the target DNA (such as incorporation of modified nucleotides by enzymes) to a minimum in view of the goal of reading long, native DNA.

Electronic structure calculations can be carried out prior to synthesis both to verify the proposed bonding, and to test the effects of altering the structure of the heterocyclic rings on electronic conductance.

The Adenine Reader (a Reader)

A commercially available 5-mercaptouracil may be used as a candidate Adenine reader. FIG. 24 shows that 5-mercaptouracil can form a Watson-Crick base pair with adenine, but it can also mispair with other DNA bases C, G, and T.[123] Because each of these mismatched base pairs has a similar hydrogen bonding pattern to the Watson-Crick base pair, it may be very difficult to distinguish them electronically, making adenine the most difficult base to identify unambiguously. This problem is not necessarily fatal if high fidelity data are available from the three other readers, but a selective A-reader is highly desirable.

Figure 25:
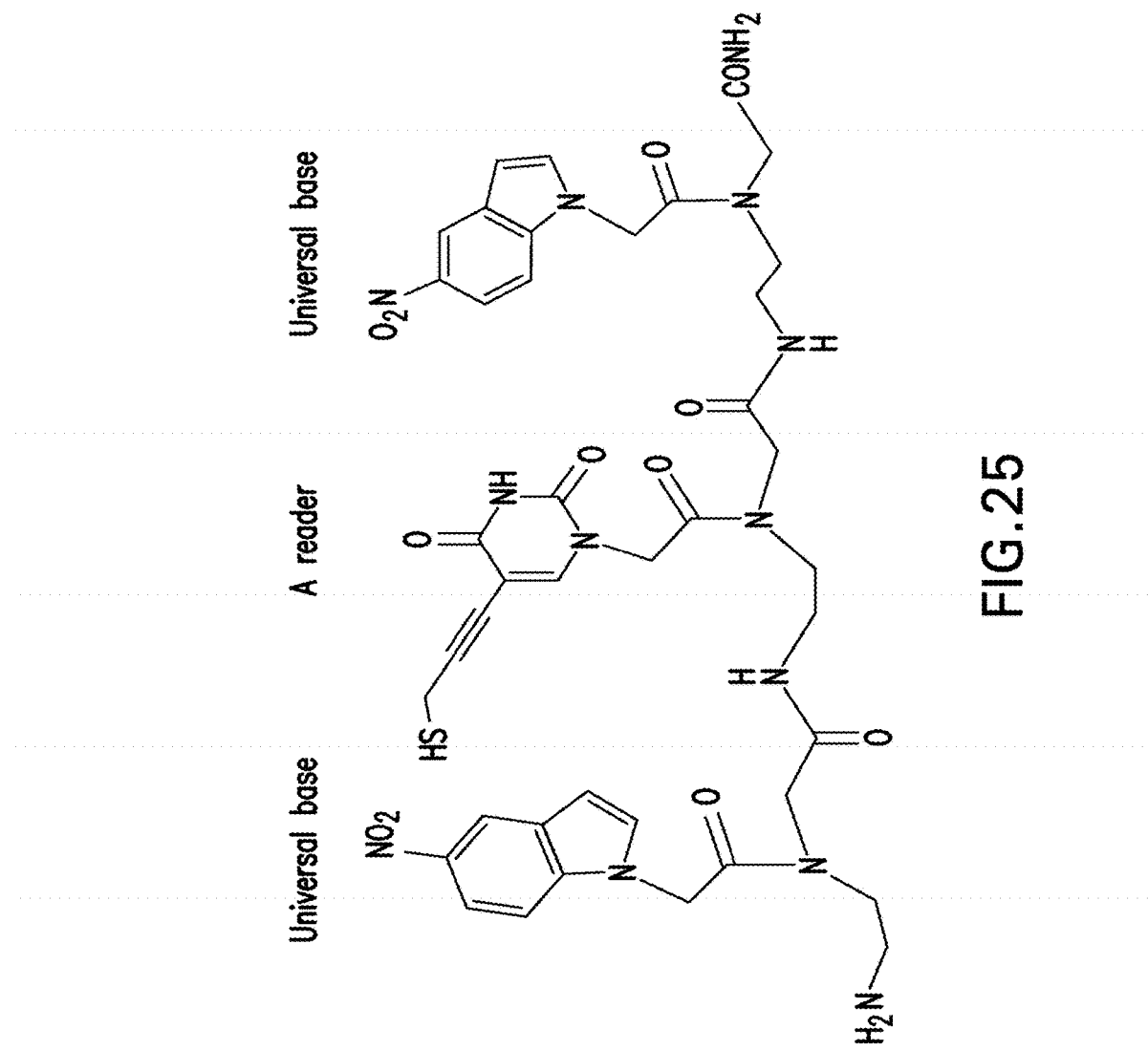
FIG. 25. Structure of a PNA trimer composed of modified uracil and universal bases.

FIG. 25 shows a peptide nucleic acid (PNA) trimer comprising one modified uracil flanked with universal bases, which may be synthesized. Such a PNA may serve as a selective A-reader. PNA is a structural mimic of DNA but it forms more stable DNA duplexes and is more sensitive to mismatches than its DNA counterpart[124] By using a PNA trimer for recognition, one may convert a single base pairing process into a DNA-PNA hybridization process. Thus, the base pairing specificity of modified uracil relies not only on hydrogen bonding but also on stacking with its nearest neighbors. The additional stacking interaction promotes the pre-organization of the base reader into the "right" conformation for Watson-Crick base pairing. Universal bases form base pairs with normal DNA bases indiscriminately[125] so the PNA trimer should have no selectivity to the (n−1) and (n+1) flanking bases on the target DNA. It has been demonstrated that a universal base can enhance the mismatch discrimination in the DNA duplex thermodynamically[126, 127] and enzymatically.[128] In one embodiment of the structure, a propargylthiol linker is attached at 5-position of uracil for connection to the electrode. In the event that this linker is not long enough, another "molecular wire" may be used. The PNA trimer can thus be tested against a series of adenine centered DNA trimers with varied base contexts at their two ends on gold substrates using the STM method.[90] Such a strategy may also be applied to the design of other base readers.

The PNA trimer can be synthesized manually or in an automated peptide synthesizer. The synthesis of universal base PNA monomer has been reported in the literature[129,130] The modified uracil PNA monomer may be synthesized starting from 5-iodouracil-1-acetic acid.[131] The starting material reacts with ethyl N-[2-Boc-aminoethyl]glycinate, providing a 5-iodouracil PNA monomer that can be converted into the desired product through the Sonogashira Coupling[132] with 3-benzoyithio-1-propyne followed by treating with di-tbutyl-1-(tbutylthio) hydrazine-1,2-dicarboxylate.[34]

The Cytosine Reader (C Reader)

Figure 26:
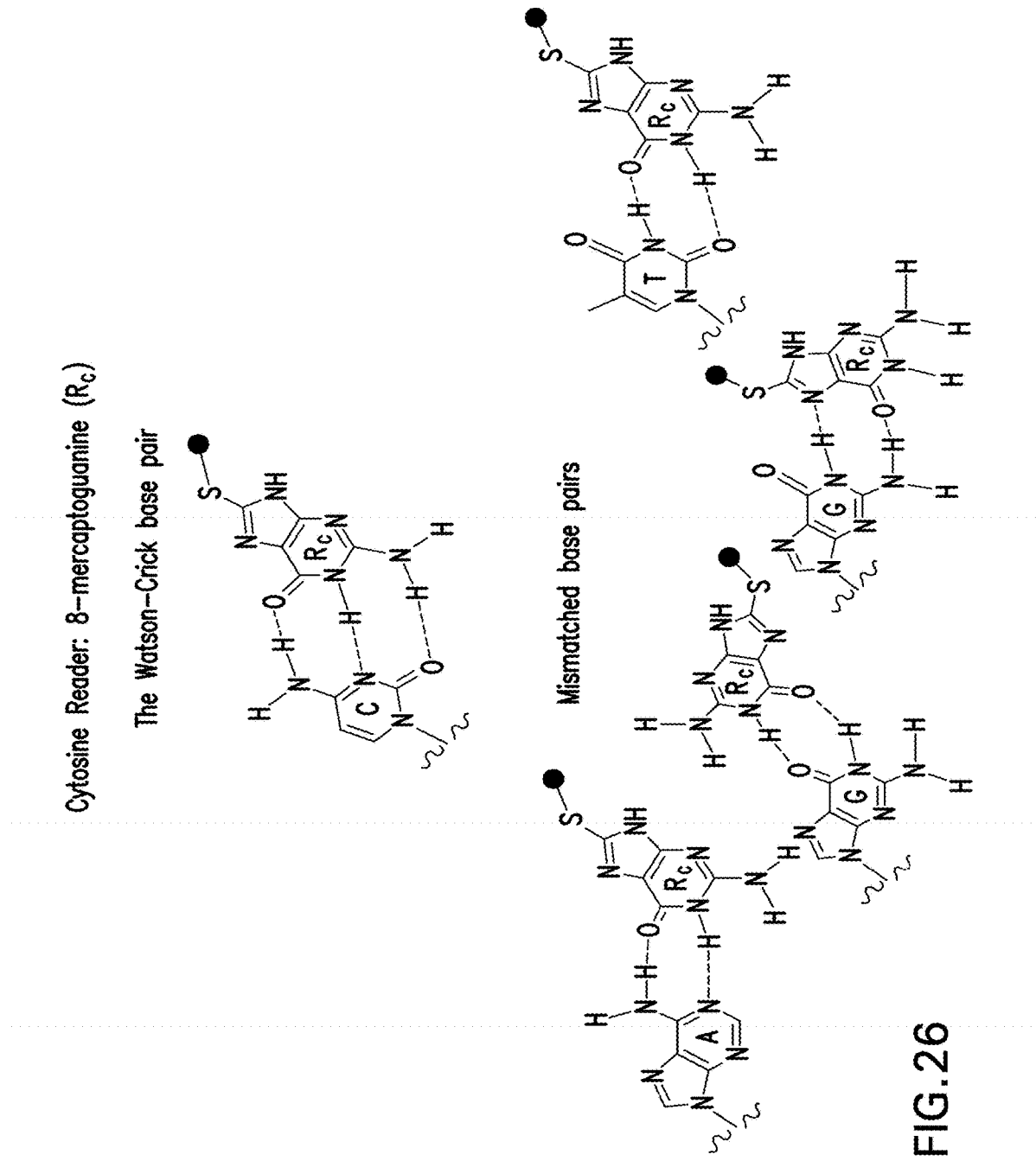
FIG. 26. Base pairing of the cytosine reader ($R_C$) with natural DNA bases.

FIG. 26 illustrates that though 8-Mercaptoguanine can serve as a C reader, guanine in general forms stable mismatched base pairs such as G-G, G-A, and G-T[99, 133, 134] Ideally, however, these mismatches would be reduced. Sekine and coworkers have demonstrated that 2-N-acetyl-3-deazaguanine (a2c3G) is more selective to cytosine than guanine (see FIG. 27), and also destabilizes the GA mismatch.[135] Compared to guanine, one of the undesired hydrogen bond acceptors is removed and the rotation of the $NH_2$ group is constrained in a2c3G.

Figure 27:
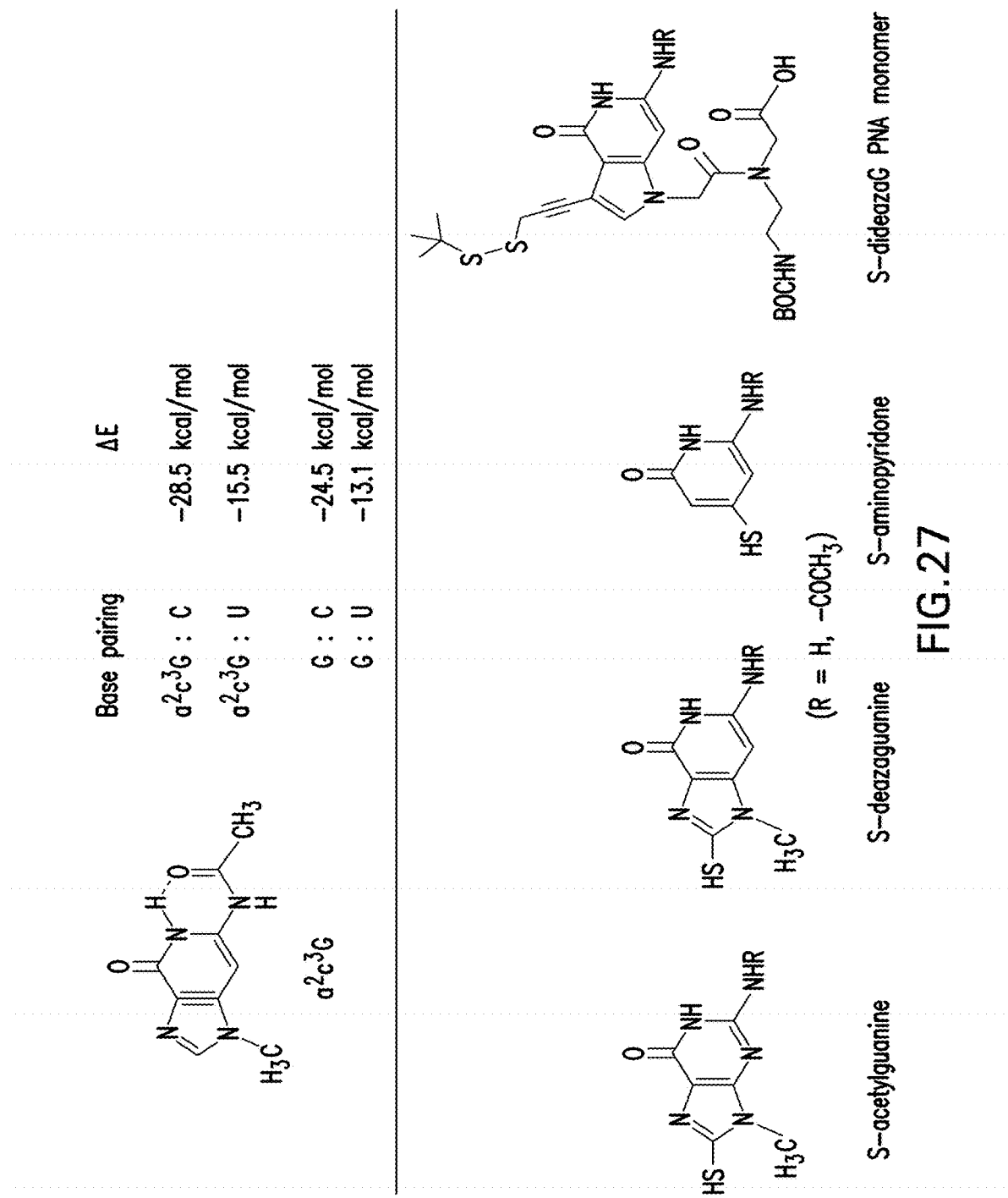
FIG. 27. Proposed structures of modified guanines for improving specificity of the C reader.

FIG. 27 shows a number of modified guanines which, based on the work of Sekine, may serve as C readers. A common feature of these molecules is that their Watson-Crick edge remains unchanged and the undesired atoms are left out. S-acetylguanine is an amine-acetylated derivative of 8-mercaptoguanine, which can be used to determine how acetylation of the amine affects the specificity of the guanine. With this control, S-deazaguanine, a deaza derivative of S-acetylguanine (with the 3-nitrogen removed) should reduce the sheared G-A mismatch.[136] S-aminopyridone is the simplest candidate C reader and it should have the highest specificity. A PNA trimer containing 3,7-dideazaguanine (S-deazaG) is potentially useful for this purpose as well.

S-acetylguanine can be synthesized starting from 9-methyl-8-mercaptoguanine.[137] The thiol group is first protected in a tbutyl disulfide form,34 and then the starting material treated with acetyl chloride[135] followed by Al—NiCl2-THF.[138] The synthesis of S-deazaguanine is straightforward using 3-deaza-9-methyl-guanine as the starting material. S-aminopyridone can be synthesized starting from 4-iododiamonopyridine prepared according to the reported procedure.[139] First, 4-iodo-6-acetylaminopyridone can then be synthesized by adopting the method used by Sun et al,[140] and then converted to the desired product by treatment with thiourea. The key step in synthesis of S-dideazaG PNA monomer is iodonation of didcazaguanine. The approach developed by Ramzeva and Seela[141] can be employed for this. If such an approach is found to have a selectivity problem, one may first prepare 7-iododidazaguanine using the regioselective reaction controlled by a bulky group at 9-position of dideazaguanine and then convert it to the desired product.

The Guanine Reader (G Reader)

Figure 28:
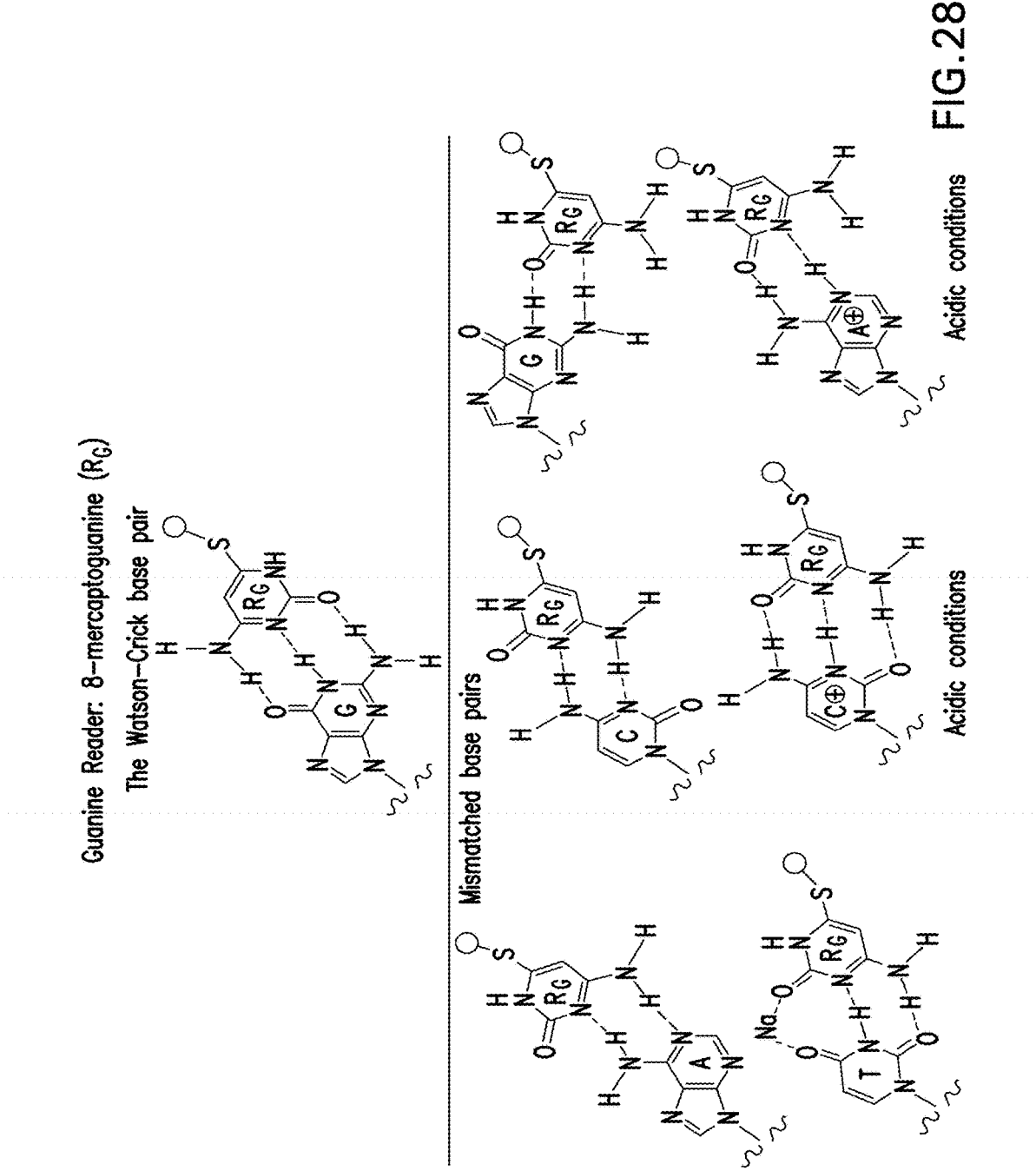
FIG. 28. Base pairing of the guanine reader ($R_G$) with natural DNA bases.

In one embodiment, 6-Mercaptocytosine, a cytosine derivative, can be used as a G reader. FIG. 28 shows that 6-Mercaptocytosine should form a more stable base pair with guanine compared to the mismatches in neutral conditions. Other candidates include 5-mercaptocytosine, 5-mercapto-1-methylcytosine, 6-mercapto-1-methylcytosine, and 1-(2-mercaptoethyl) cytosine, which can easily be synthesized from commercially available starting materials.[142] Studies of these molecules allow one to optimize the G reader attachment and to determine how the N-1 methylation of cytosine affects its specificity. The effects of pH on the recognition of the G reader should also be taken into consideration. It is known that protonation on DNA bases enhances the stability of mismatched base pairs. Under slightly acidic conditions. Cytosine forms stable hydrogen bonded base pairs with protonated cytosine (C+) and adenine (A+).[143, 144] The protonation alters the electronic structure of DNA base pairs, resulting in changes of their electronic properties.[145] Thus, pH is a factor in achieving a high specificity. The electrode side of the pore may be somewhat basic owing to the polarization of the pore used to translocate the DNA into the cis chamber.

Figure 29:
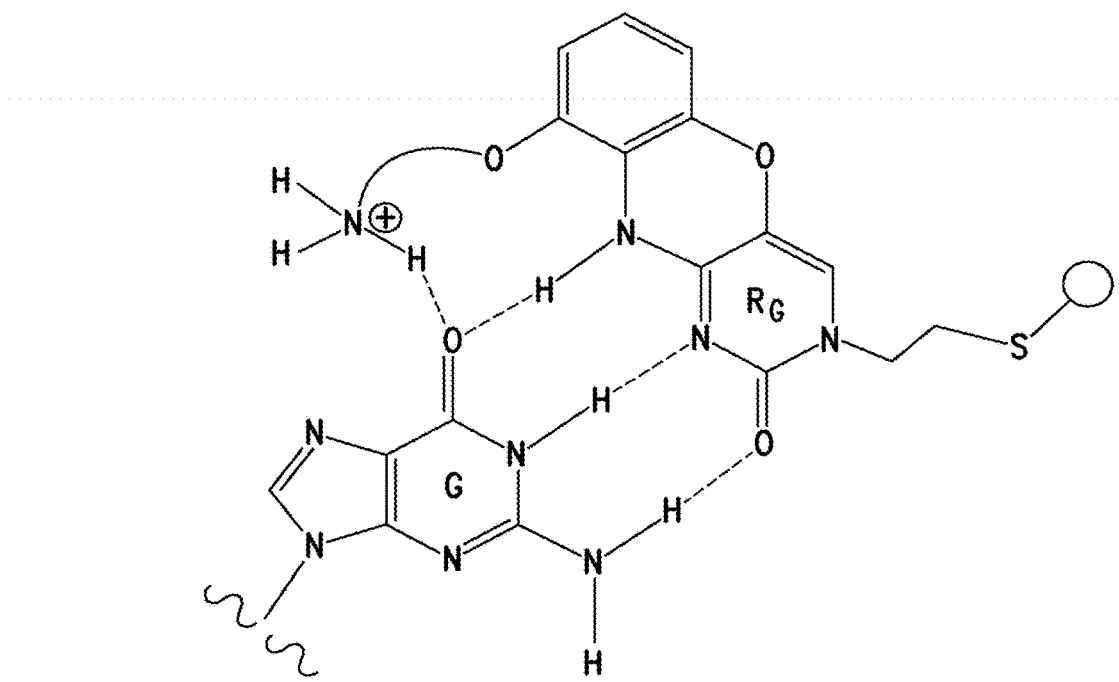
FIG. 29. Basepairing of the G-clamp with guanine.

FIG. 29 shows the basepairing of a tricyclic cytosine analogue (called a "G-clamp" with guanine. Lin and Mattecucci have reported that such a G-clamp can simultaneously recognize both Watson-Crick and Hoogsteen edges of a guanine when it was incorporated into DNA (FIG. 29).[146] The G-clamp has shown a higher specificity than its counterpart, 5-methylcytosine. The G-clamp may also be evaluated for its suitability as a G reader. A thiolated G clamp can be synthesized based on a procedure published by Gait and coworkers.[147]

The Thymine Reader (T Reader)

In one embodiment, 2-amino-8-mercaptoadenine, a derivative of 2-aminoadenine (DAP), can be used a T reader. FIG. 30 shows that DAP forms a more stable Watson-Crick base pair with thymine due to an additional N—H O hydrogen bond. However, it has been reported that stability of the DAP-T base is sequence dependent in DNA,[148] which is attributed to varied base-stacking interactions. Thus, a individual DAP coupled to an electrode should recognize thymines in a single stranded DNA with high selectivity, generating distinguishable electronic signals. DAP can form mismatched base pairs with C and A.[148, 149] Other types of mismatches, such as Hoogsteen base pairs, can also occur. As shown in FIG. 30, one may employ three analogues of diaminopurine to improve its specificity and affinity to the thymine base. 2,6-Diacetamido-4-mercaptopyridine, which can be synthesized by treating 2,6-diacetamido-4-iodopyridine[139] with sodium hydrosulfide, is a simple DAP analogue which is more specific and stable. In general, the DAP-T base pair is less stable than the G-C base pair.[150] Recently, Brown and coworkers reported an analogue of adenine, 7-aminopropargyl-7-deaza-2-aminoadenine, which could form an "A:T" base pair with stability comparable to G:C.[151] One may therefore test the base pairing specificity and stability of its analogues 7-deaza-2-aminoadenine and 3,7-dideaza-2-aminoadenine by incorporating them into the PNA trimer, respectively. The corresponding PNA monomers can be synthesized from commercially available starting materials 6-Chloro-7-deazaguanine and 4,6-dichloro-1H-pyrrolo[3,2-c]pyridine[152] using chemistries described above.

A Universal Reader

One may attempt a universal reader capable of recognizing the four natural DNA bases with distinguishable signatures. 4-(mercaptomethyl)-1H-imidazole-2-carboxamide is proposed as a candidate universal reader. It includes two hydrogen bonding donors and two hydrogen bonding acceptors, one half on the aromatic imidazole ring and the other half on the amide side group. The molecule can be attached to the electrode through the thiol group.

Figure 31:
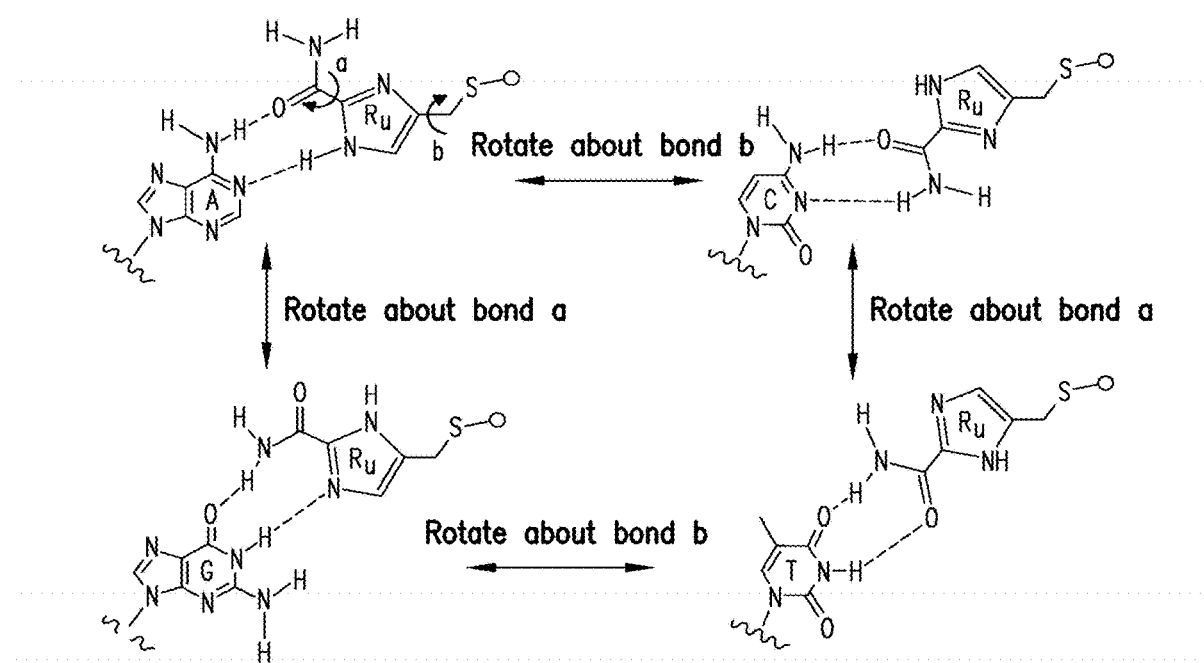
FIG. 31. A universal DNA base reader ($R_U$): hydrogen bonding schematic for 4-(mercaptomethyl)-1H-imidazole-2-carboxamide.

FIG. 31 shows that the amide group is relatively free to rotate around bond a, and the whole imidazolecarboxamide can freely rotate around bond b. In the solution, the molecule exists in a mix of varied conformations. FIG. 31 also illustrates how this molecule base-pairs with each of DNA bases in a different conformation. Each of the conformations has a different energy due to the asymmetric structure, so one may expect that each base pair has a different, and distinct, free energy. Thus, it may be possible to read unique signals out of the tunneling device.

The synthesis of 4-(mercaptomethyl)-1H-imidazole-2-carboxamide starts from (1-trityl-1H-imidazole-5-yl)methanol. First, the hydroxyl group can be converted to tbutyldisulfide as a latent thiol function,[34, 153] and then a cyano group introduced to 2-position of the imidazole ring,[154] which can be hydrolyzed to carboxamide.[155] Finally, the desired product can be obtained by detritylation and reduction of the disulfide.

Theory and Modeling of Base Readers

The operation of the base-recognition head is an interesting mix of mechanics (H-bond strength) and electronics (high conductance when bonded). Modeling requires both MD-simulation[156, 157] and ab-initio quantum chemistry methods[158, 159] Such tools can be used to evaluate the "base-readers" described above. Complete wires can be modeled with pseudopotential density functional theory (DPT).[160, 161] Complete circuits including the leads can be modeled with local orbital DFT techniques.[162-164] One can also test for unexpected outcomes. This can be done by using simpler empirical potentials and constructing tight-binding electronic structure models[165] to search for alternate bonding schemes, conformational isomers or tautomers.

Characterization and Control of DNA Translocation through a Functionalized Pore

The operation of the sequencer depends on the speed and controllability of translocation, the role of the sequence itself in pore-friction and the degree to which secondary structures delay transit. The many studies of DNA translocation through a nanopore have generally focused on unfunctionalized nanopores (the exception is Astier et al.[19]). Translocation through a functionalized nanopore is different. This should be evident given that λ-DNA translocates a approximately 6 nm diameter pore in a few ms (at V=50 mV and 1M KCl),[166] equivalent to a speed of 8 mm/s. It is has been measured that the H-bond lifetime is on the order of a few ms, which corresponds to a "speed" of just microns per second, on the assumption that each base is trapped in the reader for a millisecond or so, since even with negative base reads, the phosphate-guanidinium trapping still occurs. The force generated in the STM pull is probably dominated by the softer material in the gap, as disclosed in He et al.[90], but it is surely quite large, as H-bonds require forces on the order of 100 pN to rupture at these pulling speeds (see FIG. 13 and Ashcroft et al.[50]). In one study of (cyclodextrin) functionalized nanopores, nucleotides became trapped for significant times, illustrating the large effect of pore functionalization.[19]

In accordance with one embodiment of the present invention, translocation of DNA through functionalized nanopores can be accomplished using magnetic beads affixed to a leading end of the DNA as the primary manipulation tool, because this technology is compatible with parallel operation of many reading heads. This is because one set of magnets can pull many beads. The force on a bead of volume v and magnetization m in a field gradient $$\frac{\partial B}{\partial z}$$

is given by $$F_z = mv \frac{\partial B}{\partial z}.$$

With a field gradient of 100 T/m (readily obtained with permanent magnets) and 3 μm superparamagnetic beads available from Magsense (West Lafayette, Ind.), forces of up to 150 pN are obtainable. This is comparable to optical tweezers[167] and also similar to the larger electrophoretic forces experienced in nanopores.[166] A "magnetic tweezers" apparatus[168] having a high field gradient magnet stack[169] can be used to study translocation in functionalized nanopores.

Figure 32:
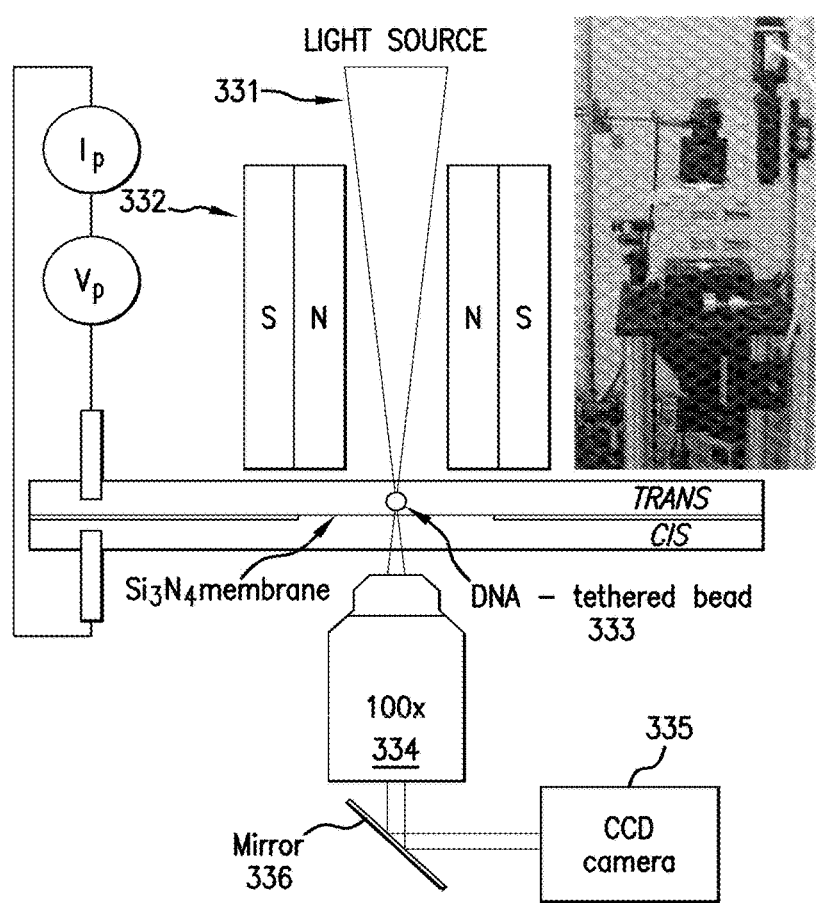
FIG. 32: Magnetic bead apparatus. The CCD can track a bead being pulled into the nanopore to within 10 nm. Inset (upper right) is the prototype laboratory apparatus.

FIG. 32 illustrates a device 320 that can track DNA transit to within 10 nm by fitting the Airy-fringe pattern around the bead when the objective is out of focus. The time resolution is limited to the 50 Hz frame-grabbing rate of the camera interface, but this is adequate with 1 ms transit times because the height resolution is limited to around 20 bases (and 20 bases can transit in about 20 ms which is $\frac{1}{50}^{th}$ of a second). The device 320 includes a light source 331 which projects a light beam past magnets 332 towards a DNA-tethered bead 333. A lens 334 amplifies the bead signal and the resulting image is directed to a camera 335 via a mirror 336. It is understood that other detection arrangements may also be employed.

Figure 33A:
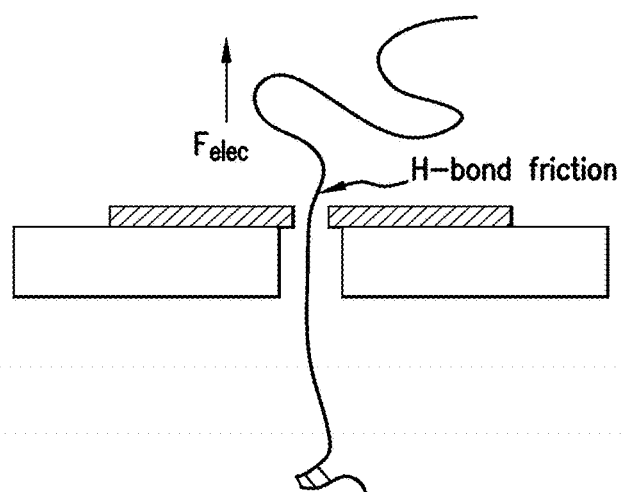
FIG. 33A-C: (a) Forces on a molecule with bead stretching and electrophoretic translocation, (b) Bead arrangement for 'flossing' experiment, (c) Magnetic force added to electrophoretic force.

FIG. 33A illustrates some of the factors controlling translocation. The electrophoretic force, $F_{elec}$, is opposed by H-bond friction 331 in the gap 332. The entry of the DNA 333 into the pore 334 is typically opposed by entropy fluctuations, and, more importantly, secondary structure 335. For a secondary structure undergoing random thermal openings at a rate $k_0$, the opening rate on application of a force $$f \text{ is } k(f) = k_0 \exp\left[\frac{fx_{is}}{k_B T}\right]$$

where $x_{is}$ is the distance to the transition state from the folded state along the direction in which the force is applied. The smallest values of $k_0$ for hairpins trapped in a nanopore is about 1 s$^{-1}$ which is really very slow. Based on measured values for $x_{is}$ for a tight molecular nanopore[50] (about 0.1 nm) an electrophoretic force of 100 pN would increase the opening rate to about 10 s$^{-1}$. Thus, secondary structure could be a significant obstacle to fast reads. The ssDNA could be pre-stretched using the magnetic bead 336 but this would reduce the net force across the pore 334, increasing the rate of backwards slippage.

Figure 33B:
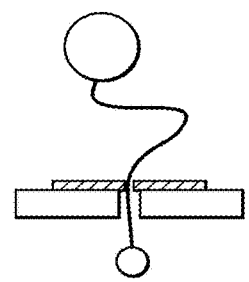
Figure 33C:
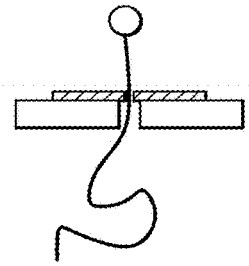

As seen in FIG. 33B, pre-stretching would probably require a bead 335a, 335b trapped at both ends to form a rotaxane with the nanopore[170].

As depicted in FIG. 33B, in yet another arrangement, one may want to augment the electrophoretic force using a magnetic bead 335c.

In each of these experiments, one can measure the output of the sensing electrodes using a DNA molecule of known sequence. This allows one to correlate features in the gross transport (as measured by bead movement and pore current) with local features (as measured by the molecular recognition signal from the sensing electrodes). One approach is to use the M13 genome as a source of long ssDNA (6.5 kb). Cutting it requires hybridization with a short helper strand in order to form a local dsDNA template for a restriction enzyme. The short strand is easily removed by filtration after denaturation. Next, splint-ligation may be used at both ends, putting in a biotin at one end and a digoxigenin at the other, with a two step affinity column purification of the long product. Modification of λ-DNA using incorporation of modified dNTPs followed by magnetic extraction of the desired strand at high pH may also be performed. The "flossing" experiment (FIG. 33B) can be carried out by trapping the DNA-antiDIG bead from the cis chamber using electrophoresis and then functionalizing the DNA in the trans chamber with a strepavidin coated magnetic bead. Finally, a novel "unstructured" DNA[171, 172] may be available for use (see the letter from Laderman). This forms Watson-Crick basepairs with natural bases, but the modified bases will not pair with each other. Presently, the modified nucleotides can be incorporated in runs of up to 600 bases.

It should be evident to one skilled in the art that the foregoing enables one to improve upon the basis design and methodology. More particularly, one may;

Measure the transit time of known oligomers through nanoelectrode pores;

Re-measure transit times with functionalized pores. One can thus test to see if the asymmetry of the backbone (5'-3' vs. 3'-5') affects readout fidelity and transit times, using bead functionalization at one end or the other;

Measure transit times as a function of pH. Secondary structure is removed at low pH[38] but the same conditions that remove secondary structure (pH>11.6) may also destroy H-bonding.

Measure transit times through both functionalized and unfunctionalized pores with unstructured DNA to measure the extent to which secondary structure slows entry into the pore.

These measurements can determine the relative contributions of secondary structure and H-bond friction in slowing transit Magnetic bead experiments may be designed to speed up or slow down the translocation as needed. One may test these arrangements using the functionalized, linearized M13 DNA, correlating the local sequence data from the sensing electrodes with the progress of translocation as measured optically Theory and Simulation Simulations must include all the forces acting on the ssDNA as it translocates[17, 173-175]—the magnetic force on the bead, the electrophoresis force on the charged ssDNA, the hydrogen bonding force of the guanidinium attempting to hold the DNA in place, the hydrogen bonding force of the base-reader on the target base, interactions of ssDNA with itself (secondary structure), the viscous force of the water on the magnetic bead, and interactions of the DNA with water and with the walls of the nanopore. The length of the tether molecules is also critical. Varying it, even slightly, may change the number of contacts and/or the probability of simultaneous phosphate and base recognition. Modeling helps guide the correct choice of parameters for successful sequencing. Simulation strategy combines three main ingredients—molecular dynamics (MD) simulations,[157, 176] coarse grained simulations[177, 178] and analytic modeling at all levels. Molecular dynamics can be used to pick out key molecular aspects of the problem, specifically in the nanopore itself. Even within the timescale-limitations of current MD techniques they provide a picture of the mechanisms occurring within the active region of the pore. The data produced from the MD simulations can be used to build a coarse grained model of the process using a Brownian dynamics algorithm[177] of a chain model for the ssDNA with a magnetic bead in a viscous fluid.[179] Interactions observed in the nanopore from the MD simulations can be included parametrically. Free energy data for secondary structure can be incorporated together with existing kinetic data.[18, 50]

Characterization of Signals from Oligomers and Genomic DNA Using a Set of Single Pores.

The sequence-reconstruction problem has two inputs. One is the optical tracking of transport which could give data at a resolution that could be as high as 20 bases. The second is the signals from the molecular reading heads themselves. Reading head data of adequate quality could permit alignment of data from all four reading heads with no other input Data for each individual base that is 99.99% accurate may be obtained by a combination of improved affinity elements and multiple reads of the same sequences. If the data from each head are of adequate quality, one may record repeated runs for each type of base with high fidelity.

When sequencing four copies of ssDNA using four nanopores, each nanopore having a different base reader as the second affinity element, four component sequence reads are created. Each sequence read identifies, as a function of base location, the points at which a nucleotide of a particular type has been detected. Since there may be differences in the rates at which the four copies of the ssDNA electrophoreses through their respective nanopores, there may be an issue of aligning the four component sequence reads to arrive at a final sequence read representing the sequenced ssDNA. Blocks of a repeated base (e.g., 4× or 5×) are rare enough that they can serve as good indices of position in the genome, and yet frequent enough so that a significant number of them occur in each read. Thus, upon obtaining a sequence of component reads of ssDNA from each of four readers, one may align the four sequences of component reads based on one or more preselected blocks of a repeated nucleotide (which hopefully will be present in at least one of the sequences of component reads.) For example, positive reads of an $A_5$ tract (A-A-A-A-A) would be aligned with unique (or rare) gaps of null readings of 5 bases in extent from the C, G and T readers. This is called the "framing problem" in parallel transmission of digital data over noisy channels.[180] The problem is greatly simplified if the direction of the data stream (e.g., 3'-5') is fixed. Thus one can develop protocols for preprocessing input DNA and ligating beads (or even just form crosslinked dsDNA blockers) to control the entry direction. Once any such needed alignment has been done, one may then create a final sequence of reads representing the sequenced ssDNA from the four component sequences of reads.

The optical tracking data can record each translocation to within 20 bases at best, with maybe substantially poorer resolution when entropy and secondary structure fluctuations are taken into account. But it also serves as a check on the local alignment algorithms, eliminating gross mistakes (i.e., juxtaposition errors greater than the optical tracking resolution).

Quantitative data obtained from using the device of the present invention may be used to develop data analysis tools for rapid sequence recovery. Some of the issues that can be addressed by such quantitative data (1) the transit times per base in the read (base+phosphate H-bonds) vs. the no-read (phosphate H-bonds only); the frequency with which a nucleotide is missed altogether; (3) the fluctuations in average read speeds; (4) the role of secondary structure; and (5) whether it would help if "stalling," owing to secondary structure, occurred predictably.

As discussed herein, one may construct a fixed-gap nanopore sequence device capable of reading single bases with high fidelity. Such a device may incorporate one or more of the following features: electrochemically grown self-aligning electrodes, active gap adjustment, and gold as the electrode material. In use, such a device may be able to deal with the potential problems of secondary and tertiary structures in long DNA transits. Furthermore, the assembly of such devices may be facilitated and even automated for consistency from unit to unit, thereby mitigating uncertainties in the performance of one-off designs. The assembly and functionalization methods allow for reforming and healing of devices whose readers have been damaged or otherwise spent.

EXAMPLES

Example 1

Electrode-Tethered Guanidinium Ions can be Used to Complete an Electrical Circuit for "Reading" Bases in Single Stranded DNA Hydrogen bonds are the molecular "Velcro" on which much of the reversible and chemically-specific bonding in biology is based.[186] It has recently been shown that hydrogen bonds can also enhance electron transport significantly,[12, 90] observations that suggest a basis for a new type of electrical biosensor. This sensor would use two sets of hydrogen bonds to complete an electrical circuit by simultaneously binding two independent sites on a target molecule.

Electrical contacts to DNA are currently made by means of covalent Modifications 187 but it is possible to form "generic" hydrogen bonds to DNA by means of an interaction between the backbone phosphates and guanidinium ions.[188] This then allows the construction of a "molecular sandwich" consisting of hydrogen bonded contacts to DNA via the phosphates on one side and a base on the other side as illustrated schematically in FIG. 1. The use of different "Base Recognition" elements (FIG. 1) generates electrical signals characteristic of a particular target base in the DNA.

A guanidinium monolayer was prepared by reacting β-mercaptoethylguanidine ("Phosphate Recognition" element) with Au (111) surfaces and scanning tunneling microscope (STM) images (taken in Tris buffer) are shown in FIGS. 11B and C. The single-atom deep pits characteristic of thiol adsorption on gold[189] (arrows in FIG. 11B) proved to be sensitive to the anions in solution and disappear in phosphate buffer.

DNA molecules in Tris buffer bind to these surfaces rapidly and irreversibly, as verified by surface plasmon resonance and Fourier transform infrared absorption spectroscopy. The adsorption is specific because it is inhibited in phosphate buffer.

Electrical contact to the backbone phosphates was verified by taking STM images of DNA adlayers on the guanidinium-functionalized electrodes. STM of DNA[190, 102, 8] has been the subject of controversy[103] and the images of these adlayers have unexpected properties, so the same region of the guanidinium-treated substrate was imaged before and after injection of a 2.8 kbp double stranded (ds) plasmid DNA (Litmus 28i from New England Biolabs) into the sample cell of the microscope (FIGS. 14A and B). The underlying gold reorganizes, causing the pits (arrows, FIG. 14A) to disappear and a striped texture to appear on the surface (white lines, FIG. 14B) when DNA is adsorbed. A median-leveled image of a flatter region (FIG. 14C) shows the dsDNA geometry quite clearly. The individual dsDNA molecules look like rows of "beads" (arrows) with a helical repeat of 2.9 nm, close to that of A-DNA (see the 2D-FFT, inset). The intermolecular packing distance (white lines) is about 2.8 nm. The dsDNA packs into a dense, highly organized layer, despite its nominally circular structure. To test the interpretation of the "beads" as turns of the double helix, long single-stranded (ss) loops of DNA (the 6.8 kb M13 genome) were imaged. A characteristic image is shown in FIG. 14D. The "beads" are absent and the features are narrower. The need for specific hydrogen-bonds was tested by attempting to image DNA on cystamine-treated gold electrodes (which interact with phosphates less specifically) hut images were unobtainable.

Images of small ssDNA oligomers (12 to 79 bases) appeared to be extremely smooth, presumably because they were more perfectly packed, but when molecular features were resolved, they corresponded to the known dimensions of the oligomers. These densely packed layers appear to require DNA-DNA interactions (much like bulk DNA condensation[101]) because the shortest oligomers and DNA minicircles (too small to bend) did not form ordered layers. In turn, the ordering appears to be necessary to hold the DNA in place under the sweeping motion of the STM probe, as atomic force microscopy clearly shows that isolated molecules can adsorb as well.

To test for the role of DNA-DNA interactions in the reversibility of the absorption process, the adhesion of single molecules using DNA tethered to an AFM probe was measured. The force curves obtained on pulling the DNA away from the surface showed features characteristic of the breaking of individual hydrogen bonds, suggesting that additional DNA-DNA interactions are required for the formation of the ordered monolayers.

The STM images demonstrate that charge can be transported laterally through the tethered guanidinium and the ssDNA or dsDNA molecules with a conductance on the order of a few tens of pS (currents of ca. 10 pA at a bias of a fraction of a volt).

Example 2

A readable signal is obtainable if the circuit is completed using a complementary DNA as second connector. Transport measurements were carried out on the DNA adlayers using gold STM probes insulated with polyethylene, functionalizing the exposed gold apex with a thiolated nucleobase.[90] Either 8-mercaptoguanine (G) or 8-mercatpto-2 aminoadenine (2AA) was used. 2AA was chosen because it can form three hydrogen bonds with thymine.[181]

Figure 34A:
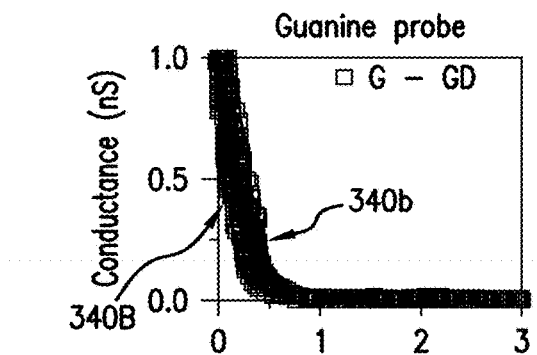
FIG. 34: I-Z curves for a guanine functionalized probe (A, C, E) and a 2-aminoadenine functionalized probe (B,D,F) over a bare guanidinium monolayer (A,B), a 45 base oligo T (C,D) and a 45 base oligo dC (E,F) adsorbed onto guanidinium. 3 H-bond interactions give signals that extend significantly beyond 1 nm (vertical gray lines). Initial set point is 0.4 nA at 0.4V, 133 nm/s retraction speed.
Figure 34B:
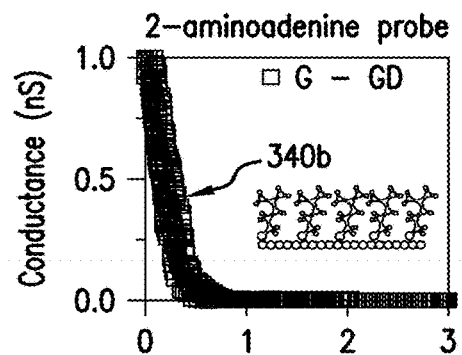
Figure 34C:
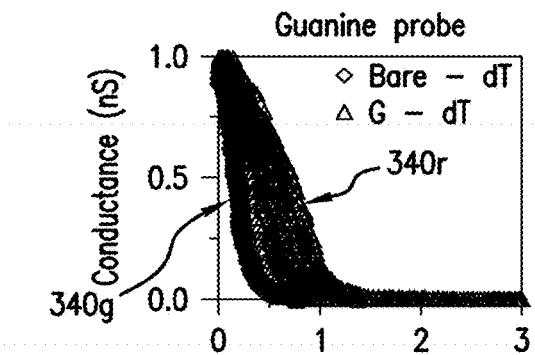
Figure 34D:
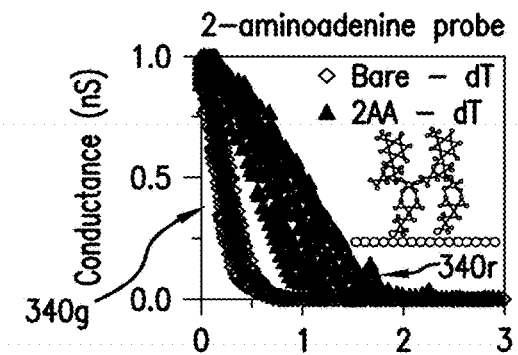
Figure 34E:
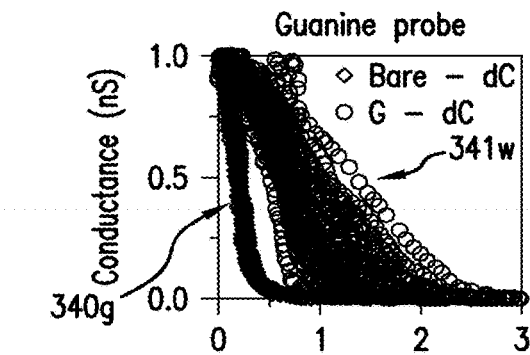
Figure 34F:
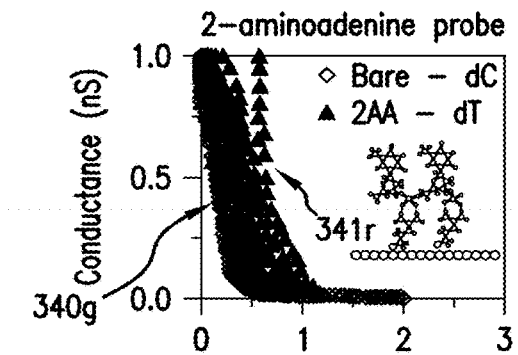
Figure 35A:
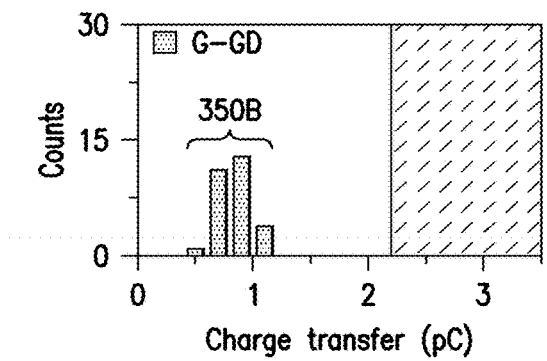
FIG. 35: Histograms of charge transfer for the I-Z curves. A,C and E are for guanine functionalized probes and B,D and F are for 2-aminoadenine functionalized probes. A and B (blue bars) show data obtained on the guanidinium monolayer, C (orange bars) and D (red bars) show data obtained with oligo T, E (brown bars) and P (red bars) show data obtained with oligo dC. Charge transfers>2.2 pC (blue shaded boxes) are unique to the three-hydrogen bond interactions (E and D) and so serve to identify the target base.
Figure 35B:
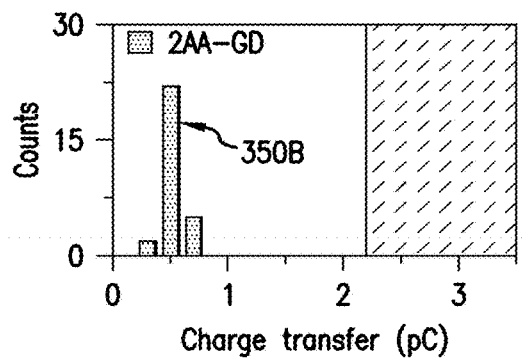
Figure 35C:
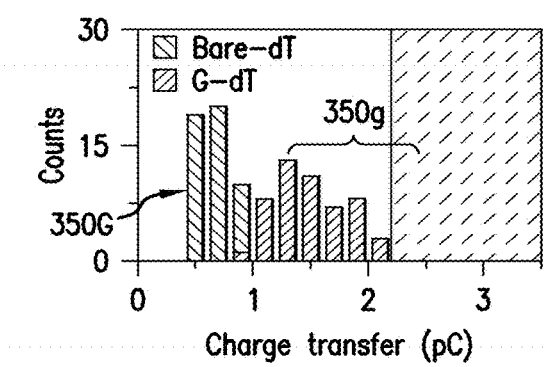
Figure 35D:
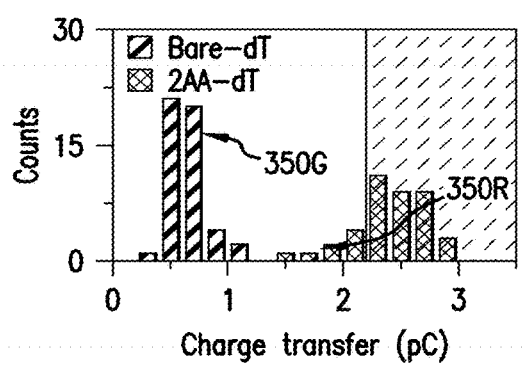
Figure 35E:
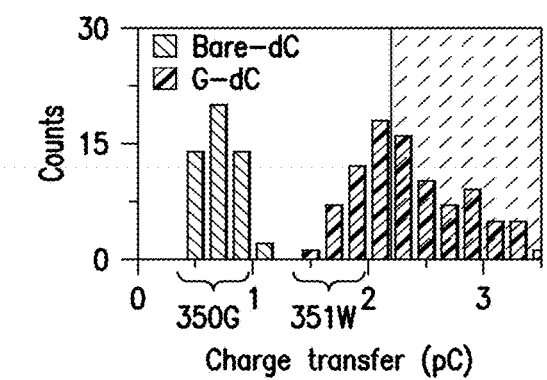
Figure 35F:
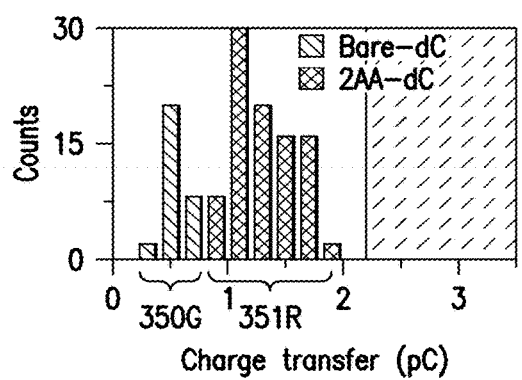

Examples of conductance vs. retraction-distance (I-Z) curves taken with these functionalized probes are given in FIGS. 34A-F, with the vertical line in each figure denoted the 1 nm distance mark. The green lower curves 340g in FIGS. 34C-34F are control data taken using bare gold probes. All of the experimental data taken in a successful run have been overlaid with no pre-selection of the curves. When no DNA is present. G and 2AA probes yield decay-curves 340b over guanidinium (all curves in FIGS. 34A and B) similar to those obtained with bare probes (green lower curves 340g in FIGS. 34C-34F). With a 45 base oligo-T adsorbed onto the guanidinium, the G and 2AA probes yield very different signals 340o, 340r, respectively (FIGS. 34C and D). With a G-probe, the signal 340o has decayed after 1 nm (FIG. 34C), whereas the 2AA-probe yields signals 340r out to nearly 2 nm (FIG. 34D). The response is reversed with a 45 base oligo-dC adsorbed onto the guanidinium: the G-probe signal 341w (see FIG. 34E) extends much further that the 2AA-probe signal 341r (FIG. 34F). Thus, the extended signals are characteristic of triple hydrogen bonds.

The curves shown in FIG. 34A-F were quantified by integrating them and forming corresponding histograms 350a, 350g, 350o, 350r, 351w and 351r. The integral is equal to the charge transferred when the horizontal axis is converted to time using the retraction speed of the probe, and the distribution is shown in FIGS. 35A-F, respectively. Charge transfer in the blue-shaded regions 350b (appearing, e.g., in FIGS. 35A & 35B) uniquely identifies the triply hydrogen bonded interactions (G with C, 2AA with T). With the charge transfer set to this threshold, there are no false positive reads so only a small number of repeated reads would identify a base with a high fidelity.[90]

The high value of set-point conductance and the slow decay of current do not reflect the intrinsic electronic properties of the DNA because the tunnel junction is under significant compressive stress, so the I-Z curve will be affected significantly by elastic distortion of the material in the gap[90]. A better estimate of the conductance of the DNA is given by the value in the region of rapid decay just before the H-bonded junction ruptures.[90] Inspection of the curves in FIGS. 34A-F suggests that this conductance is on the order of tens of pS.

Figure 36:
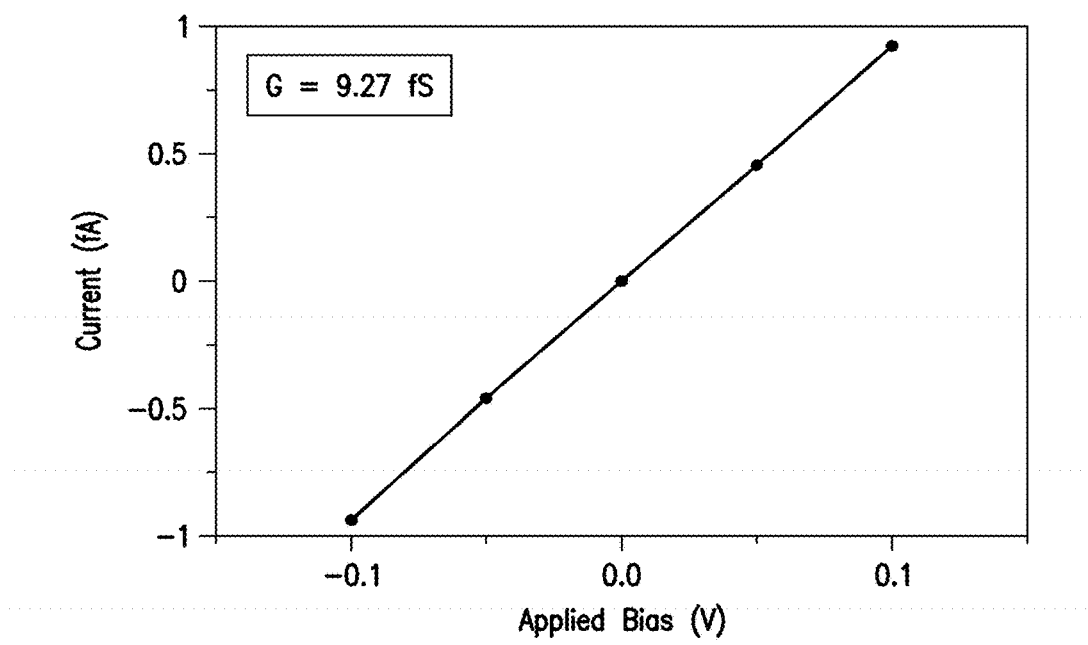
FIG. 36: Calculated current-voltage curve for "guanidinium-phosphate-sugar-cytosine-guanine" on Au(111) with the thiol positioned above the hollow site.

To determine whether this value of conductance can be explained by a tunneling process, a theoretical investigation was performed by evaluating the conductance from a current-voltage (I-V) curve for "guanidinium-phosphate-sugar-cytosine-guanine" connected to gold contacts. The tunneling current was computed using a density functional theory (DFT) Green's function scattering method[67, 182] based on the Landauer approach[183, 184] and details are given in the supporting information. The calculated conductance due to tunneling (FIG. 36) for "guanidinium-phosphate-sugar-cytosine-guanine" (g-p-s-c-g) is remarkably low, 9.27 fS, smaller than the experimental estimate by several orders of magnitude.

To understand the origin of such low predicted conductance, the complex bandstructure was investigated for each of the two hydrogen-bonded components (a G-C basepair and guanidinium-phosphate couple) separately, as well as for the complete g-p-s-c-g assembly. The calculations yield an upper limit on the inverse electronic decay length, $\beta$, assuming that the Fermi level lies midway between the highest occupied and lowest unoccupied molecular orbitals.[57] Table 2 lists the structures investigated this way, together with values for $\beta$ and the length, L, of the "unit cell" of the repeated structure. An order of magnitude estimate (right column. Table 2) of the tunnel conductance is obtained using $G \approx G_0 e^{-\beta L}$ where $G_0$ is the quantum of conductance (77 $\mu$S).[57]

Two striking features emerge from these calculations. First, the conductance of the G-C basepair is remarkably high, on the order of nS, a value one might expect from a sigma-bonded system.[107] Second, the guanidinium-phosphate shows an extremely low conductance, on the order of pS. As a result, the conductance of the whole assembly remains very low (on the order of fS). To improve the estimate of the conductance, G was recomputed using β at the Fermi level predicted by the DFT calculations. At 1.32 fS it is still much lower than the experimental estimate. Since tunneling calculations are generally in reasonable agreement with the data for smaller molecules[107] we concluded that some mechanism other than tunneling operates in this system. Our calculations do not include finite temperature or polarization effects arising from the surrounding solvent, so that transport mechanisms involving charge localization[185] might come into play.

Figure 37:
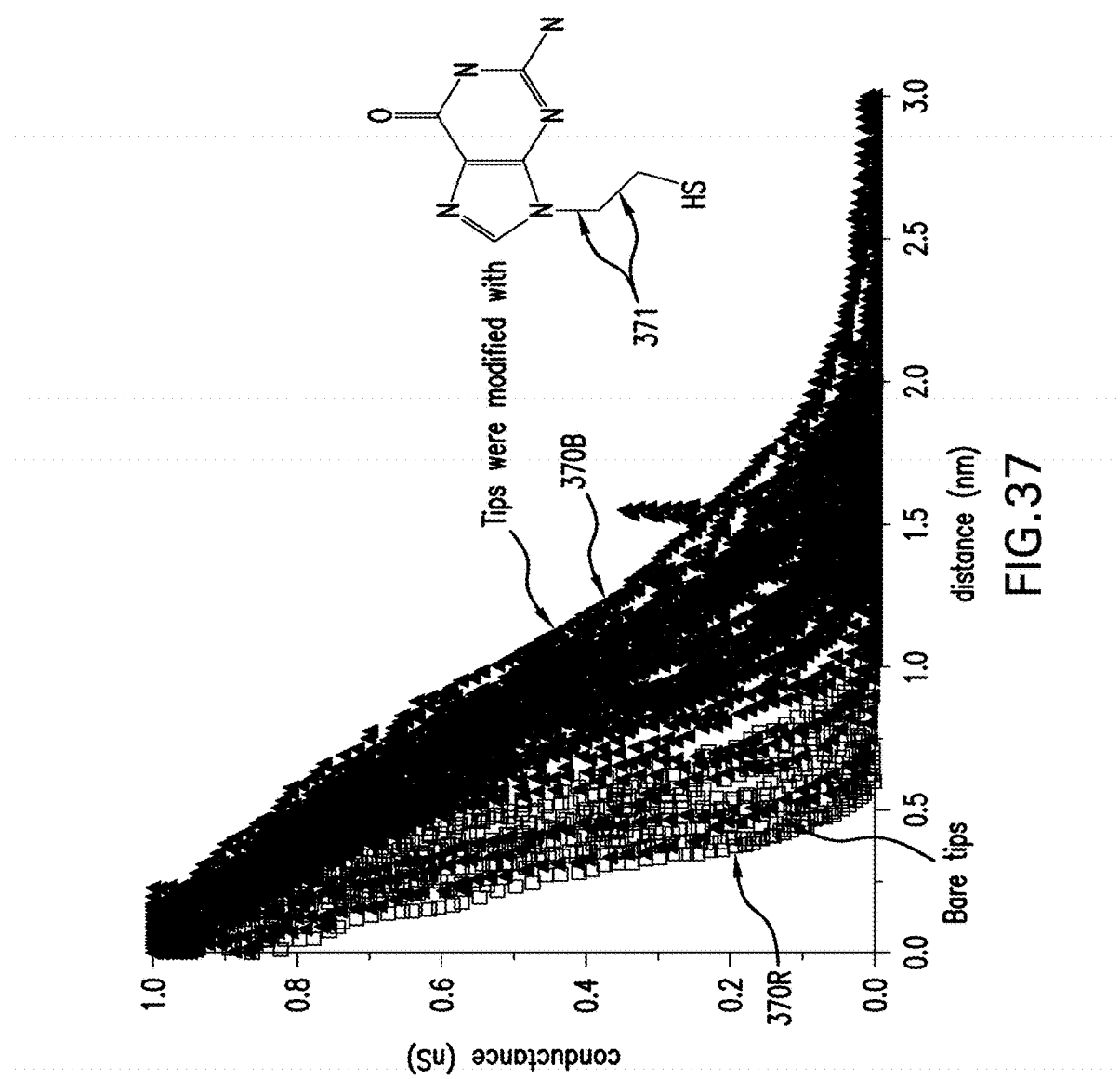
FIG. 37: Raw current vs. distance data for a bare tip (red) vs tips modified with a modified guanine having two methylene units attached to the N. Data were taken in 0.5 mM tris-HCl.

FIG. 37 shows the I-Z (current distance) curves for the linker shown. This linker has two methylene units in series attached to the N of the guanine in the structure. The bundle of darker curves 370b on the right side of the plot are oligo-cytosine recognition curves. The strands of light curves 370r on the left side of the plot are controls taken with a bare tip. The signal levels are seen in this figure to be relatively high with the indirect linkage of the guanine not affecting the process.

In the embodiment of FIGS. 1 and 1A, the constriction is in the form of a nanopore 1 which passes through a thickness of a substrate. It is understood, however, that a constriction may take on other forms and arrangements as well. Thus, in an alternate embodiment, the constriction may comprise a narrowed portion of a microfluidic channel formed on a surface of a substrate. In other words, the constriction may lie on top of a device with the target molecule passing from a first chamber on top of the device to a second chamber on top of the same device. In such case, the constriction connects the two chambers which are separated by a surface partition.

Figure 38:
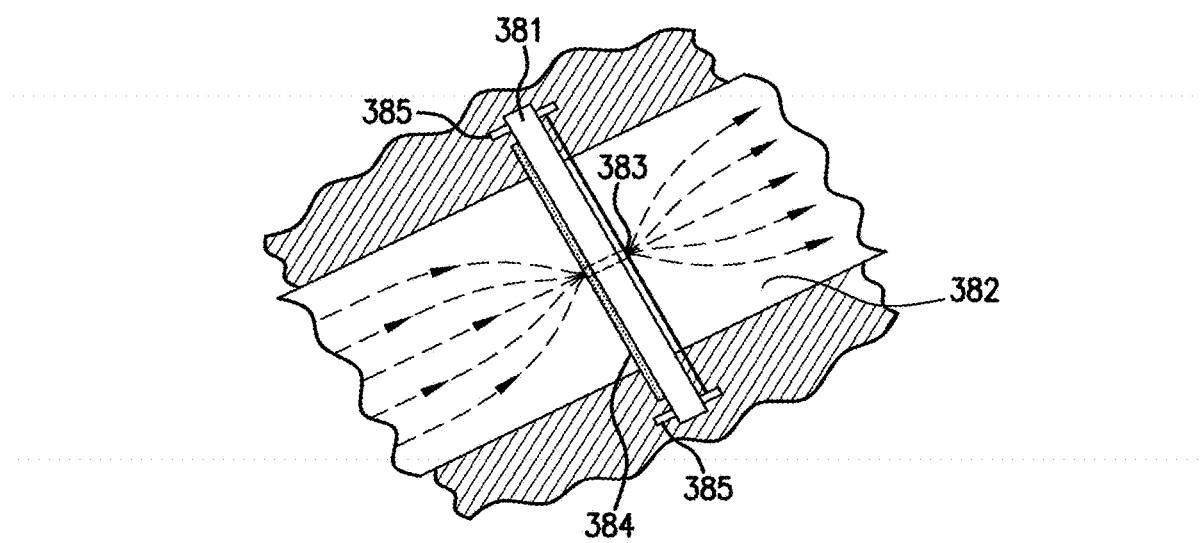
FIG. 38 shows an embodiment of a device in which the constriction in found in a microfludic channel formed on a surface of the device.

FIG. 38 shows an exemplary arrangement, where the device 381 is placed in a microfluidic channel 382. The stream lines show the fluid being diverted in order to pass through the constriction 383. The electrode surfaces within the microfluidic channel me insulated from the fluid in the channel by a protective layer of insulation 384. Connections to the electrodes 385 exit the structure outside of the fluid channel.

Figure 39A:
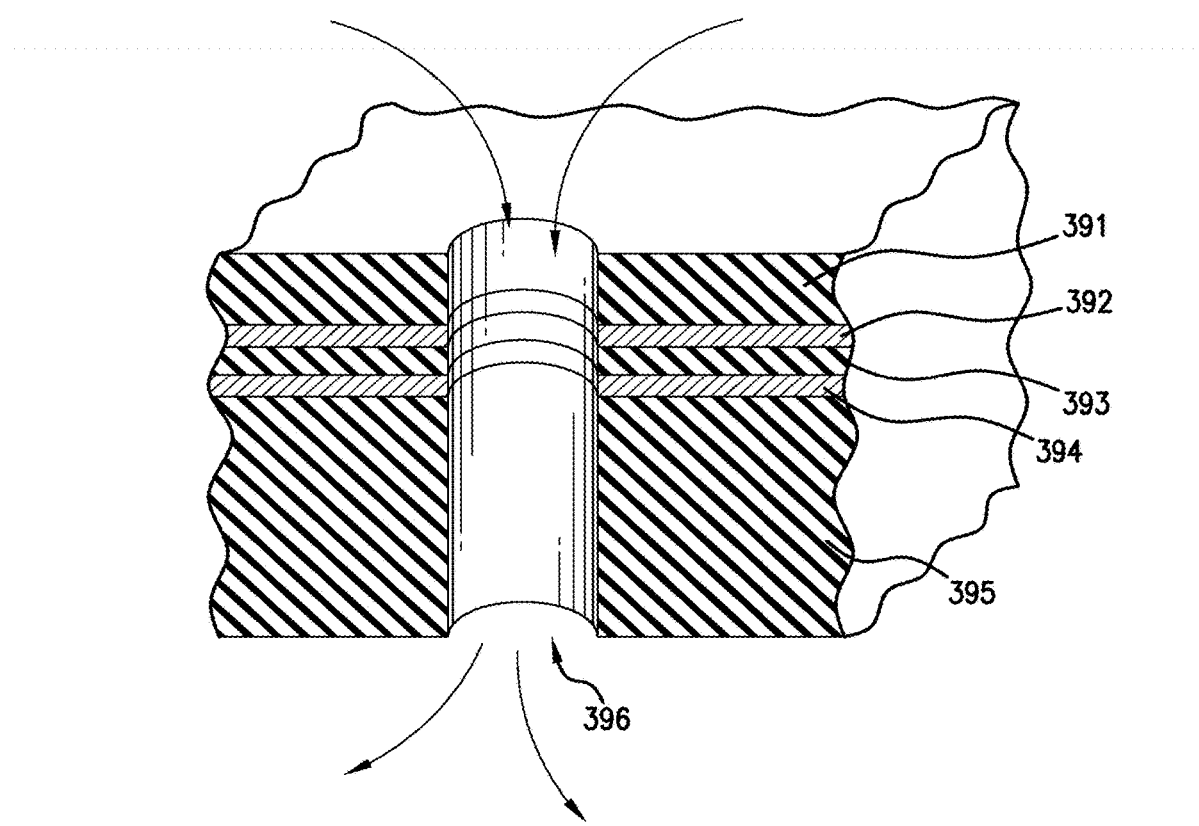
FIGS. 39A and 39B show an embodiment of a device in which the constriction is a pore through a substrate and the electrodes comprise layers along the thickness of the pore.

FIG. 39A shows an exemplary cross section of an embodiment of a device 391 through a fluid channel showing a planar electrode arrangement. 391 is the top layer of insulation, 392 is a first metal or doped semiconductor layer, 393 is a second layer of insulation, 394 is a second metal or doped semiconductor layer and 395 is the insulating substrate on which the structure is formed. The size of the constriction between the electrodes is determined by the thickness of the second layer of insulation 393. The structure is assembled by planar deposition of alternating conducting and insulating layers on the substrate, followed by formation of a channel, 396, through the entire structure.

Figure 39B:
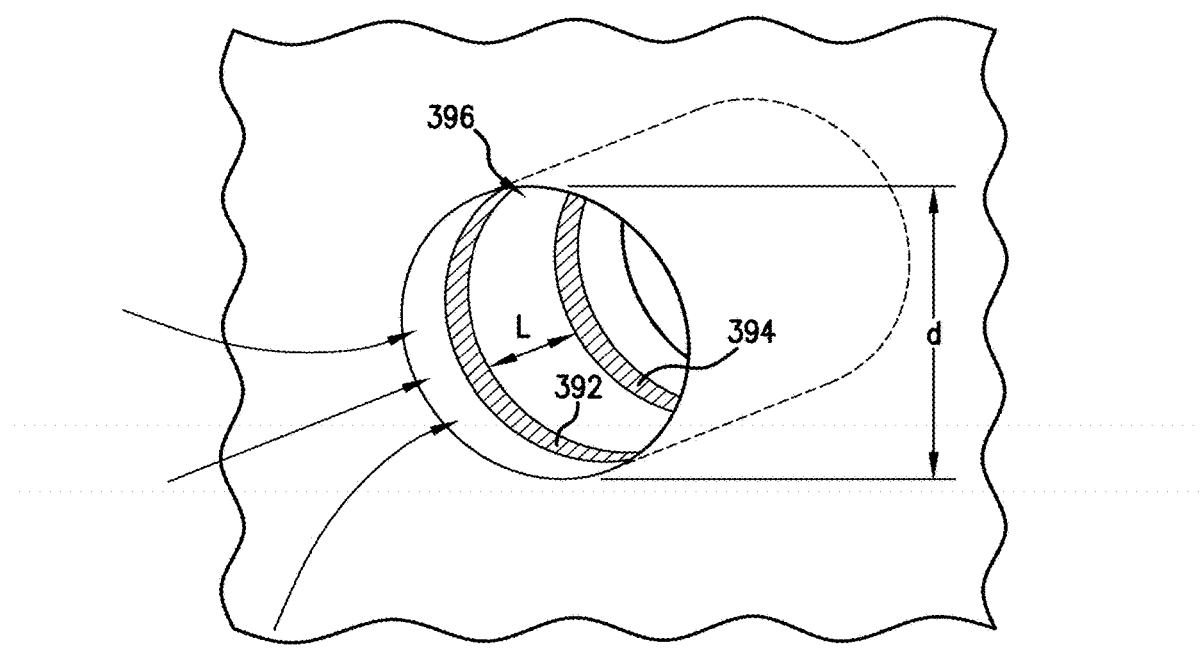

FIG. 39B illustrates one embodiment of dimensions for operation of the device seen in FIG. 39A. In this embodiment, the spacing between the electrode pair, 392 and 394, is L and the diameter of the channel 396 diameter is d. In order to obtain adequate tunnel conductance through the target molecule, L lies in the range from 0.5 to 10 nm. The channel diameter is constrained only by the requirement that a molecule entering the channel touch the sides, and hence the electrodes, during its transit through the channel. If the speed of fluid flow through the channel is V meters per second than the time spent between the electrode pair is:

$$t = V/L \text{ seconds.}$$

In this time the molecule must diffuse a lateral distance d, given by $$d = \sqrt{Dt}$$

where D is the diffusion constant of the molecule. Thus the maximum speed of transit of the sample passed the electrodes is given by $$V \text{ DL}/d^2.$$

Thus the speed with which fluid can be processed decreases rapidly as the constriction size is increased. For example, with D=5 nm, d=10 nm and D=100(m)2/s (typical of a small protein), V is preferably less than 5 mm/s.

Figure 40A:
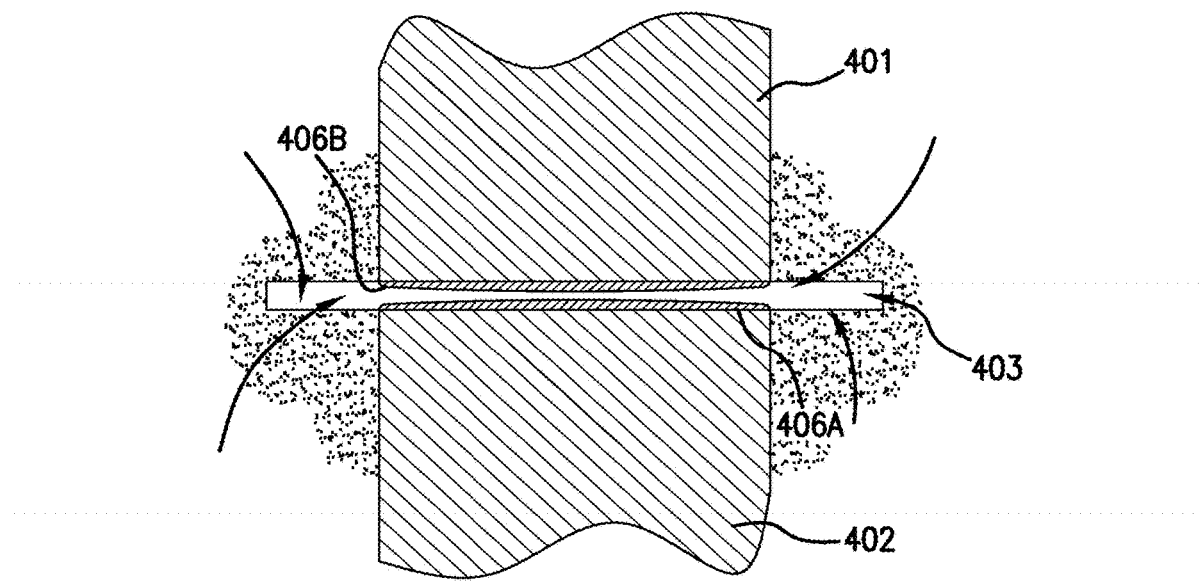
FIGS. 40A and 40B show an electrodes comprise chemically deposited layers of conducting metal.
Figure 40B:
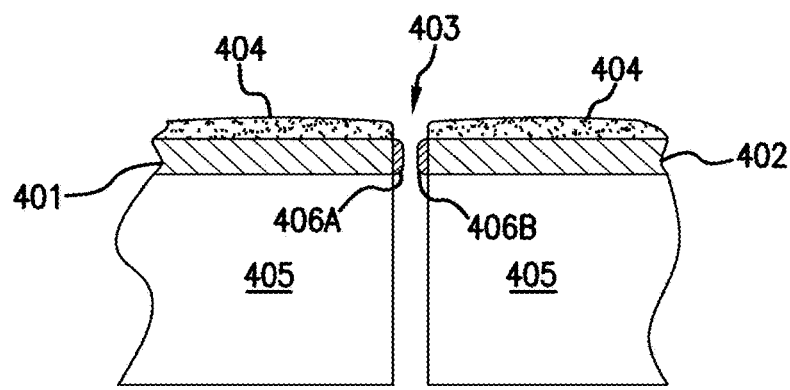

FIG. 40A shows a top view and FIG. 40B shows a cross section of a further embodiment using opposing electrodes. 401 is a first linear metal or doped polysilicon electrode. 402 is a second linear metal or doped polysilicon electrode. 403 is a channel that has been milled through the entire structure. 404 is a protective insulating layer that covers the electrodes. 405 is the underlying insulating substrate. 406A and 406B are electrodes, which may be chemically deposited layers of conducting metal used to achieve a small constriction between the opposing electrodes 401 and 402.

One exemplary manner of assembling the structure of FIGS. 40A and 40B is to make a stripe of doped polysilicon conductor on the substrate 405, then coat over this stripe and the substrate with an insulating layer of oxide, then use a focused ion beam mill to cut a slot through the entire device, separating the stripe of polysilicon into the two opposing electrodes 401 and 402. The channel size resulting from focused ion beam milling is likely to be about 30 nm, so the constriction is narrowed to the desired nanometer dimension by, for example, electric chemical growth of a metal such as gold on to the exposed conducting polysilicon electrodes. This growth can be continued until the junction is short-circuited, and then a small amount of gold removed electrochemically, leaving a constriction of the desired size.

Figure 41:
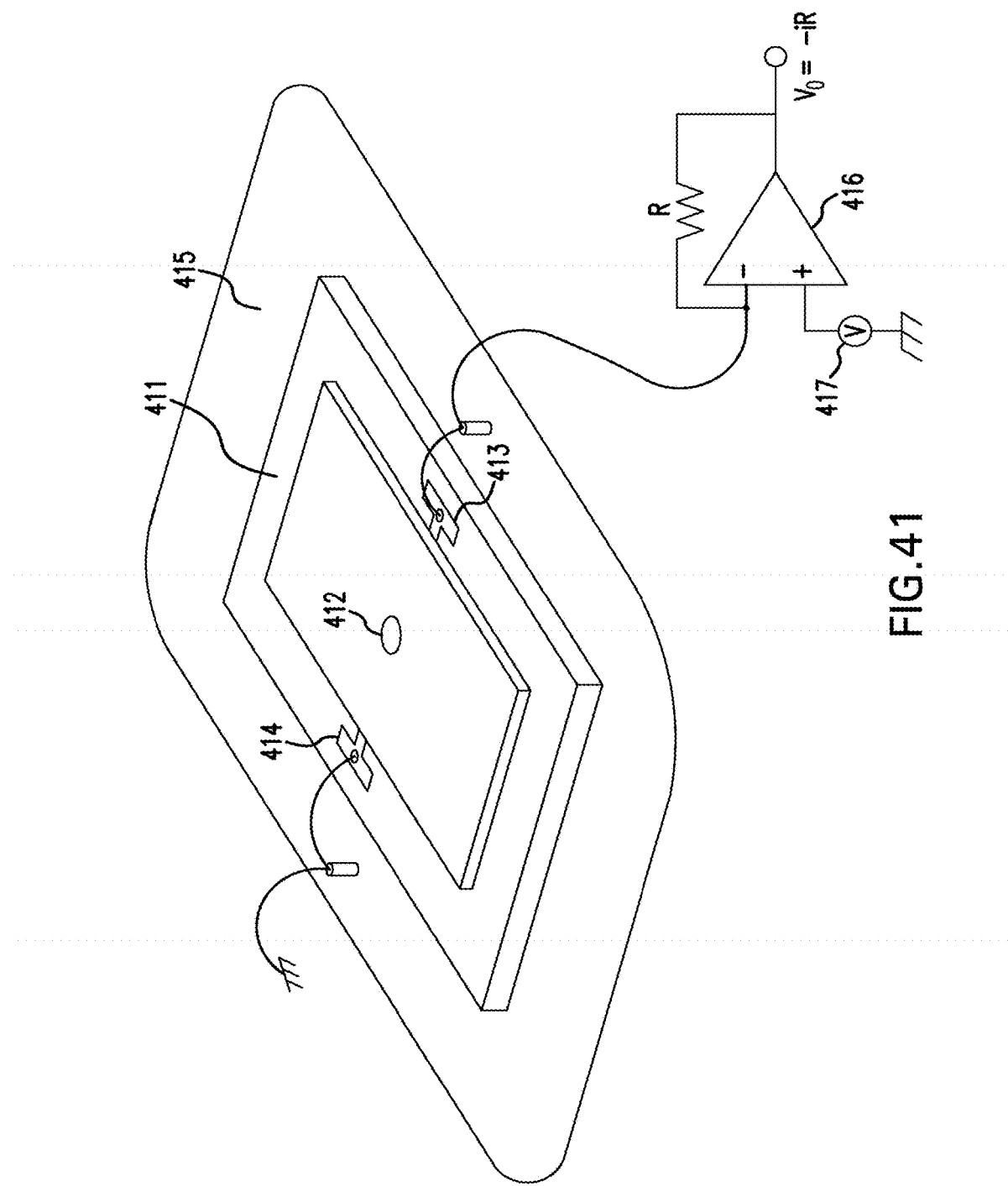
FIG. 41 shows an exemplary electrical arrangement of a device in accordance with one embodiment of the present invention.

FIG. 41 provides an exemplary electrical arrangement embodiment of an apparatus of the present invention. The apparatus comprises a channel 412 formed through a chip 411. Two external connections to the electrodes 413 and 414 are placed on a chip carrier 415 that allows fluid access to the front and back of the channel 412. One electrode 413 is grounded, while the other is connected to the inverting terminal of a current to voltage converter, 416. The non-inverting terminal is connected to a source of bias, 417, so that feedback is applied through the current to voltage conversion resistor R, the inverting terminal is held at a potential of V volts with respect to ground, thus biasing the non-grounded electrode. The output signal of the current to voltage converter 416 is −iR volts where i is the tunnel current signal generated by detection of one or more molecules in the device. Typically V lies in the range from 10 mV to 1V, so that a 1 nS tunnel conductance for a detected molecule would yield a current between 10 pA and 1 nA. With R=1 GΩ this leads to output voltages between 10 mV and 1V. The signal to noise of such a detection system may be improved, for example, by using a larger resistor R, but the response time (RCin, where Cin is the electrode stray capacitance) becomes slower. With an R=1 GΩ resistor, the shot noise is a tiny fraction of 1 pA, while a stray electrode capacitance of 1 pF (possible with appropriate electrode and instillation design) yields a response time of 1 ms.

In each of the embodiments seen in FIGS. 38-41, it is understood that the various linkers, affinity elements, and the like are connected to the various electrodes to create a functioning apparatus in accordance with the present invention.

A device formed and operated in accordance with the present invention may potentially provide a variety of desirable capabilities.

Speed. Under certain conditions, the DNA can be pulled through molecular nanopores[50] at a speed of about 1 μm/s (~1600 bases/second at 0.6 nm per base for stretched DNA). This corresponds to a dwell time of about 0.6 ms/base, well within the range of current single molecule electronic measurements. At this speed, 100 Mb per day could be sequenced in each reader. However, the actual read-speed may be up to 10× slower than this because of the intrinsic molecular friction in an H-bond reader.

Accuracy. It is possible to make unique single molecule identifications for a limited range of combinations of base pairings. This pattern is expected to persist for other combinations, provided that the appropriate affinity elements are used. With a 50% hit rate, 13 independent reads would be needed to reach 99.99% accuracy. On the other hand, a 10% unique hit rate would require 90 reads.

Robustness. The STM measurements mimic the interaction of the functionalized electrodes with the DNA. The STM probes have operated successfully for thousands of measurements each. Spurious (unwanted) adhesion is less with a functionalized probe than with a bare probe.

Long Sequence Reads. Final sequence assembly is relatively straightforward and the DNA can be tracked optically, allowing perhaps 100 microns to be followed through the pore (i.e., >100 kb). The sequential nature of the readout should eliminate problems associated with sequence repeats.

Simplicity. The great attraction of "sequencing by recognition" is its simplicity (compared to other single-molecule schemes). It can use just one measurement (charge transfer) with a threshold to generate a binary output and it does not require labeling DNA or nucleotides. The signal levels (0.5 nA, 0.5V) and read speeds (ms per base) are compatible with CMOS.

Use of native DNA. Given high-fidelity "readers" for all four bases, long genomic DNA could be read with no pre-processing, saving the attachment of end-tethered beads for manipulating the DNA (and even this modification may not be essential).

Cost. The basic reading head unit can be fabricated with conventional lithography, a focused ion beam (FIB) milling step and electrochemistry. Produced in quantity, the read heads should be quite cheap, perhaps on the order of a hundred dollars. One machine might comprise four blocks of 700 read heads, one block for each base. If highly specific recognition chemistries could be found (75% hit rate) each instrument might make 10 reads on 70 different portions of the genome, yielding 4.2 Mega bases worth of 99.99% quality sequence in 1 minute, completing an entire mammalian genome in 17 hours. This short timescale is compatible with a cost goal of $1000/genome.

Thus, in sum, the system described above is potentially able to meet the cost target of $1000/genome, an accuracy of <1 error per 10 kb, long contiguous reads on the order of tens of thousands of bases, and minimal sample preparation, all while reading genomic DNA.

Although the present invention has been described to a certain degree of particularity, it should be understood that various alterations and modifications could be made without departing from the scope of the invention as hereinafter claimed.

LITERATURE CITED

1. E. S. Lander et al., Initial sequencing and analysis of the human genome. Nature, 2001. 409: 860-921.
2. A. J. Sharp, Z. C. Cheng and E. E. Eichler, Structural variation of the human genome, Annu. Rev. Genomic Hum. Genet., 2006. ARI: 407-442.
3. B. E. Stranger, M. S. Forrest, M. Dunning, C. E. Ingle, C. Beazley, N. Thorne, R. Redon, C. P. Bird, A. de Grassi, C. Lee, C. Tyler-Smith, N. Carter, S. W. Scherer, S. Tavaré, P. Deloukas, M. E. Hurles and E. T. Dennitzakis, Relative Impact of Nucleotide and Copy Number Variation on Gene Expression Phenotypes, Science, 2007. 315: 848-853.
4. M. Margulies, M. Egholm, W. E. Altman, S. Attiya, J. I. S. Bader and L. A. Bemben, Genome sequencing in microfabricated high-density picoliter reactors, Nature, 2005. 437: 376-380.
5. I. Braslavsky, B. Herbert, E. Kartalov and S. R. Quake, Sequence information can be obtained from single DNA molecules, Proc. Natl. Acad. Sci. (USA), 2003. 100: 3960-3964.
6. P. Williams, M. A. Hayes, S. D. Rose, L. B. Bloom, L. J. Reha-Krantz and V. B. Pizziconi U.S. Pat. No. 7,037,687 May 2
7. G. Spencer, NHGRI News Release, Oct. 4 (2006)
8. S. M. Lindsay, T. Thundat, L. A. Nagahara, U. Knipping and R. L. Rill, Images of the DNA double helix in water, Science, 1989.244:1063-1064.
9. T. Jing, A. M. Jeffrey, J. A. DeRose, Y. L. Lyubchenko, L. S. Shlyakhtenko, R. E. Harrington, E. Appella, J. Larsen, A. Vaught, D. Rekesh, F. X. Lu and S. M. Lindsay, Structure of hydrated oligonucleotides studied by in-situ scanning tunneling microscopy, Proc. Natl. Acad. Sci. (USA), 1993. 90: 8934-8938.
10. A. M. Jeffrey, T. W. Jing, J. A. DeRose, A. Vaught, D. Rekesh, F. X. Lu and S. M. Lindsay, Identification of DNA-cisplatin adducts in a blind trial of in-situ scanning tunneling microscopy, Nucleic Acids Research, 1993.21: 5896-5900.
11. D. Lampner, PhD Thesis in Physics, Arizona State University, (1995)
12. T. Ohshiro and Y. Umezawa, Complementary base-pair-facilitated electron tunneling for electrically pinpointing complementary nucleobases, Proc. Nat. Acad. Sci., 2006.103:10-14.
13. J. J. Kasianowicz, E. Brandin, D. Branton and D. W. Deamer, Characterization of individual polynucleotide molecules using a membrane channel, Proc. Nat. Acad. Sci., 1996. 93: 13770 13773.
14. A. Meller, L. Nivon, E. Brandin, J. Golovchenko and D. Branton, Rapid nanopore discrimination between single polynucleotide molecules, Proc. Natl. Acad, Sci. (USA), 2000. 97: 1079-1084.
15. J. B. Heng, V. Dimitrov, Y. V. Grinkova, C. Ho, T. Kim, D. Muller, S. Sligar, T. Sorsch, R. Twesten, R. Timp and G. Timp. The detection of DNA using a silicon nanopore. in Electron Devices Meeting, 2003. IEDM '03 Technical Digest. 2003: IEEE International.
16. D. W. Deamer and D. Branton, Characterization of nucleic acids by nanopore analysis, Acc. Chem. Res, 2002.35:817-825.
17. J. B. Heng, A. Aksimentiev, C. Ho, P. Marks, Y. V. Grinkova, S. Sligar, K. Schulten and G. Timp, The electromechanics of DNA in a synthetic nanopore, Biophysical Journal, 2006. 90(3): 1098-1106.

18. J. Mathe, A. Arinstein, Y. Rabin and A. Meller, Equilibrium and irreversible unzipping of DNA in a nanopore, Europhysics Letters, 2006. 73:128-134.
19. Y. Astier, O. Braha and H. Bayley, Toward single molecule DNA sequencing: Direct identification of ribonucleoside and deoxyribonucleoside 5'-monophosphates by using an engineered protein nanopore equipped with a molecular adapter, J. Am. Chem. Soc, 2006. 128; 1705-1710.
20. J. Nakane, M. Wiggin and A. Marziali, A nanosensor for transmembrane capture and Identification of single nucleic acid molecules, Biophys J. 87: 2004. 87:615-621.
21. M. Akeson, D. Branton, J. J. Kasianowicz, E. Brandin and D. W. D. Microsecond timescale discrimination among polycytidylic acid, polyadenylic acid, and polyuridylic acid as homopolymers or as segments within single RNA molecules, Biophys J., 1999. 77: 3227-3233.
22. Z. Siwy, L. Trofin, P. Kohli, L. A. Baker, C. Trautmann and C. R. Martin, Protein biosensors based on biofunctionalized conical gold nanotubes, J. Am. Chem. Soc., 2005. 127; 5000-5001.
23. J. J. Kasianowicz, Nanopores-Flossing with DNA, Nature Matls., 2004, 3: 355-356.
24. M. Muthukumar, Theory of sequence effects on DNA translocation through proteins and nanopores, Electrophoresis, 2003. 23:1417-1420.
25. P. Chen, J. J. Ciu, E. Brandin, Y. R. Kim, Q. Wang and D. Branton, Probing single DNA molecule transport using fabricated nanopores, Nano Lett., 2004. 4:2293-2298.
26. S. B. Smith, L. Finzi and C. Bustamante, Direct mechanical measurements of the elasticity of single DNA molecules by using magnetic beads, Science, 1992. 258: 1122-1126.
27. J. Kasianowicz, S. Henrickson, H. Weetall and B. Robertson, Simultaneous multianalyte detection with a nanometer-scale pore, Anal. Chem., 2001. 73:2268-2272.
28. A. Meller and D. Branton, Single molecule measurements of DNA transport through a nanopore, Electrophoresis, 2002.23:2583-2591.
29. J. Li, D. Stein, D. McCullan, D. Branton, M. J. Aziz and J. A. Golovchenko, Ion-beam sculpting at Nanometer length scales, Nature, 2001. 412:166-169.
30. A. Storm, J. Chen, X. Ling, H. Zandbergen and C. Dekker, Fabrication of solid-state nanopores with single-nanometer precision, Nature Mat, 2003, 2003. 2: 537-540.
31. H. Chang and et al. Towards Integrated Micro-machined silicon-based nanopores for characterization of DNA. in Proc. of Hilton Head Conf. 2004. Hilton Head, S. C.
32. H. Chang, S. Iqbal, 2. Stach, A. King, N. Zaluzec and R. Bashir, Fabrication and characterization of solid state nanopores using field emission scanning electron beam, App. Phys. Lett., 2006. 88: 103109.
33. M. J. Kim, M. Wanunu, D. C. Bell and A. Meller, Rapid Fabrication of Uniformly Sized Nanopores and Nanopore Arrays for Parallel DNA Analysis, Advanced Materials, 2006. 18: 3149-3153.
34. H. A. Held, A. Roychowdhury and S. A. Benner, C-5 modified nucleosides: Direct insertion of alkynyl-thio functionality in pyrimidines, Nucleosides, Nucleotides & Nucleic Acids, 2003. 22(4): 391-404.
35. P. Chen, T. Mitsui, D. B. Farmer, J. Golovchenko, R. G. Gordon and D. Branton, Atomic layer deposition to fine-tune the surface properties and diameters of fabricated nanopores, Nano Lett, 2004. 4: 1333.
36. A. Storm, J. J. H. Chen, H. W. Zandbergen and C. Dekker, Translocation of double-strand DMA through a silicon oxide nanopore, Phys. Rev. E, 2005.71:051903.
37. A. J. Storm, C. Storm, J. H. Chen, H. Zandbergen, W, J.-F. Joanny and C. Dekker, Fast DNA translocation through a solid-state nanopore, Nano Lett, 2005. 5: 1193.
38. D. Fologea, M. Gershow, B. Ledden, D. S. McNabb, J. A. Golovchenko and J. Li, Detecting single stranded DNA with a solid state nanopore, Nano Lett, 2005. 5:1905.
39. D. Fologea, J. Uplinger, B. Thomas, D. S. McNabb and J. Li, Slowing DNA translocation in a solid-state nanopore, Nano Lett, 2005. 5:1734.
40. J. B. Heng, C. Ho, T. Kim, R. Timp, A. Aksimentiev, Y. V. Grinkova, S. Sligar, K. Schulten and G. Timp, Sizing DNA using a nanometer-diameter pore, Biophys J, 2005. 87: 2905.
41. J. Heng, B., A. Aksimentiev, C. Ho, P. Marks, Y. V. Grinkova, S. Sligar, K. Schulten and G. Timp, Stretching DNA using the electric field in a synthetic nanopore, Nano Lett, 2005. 5: 1883.
42. P. Chen, J. Gu, E. Brandin, Y. Kim, Q. Wand and D. Branton, Probing single DNA molecule transport using fabricated nanopores, Nano Lett, 2004.4: 2293.
43. S. Wilk, M. Goryll, G. Laws, S. Goodnick and T. J. Thornton, Teflon-coated silicon apertures for supported lipid bilayer membranes, App. Phy. Lett, 2004.85: 3307-3309.
44. J. W. Lee and T. Thundat U.S. Pat. No. 6,905,586 Jun. 14, 2005
45. M. Zwolak and M. Di Ventra, Electronic Signature of DNA Nucleotides via Transverse Transport, Nano Lett, 2005. 5:421-424.
46. J. Lagerqvist, M. Zwolak and M. Di Ventra, Influence of the Environment and Probes on Rapid DNA Sequencing via Transverse Electronic Transport, Biophys J, 2007.93; 2384-2390.
47. X.-G. Zhang, P. S. Krstic, R. Zikic, J. C. Wells and M. Fuentes-Cabrera, First-Principles Transversal DNA Conductance Deconstructed, Biophys J., 2006.91: L04-L06.
48. M. E. Gracheva, A. Xiong, A. Aksimentiev, K. Schulten, G. Timp and J.-P. Leburton, Simulation of the electric response of DNA translocation through a semiconductor nanopore capacitor Nanotechnology, 2006. 17:622-633.
49. M. Zwolak and M. Di Ventra, Physical approaches to DNA sequencing and detection, Reviews of Modern Physics, 2007. in press: available at arXIV: 0708.2724.
50. B. Ashcroft, Q. Spadola, S. Qamar, P. Zhang, G. Kada, R. Bension and S. M. Lindsay, An AFM/Rotaxane Molecular Reading Head for Sequence-Dependent DNA Structure, J. Am. Chem. Soc, 2007. Submitted,
51. A. Salomon, D. Cahen, S. Lindsay, J. Tomfohr, V. B. Engelkes and C. D. Frisbie, Comparison of electronic transport measurements on organic molecules. Advanced Materials, 2003. 15:1881-1890.
52. D. D. Dunlap, R. Garcia, E. Schabtach and C. Bustamante, Masking generates contiguous segments of metal coated and bare DNA for STM imaging, Proc, Natl. Acad. Sci. (USA), 1993. 90: 7652-7655.
53. D. Porath, A. Bezrvadin, S. de Vries and C. Dekkar, Direct measurement of electrical transport through DNA molecules, Nature, 2000.403:635-638.
54. H.-W. Fink and C. Schoenberger, Electrical conduction through DNA molecules. Nature, 1999. 398:407-410.
55. A. Y. Kasumov, M. Kociak, S. Guéron, B. Reulet, V. T. Volkov, D. V. Klinov and E Bouchiat, Proximity-Induced Superconductivity in DNA, Science, 2001. 291: 280-282.
56. B. Xu, P. M. Zhang, X. L. Li and N. J. Tao, Direct Conductance Measurement of Single DNA Molecules in Aqueous Solution, Nanoletts, 2004.4:1105-1108.

57. J. Tomfohr and O. F. Sankey, Complex bandstructure, decay lengths and Fermi level alignment in simple molecular electronic systems, Phys. Rev. B, 2002. 65: 245105-245105-245112.

58. J. Tomfohr and O. F. Sankey, Simple estimates of the electron transport properties of molecules, Phys. Stat. Sol. B—Basic Research, 2002. 233: 59-69.

59. T. Smith, The hydrophillic nature of a clean gold surface, J. Colloid Interface Sci, 1980. 75: 51-53.

60. R. N. Barnett, C. L. Cleveland, A. Joy, U. Landman and G. B. Schuster, Charge Migration in DNA: Ion-Gated Transport, Science, 2001, 294:567-571.

61. X. D. Cui, A. Primak, X. Zarate, J. Tomfohr, O. F. Sankey, A. L. Moore, T. A. Moore, D. Gust, H. G, and S. M. Lindsay, Reproducible measurement of single-molecule conductivity, Science, 2001. 294: 571-574.

62. T. Merita and S. M. Lindsay, Determination of Single Molecule Conductances of Alkanedithiols by Conducting-Atomic Force Microscopy with Large Gold Nanoparticles, J. Am. Chem. Soc, 2007.129:7262-7263.

63. O. S. Wenger, Leigh, S. Villahermosa, R. M. Gray, H. B., Winkler, J. R., Electron Tunneling through Organic Molecules in Frozen Glasses, Science, 2005. 307: 99-102.

64. X. D. Cui, X. Zarate, J. Tomfohr, A. Primak, A. L. Moore, T. A. Moore, D. Gust, G. Harris. O. F. Sankey and S. M. Lindsay, Making electrical contacts to molecular monolayers, Nanotechnology, 2002.13:5-14.

65. X. D. Cui, X. Zarate, J. Tomfohr, A. Primak, A. L. Moore, T. A. Moore, D. Gust, G. Harris, O. F. Sankey and S. M. Lindsay, Bias Induced Forces and Contact charging of organic monolayers, Ultramicroscopy, 2002.92: 67-76.

66. X. D. Cui, A. Primak, X. Zarate, J. Tomfohr, O. F. Sankey, A. L. Moore, T. A. Moore, D. Gust, L. A. Nagahara and S. M. Lindsay, Changes in the electronic properties of a molecule when it is wired into a circuit, J. Phys. Chem B, 2002. B 106: 8609-8614.

67. J. K. Tomfohr and O. F. Sankey, Theoretical analysis of electron transport through organic molecules, J. Chem. Phys, 2004.120:1542-1554.

68. G. K. Ramachandran, A. M. Rawlett, T. J. Hopson, L. A. Nagahara, R. K. Tsui and S. M. Lindsay, Organic molecules in an electrical circuit: an AFM study of a negative differential resistance molecule. Materials Research Society Symposium Proceedings, 2002. 728 (Functional Nanostructured Materials through Multiscale Assembly and Novel Patterning Techniques): 211-215.

69. E. Gomar-Nadal, G. K. Ramachandran, F. Chen, T. Burgin, J. Veciana, C. Rovira, D. Amabilino and S. M. Lindsay, Self-Assembled Monolayers of TTF Derivatives on Gold: Characterization and Electron Transport Studies, J. Chem. Phys, 2004.108:7213-7218.

70. A. Rawlett, T. J. Hopson, L. Nagahara, R. Tsui, G. Ramachandran and S. Lindsay, Electrical measurements of dithiolated electronic molecules via conducting atomic force microscopy, Applied Physics Utters, 2002. 81: 3043-3045.

71. G. K. Ramachandran, T. J. Hopson, A. M. Rawlett, L. A. Nagahara, A. Primak and S. M. Lindsay, A Bond-Fluctuation Mechanism for Stochastic Switching in Wired Molecules, Science. 2003. 300:1413-1415.

72. G. K. Ramachandran, J. K. Tomfohr, O. F. Sankey, J. Li, X. Zarate, A. Primak, Y. Terazano, T. A. Moore, A. L. Moore, D. Gust, L. A. Nagahara and S. M. Lindsay, The Electron Transport Properties of a Carotene Molecule in a Metal-(Single-Molecule)-Metal Junction, J. Chem. Phys. B, 2003. 107:6162-6169.

73. S. M. Lindsay, Single Molecule Electronics and Tunneling in Molecules, Jap. J. Appl. Phys., 2002. 41:4867-4870.

74. S. M. Lindsay, Single Molecule Electronics, Interface, 2004. 3: 26-30.

75. D. M. Adams, L. Brus, C. E. D. Chidsey, S. Creager, C. Creutz, C. R. Kagan, P. V. Kamat, M. Lieberman, S. Lindsay, R. A. Marcus, R. M. Metzger, M. E. Michel-Beyerle, J. R. Miller, M. D. Newton, D. R. Rolison, O. Sankey, K. S. Schanze, J. Yardley and X. Zhu, Charge Transfer on the Nanoscale: Current Status, J. Phys. Chem., 2003.107:6668-6697.

76. J. K. Tomfohr, O. F. Sankey and S. Wang Rapid tunneling transit times for electrons and photons through periodic fragments, Phys. Rev. B, 2002.66:235105.

77. B. Xu and N. J. Tao, Measurement of Single-Molecule Resistance by Repeated Formation of Molecular Junctions, Science, 2003.301:1221-1223.

78. F. Chen, J. He, C. Nuckolls, T. Roberts, J. Klare and S. M. Lindsay, A molecular switch based on potential-induced changes of oxidation state, Nano Letters, 2005. 5: 503-506.

79. J. He, F. Chen, P. A. Liddell, J. Andresson, S. D. Straight, D. Gust, T. A. Moore, A. L. Moore, J. Li, O. F. Sankey and S. M. Lindsay, Switching of a photochromic molecule on gold electrodes: single molecule measurements, Nanotcchnology, 2005.16:695-702.

80. J. He, F. Chen, J. Li, O. F. Sankey, Y. Terazono, C. Herrero, D. Gust, T. A. Moore, A. L. Moore and S. M. Lindsay, Electronic Decay Constant of Carotenoid Polyenes from Single-Molecule Measurements, J. Am. Chem. Soc. (Communication), 2005. 127:1384-1385.

81. J. He and S. Lindsay, On the mechanism of negative differential resistance in ferrocenylundecanethiol self-assembled monolayers, J. Am. Chem. Soc., 2005. 127: 11932-11933.

82. J. Tomfohr, G. Ramachandran, O. F. Sankey and S. M. Lindsay, Making contacts to single molecules; Are we nearly there yet? In Introducing Molecular Electronics, G. Fagas and K. Richter, Editors. 2005, Springer: Berlin, p. 301-312.

83. J. He, Q. Fu, S. M. Lindsay, J. W. Ciszek and J. M. Tour, Electrochemical Origin of Voltage-Controlled Molecular Conductance Switching, J. Am. Chem. Soc., 2006. 128: 14828-14835.

84. I. Visoly-Fisher, K. Daie, Y. Terazono, C. Herrero, F. Fungo, L. Otero, E. Durantini, J. J. Silber, L. Sereno, D. Gust, T. A. Moore, A. L. Moore and S. M. Lindsay, Conductance of a biomolecular wire, Proc, Nat, Acad. Sci, 2006.103: 8686-8690.

85. X. Li, J. He, J. Hihath, B. Xu, S. M. Lindsay and N. J. Tao, Conductance of Single Alkanedithiols: Conduction Mechanism and Effect of Molecule-Electrode Contacts, J. Am. Chem. Soc., 2006.128:2135-2141.

86. J. He and S. M. Lindsay, Measuring Single Molecule Conductance with Break Junctions, Faraday Discussions, 2006. 131:145-154.

87. L. Venkataraman, Klare, J. E., Tam, I. W., Nuckolls, C., Hyberisen, M. S., Steigerwald, M. L., Single-Molecule Circuits with Well-Defined Molecular Conductance, Nano Lett, 2006. 6: 458-462.

88. L. Venkataraman, J. E. Klare, C. Nuckolls, M. S. Hybertsen and M. L. Steigerwald, Dependence of single-molecule junction conductance on molecular conformation, Nature, 2006. 442: 905-907.

89. S. M. Lindsay, Molecular wires and devices: Advances and issues, Faraday Discussions, 2006.131:403-409.

90. J. He, L. Lin, P. Zhang and S. M. Lindsay, Identification of DNA base-pairing via tunnel-current decay, Nano Letters, 2007. accepted for publication: (Copy appended).
91. K. A. Henningfeld, T. Arsian and S. M. Hecht, Alteration of DNA primary structure by DNA topoisomerase L Isolation of the covalent topoisonerasel-DNA binary complex in enzymatically competent form, J. Am. Chem. Soc., 1996. 118:11701-11713.
92. K. E. Yelm, A Simple Method for in situ Generation of Thiols from Thioacetates, Tetrahedron Letters, 1999.40: 1101-1102.
93. T.-C. Zheng, M. Burkart mid D. E. Richardson, A General and Mild Synthesis of Thioesters and Thiols from Halides, Tetrahedron Letters, 1999.40:603-606.
94. N. J. Tao, J. A. DeRose and S. M. Lindsay, Self Assembly of Molecular Superstructures studied by in situ STM: The DNA bases on Au(111), J. Phys. Chem., 1993.97:910-919.
95. T. A. Early, J. Olmsted and D. R. Kearns, Base pairing structure in the poly d(G-T) double helix: wobble base-pairs, Nucleic Acid Research, 1978. 5:1955-1970.
96. A. Vaught, T. W. Jing and S. M. Lindsay, Non-exponential tunneling in water near an electrode, Chemical Physics Utters, 1995. 236: 306-310.
97. B. Xu, X. Xiao and N. J. Tao, Measurements of Single-Molecule Electromechanical Properties, J. Am, Chem. Soc, 2003.125: 16164-16165.
98. S. M. Lindsay, T. Thundat and L. A. Nagahara, Adsorbate deformation as a contrast mechanism in STM images of biopolymers in an aqueous environment: Images of the unstained, hydrated DNA double helix, J. Microscopy, 1988.152, Pt 1:213-220.
99. H. T. Allawi and J. John SantaLucia, Thermodynamics of internal C*T mismatches in DNA, Nucleic Acids Research, 1998.26(11); 2694-2701
100. Y.-F. Yong, J. F. Kowalski and M. A. Lipton, Facile and Efficient Guanylation of Amines using Thioureas and Mukaiyama's Reagent, Journal of Organic Chemistry, 1997. 62: 1540-1542.
101. V. A. Bloom field, DNA condensation by multivalent cations, Biopolymers, 1998. 44: 269-282.
102. E. Shapir, H. Cohen, N. Borovok, A. B. Kotlyar and D. Porath, High-Resolution STM Imaging of Novel Poly(G)-Poly(C) DNA Molecules J. Phys. Chem B, 2006.110; 4430-4433,
103. C. R. Clemmer and T. P. Beebe, Graphite: A mimic for DNA and other Polymers, Science, 1991.251:640-642.
104. C. A. Mirkin and M. A. Ratner, Molecular Electronics, Annu. Rev. Phys. Chem, 1992.43: 7389-7396.
105. A. Aviram and M. A. Ratner, eds. Molecular Electronics: Science and Technology (Annals of the New York Academy of Sciences). Vol. 852. 1998, New York Academy of Sciences, NY.
106. G. Fagas and K. Richter, in Introducing Molecular Electronics, ed. 2005, Berlin: Springer.
107. S. M. Lindsay and M. A. Ratner, Molecular Transport Junctions: Clearing Mists, Advanced Materials, 2007.19: 23-31.
108. J. Park, A. N. Pasupathy, J. I. Goldsmith, C. Chang, Y. Yaish, J. R. Petta, M. Rinkoski, J. P. Sethna, H. D. Abruna, P. L. McEuen and D. C. Ralph, Coulomb Blockade and the Kondo Effect in single atom transistors, Nature, 2002.417: 722-725.
109. W. Liang, M. P. Shores, M. Bockrath, J. R. Long and H. Park, Kondo Resonance in a single molecule transistor, Nature, 2002.417:725-728.
110. L. H. Yu and D. Natelson, Transport in single-molecule transistors: Kondo physics and negative differential resistance, Los Alamos National Laboratory, Preprint Archive, Condensed Matter, 2004:1-15, arXiv:cond-mat/0405568.
111. D. Natelson, in Single-Molecule Transistors in press ed, ed, N. S. Nalwa. Vol. Handbook of Organic Electronics and Photonics. 2006: American Scientific Publishers.
112. A. A. Houck, J. Ubaziewicz, E. K. Chan, J. A. Folk and L. Chuang, Kondo effect in electromigrated gold break junctions, Nano Lett, 2005. 5:1685-1688.
113. M. D. Fischbein and M. Drndić, Nanogaps by direct lithography for high-resolution imaging and electronic characterization of nanostructures, App. Phy. Lett, 2006.88:063116.
114. M. D. Fischbein and M. Drndić, Sub-10 nm Device Fabrication in a Transmission Electron Microscope, Nano Lett, 2007. 7; 1329-1337.
115. C. Z. Li and N. J. Tao, Quantum transport in metallic nanowires fabricated by electrochemical deposition/dissolution, Applied Physics letters, 1998. 72:894-896.
116. J. G. Simmons, Generalized formula for the electric tunnel effect between similar electrodes separated by a thin insulating film, J. Appl. Phys, 1963. 34(6): 1793-1803.
117. J. M. v. Ruitenbeek, Quantum point contacts between metals, in Mesoscopic electron transport, L. L. Sohn, L. P. Kouwenhoven, and G. Schön, Editors. 1997, Kluwer Academic Publishers: Amsterdam, p. 549-579.
118. C. Walti, R. Wirtz, W. A. Germishuizen, D. M. D. Bailey, M. Pepper, A. P. J. Middelberg and A. G. Davies, Direct Selective Functionalization of Nanometer Separated Gold Electrodes with DNA Oligonucleotides, Langmuir, 2003.19:981-984.
119. C. J. Midler, J. M. Van Ruitenbeek and L. J. de Jong, Experimental observation of the transition from weak link to tunnel junction, Physica C, 1992.191:485-504.
120. D. Sarid, in Atomic Force Microscopy. 1992, New York: Oxford University Press.
121. C.-J. Lo, T. Aref and A. Bezryadin, Fabrication of symmetric sub-5 nm nanopores using focused ion and electron beams, Nanotechnology, 2006.17:3264-3267.
122. X. Yang and G. Zhang, Simulating the Structure and Effect of the Electrical Double Layer at Nanometer Electrodes, Nanotechnology, 2007.18: 335201, 335201-335209.
123. N. B. Leontis, J. Stombaugh and E. Westhof, The non-Watson-Crick base pairs and their associated isostericity matrices, Nucleic Acids Research, 2002.30(16): 3497-3531.
124. M. Egholm, O. Buchardt, L. Christensen, C. Behrens, S. M. Freier, D. A. Driver, R. H. Berg, S. K. Kim, B. Norden, and P. E. Nielsen, PNA hybridizes to complementary oligonucleotides obeying the Watson-Crick hydrogen-bonding rules. Nature. 1993. 365: 566-568.
125. D. Loakes, The Applications of universal DNA base analogues, Nucleic Acids Research, 2001. 29(12): 2437-2447.
126. Z. Guo, Q. Liu and L. M. Smith, Enhanced discrimination of single nucleotide polymorphisms by artificial mismatch hybridization, Nature Biotechnology, 1997.15: 331-335.
127. D. Burgner, M. D'Amato, D. F. Kwiatkowski and D. Loakes, Improved Allelic Differentiation Using Sequence-Specific Oligonucleotide Hybridization Incorporating an Additional Base-Analogue Mismatch, Nucleosides, Nucleotides and Nucleic Acids, 2004. 23(5): 755-765.

128. J. Luo, D. E. Bergstrom and F. Barany, Improving the fidelity of *Thermus thermophilus* DNA ligase, Nucleic Acids Research, 1996.24(14): 3071-3078.
129. H. Challa, M. L. Styers and S. A. Woski, Nitroazole Universal Bases in Peptide Nucleic Acids, Org. Lett, 1999.1(10): 1639-1641.
130. P. Zhang, M. Egholm. N. Paul, M. Pingle and D. E. Bergstrom, Peptide Nucleic Acid-DNA Duplexes Containing the Universal Base 3-Nitropyrrole, Methods, 2001. 23(2): 132-140.
131. B. Lohse, P. S. Ramanujam, S. Hvilsted and R. H. Berg, Photodimerization in pyrimidine-substituted dipeptides, J. Peptide Sci., 2005.11:499-505
132. R. H. E. Hudson, G. Li and J. Tse, The use of Sonogashira coupling for the synthesis of modified uracil peptide nucleic acid, Tetrahedron Letters 2002. 43 1381-1386.
133. N. Peyret, P. A. Seneviralne, H. T. Allawi and J. John SantaLucia, Nearest-Neighbor Thermodynamics and NMR of DNA Sequences with Internal A.A, C.C, G.G, and T.T Mismatches, Biochemistry 1999.38(12): 3468-3477.
134. H. T. Allawi and J. John SantaLucia, Thermodynamics and NMR of Internal GaT Mismatches in DNA, Biochemistry 1997.36(34): 10581-10594.
135. K. Seio, T. Sasami, A. Ohkubo, K. Ando and M. Sekine, Highly Selective Recognition of Cytosine over Uracil and Adenine by a Guanine Analogue, 2-N-Acetyl-3-deazaguamne, in 2'-O-Methyl-RNA/RNA and DNA Duplexes, J. AM. CHEM. SOC., 2007. 129(5): 1026-1027.
136. J. A. Doudna and J. H. Cate, RNA structure: crystal clear?, Current Opinion in Structural Biology 1997.7:310-316.
137. J. C. Parham and M. A. Templeton, Comparative Reactivities of Esters of Oncogenic and Nononcogenic Purine N-Oxides and Evidence of the Oxidation-Reduction Reactivity of Aromatic Nitremum Ions, Cancer Research, 1980.40:1475-1481.
138. B. K. Sarmah and N. C. Barua, Al—NiC12.6H2O-THF: A New, Mild and Neutral System for Selective Reduction of Organic Functional Groups, Tetrahedron 1991. 41 (40): 8587-8600.
139. M. Pauvert, P. Laine, M. Jonas and O. Wiest Toward an Artificial Oxidative DNA Phtolyase, J. Org. Chem, 2004.69(2); 643-648.
140. Z. Sun, S. Ahmed and L. W. McLaughlin, Synthesis of Pyridine C-Nucleosides as Analogues of the Natural Nucleosides dC and dU, J. Org. Chem, 2006. 71(7): 2922-2925.
141. N. Ramzaeva and F. Seela, 7-Substituted 7-deaza-2-deoxyguanosines: regioselective halogenation of pyrrolo[2,3-d]pyrimidine nucleosides. Helvetica Chimica Acta 1995. 78(5); 1083-1090.
142. H. C. Koppel, R. H. Springs, R. K. Robins and C. C. Cheng, Pyrimidines. I. Synthesis of Pyyimidinethiols, J. Org. Chem, 1961.26(3): 792-803.
143. J. John SantaLucia, R. Kierzek and D. H. Turner, Stabilities of Consecutive AC, CC, GoG, UC, and UmU Mismatches in RNA Internal Loops: Evidence for Stable Hydrogen-Bonded U4J and CC+ Pairs, Biochemistry 1991. 30(33): 8242-8251.
144. H. T. Allawi and J. John SantaLucia, Nearest-Neighbor Thermodynamics of Internal A:C Mismatches in DNA: Sequence Dependence and pH Effects, Biochemistry 1998. 37(26): 9435-9444.
145. S. S. Mallajosyula and S. K. Pati, Effect of Protonation on the Electronic Properties of DNA Base Pairs: Applications for Molecular Electronics, J. Phys. Chem. B, 2007. 111: 11614-11618.
146. K.-Y. Lin and M. D. Matteucci, A Cytosine Analogue Capable of Clamp-Like Binding to a Guanine in Helical Nucleic Acids, J. Am. Chem. Soc., 1998. 120(33): 8531-8532.
147. S. C. Holmes, A. A. Arzumanov and M. J. Gait, Stoic inhibition of human immunodeficiency virus type-1 Tat-dependent trans-activation in vitro and in cells by oligonucleotides containing 2-O-methyl G-clamp ribonucleoside analogues, Nucleic Acids Research, 2003. 31(11): 2759-2768.
148. C. Cheong, J. Ignacio Tinoco and A. Chollet, Thermodynamic studies of base pairing involving 2,6-diaminopurine, Nucleic Acids Research, 1988. 16(11): 5115-5122.
149. S. A. Strobel, T. R. Cech, N. Usman and L. Beigelmad, The 2,6-Diaminopurine Riboside5-Methylisocytidine Wobble Base Pair: An Isoenergetic Substitution for the Study of GU Pairs in RNA, Biochemistry 1994. 33(46): 13824-13835.
150. B. L. Gaffney, L. A. Marky and R. A. Jones, Synthesis and physical characterization of d[CGT(2-NH2)ACG], d[CGU(2-NH2ACG] and d[CGT(2-NH2)AT(2-NH2)ACG], Tetrahedron 1984.40(1): 3-13
151. J. Booth, W. J. Cummins and T. Brown, An analogue of adenine that forms an "A:T" base pair of comparable stability to G:C, Chem. Commun. 2004. 10:2208-2209.
152. S. W. Schneller and R. S. Hosmane, Chlorination of 1H-pyrrolo[3,2-c]pyridine-4,6(5H,7H)-dione (3,7-dideazaxanthine) and its 5-methyl derivative, Journal of Heterocyclic Chemistry, 1978. 15(2): 325-326.
153. H. Yamamoto, T. Terasawa, A. Nakamura, K. Kawabata, H. Takasugi, H. Tanaka, S. Matsumoto, Y. Matsumoto and S. Tawara, Orally Active Cephalosporins. Part 3: Synthesis, Structure-Activity Relationships and Oral Absorption of Novel C-3 Heteroarylmethylthio Cephalosporins, Bioorganic & Medicinal Chemistry, 2001. 9:465-475.
154. D. E. Bergstrom and P. Zhang, An efficient route to C-4 linked imidazole nucleosides: synthesis of 2-carbamoyl-4-(2'-deoxy-b-D-ribofurinosyl)imidazole, Tetrahedron letters, 1991. 32(45): 6485-6488.
155. K. J. Merchant, Potassium trimethylsilanolate mediated hydrolysis of nitriles to primary amides. Tetrahedron Letters, 2000.41:3747-3749.
156. B. R. Brooks, R. E. Bruccoleri, B. D. Olafson, D. J. States, S. Swaminathan and M. Karplus, Charmm—a Program for Macromolecular Energy, Minimization, and Dynamics Calculations, Journal of Computational Chemistry, 1983.4(2): 187-217.
157. D. A. Pearlman, D. A. Case, J. W. Caldwell, W. R. Ross, I. T. E. Cheatham, S. DeBolt, D. Ferguson, G. Seibel and P. Kollman, AMBER, a computer program for applying molecular mechanics, normal mode analysis, molecular dynamics and free energy calculations to elucidate the structures and energies of molecules, Comp. Phys. Commun, 1995.91:1-41.
158. M. W. Schmidt, K. K. Baldridge, J. A. Boatz, S. T. Elbert M. S. Gordon, J. H. Jensen, S. Koseki, N. Matsunaga, K. A. Nguyen, S. J. Su, T. L. Windus, M. Dupuis and J. A. Montgomery, General Atomic and Molecular Electronic-Structure System. Journal of Computational Chemistry, 1993. 14(11): 1347-1363.
159. R. A. Kendall, E. Apra, D. E. Bernholdt, E. J. Bylaska, M. Dupuis, G. I. Fann, R. J. Harrison, J. L. Ju, J. A.

159. Nichols, J. Nieplocha, T. P. Straatsma, T. L. Windus and A. T. Wong, High performance computational chemistry: An overview of NWChem a distributed parallel application, Computer Physics Communications, 2000. 128(1-2): 260-283.
160. G. Kresse and J. Furthmuller, Efficient iterative schemes for ab initio total-energy calculations using a plane-wave basis set, Phys. Rev. B, 1996. 55:11169-11186.
161. S. Baroni, S. d. Gironcoli and A. D. Corsa, www.p-wscf.org.
162. O. F. Sankey and D. J. Niklewski, Abinitio Multicenter Tight-Binding Model for Molecular-Dynamics Simulations and Other Applications in Covalent Systems, Physical Review B, 1989. 40(6): 3979-3995.
163. P. Jelinek, H. Wang, J. P. Lewis, O. F. Sankey and J. Ortega, Multicenter approach to the exchange-correlation interactions in ab initio tight-binding methods, Physical Review B, 2005. 71(23).
164. P. Ordejon, E. Artacho and J. M. Soler, Self-consistent order-N density functional calculations for very large systems, Phys. Rev. B, 1996.53: 10441-10444.
165. A. P. Horsfield, P. D. Godwin, D. G. Pettifor and A. P. Sutton, Computational materials synthesis. 1. A tight-binding scheme for hydrocarbons, Physical Review B, 1996. 54(22): 15773-15775.
166. U. F. Keyser, B. N. Koelman, S. van Dorp, D. Krapf, R. M. M. Smeets, S. G. Lemay, N. H. Dekker and C. Dekker, Direct forcemeasurements on DNA in a solid-state nanopore, Nature Physics, 2006.2:473-477.
167. C. Bustamante, J. C. Macosko and G. J. L. Wuite, Grabbing the cat by the tail: Manipulating molecules one by one. Nature Reviews Molecular Cell Biology, 2000. 1: 130-136.
168. C. Gosse and V. Croquette, Magnetic Tweezers: Micromanipulation and Force Measurement at the Molecular Level, Biophys J., 2002.82: 3314-3329.
169. H. Shang and G. U. Lee, Magnetic Tweezers Measurement of the Bond Lifetime-Force Behavior of the IgG-Protein A Specific Molecular Interaction, J. Am. Chem. Soc, 2007. 129: 6640-6646.
170. J. Sanchez-Quesada, A. Saghatelian, S. Cheley, H. Bayley, M. R. Ghadiri and M. Reza, Single DNA Rotaxanes of a transmembrane pore, Angew. Chem. Int. Ed., 2004. 43:3063-3067.
171. H. B. Gamper, K. Arar, A. Gewirtz and Y. M. Hou, Unrestricted Hybridization of Oligonucleotides to Structure-Free DNA, Biochemistry, 2006. 45:6978-6986.
172. J. R. Sampson US patent number US 2005/0032053 Feb. 10, 2005
173. X. C. Zhao, C. M. Payne, P. T. Cummings and J. W. Lee, Single-strand DNA molecule translocation through nanoelectrode gaps, Nanotechnology, 2007. 18(42).
174. A. Aksimentiev, J. B. Heng, G. Timp and K. Schulten, Microscopic kinetics of DNA translocation through synthetic nanopores, Biophysical Journal, 2004.87(3): 2086-2097.
175. J. Jeon and M. S. Chun, Structure of flexible and semiflexible polyelectrolyte chains in confined spaces of slit micro/nanochannels, Journal of Chemical Physics, 2007. 126(15).
176. W. D. Cornell, P. Cieplak, C. I. Bayly, I. R. Gould, K. M. Merz, D. M. Ferguson, D. C. Spellmeyer, T. Fox, J. W. Caldwell and P. A. Kollman, A second generation force field for the simulation of proteins, nucleic acids, and organic molecules (vol 117, pg 5179, 1995), Journal of the American Chemical Society, 1996. 118(9): 2309-2309.
177. D. L. Ermak and J. A. McCammon, Brownian Dynamics with Hydrodynamic Interactions, Journal of Chemical Physics, 1978.69(4): 1352-1360.
178. R. S. Graham and R. G. Larson, Coarse-grained brownian dynamics simulations of electrophoresis of DNA molecules from generalized reptation models, Macromolecules, 2007. 40(2): 366-378.
179. M. Muthukumar, Mechanism of DNA transport through pores, Annual Review of Biophysics and Biomolecular Structure, 2007. 36: 435-450.
180. C. Carneheim, P.-O. Anderson, M. Bakhuizen and L. Malm U.S. Pat. No. 6,215,798 Apr. 10, 2001.
181. C. R. Cantor, P. R. Schimmel, Biophysical Chemistry (W.H. Freeman, San Francisco, 1980).
182. V. Mujica, M. Kemp, M. A. Ratner, J. Chem. Phys. 101, 6849 (1994).
183. R. Landauer, J. Phys. Condens. Matter 1, 8099 (1989).
184. Y. Imry, R. Landauer, Revs. Mod. Phys. 71, S306 (1999).
185. A. M. Kuznetsov, I. Ulstrup, Electron transfer in chemistry and biology (Wiley, New York, 1999).
186. G. A. Jeffrey, W. Saenger, Hydrogen bonding in biological structures (Springer, Berlin, 1991).
187. P. de-los-Santos-Álvarez, M. J. Lobo-Castañón, A. J. Miranda-Ordieres, P. Tuñón-Blanco, Anal Bioanal Chem 378, 104-118 (2004).
188. K. A. Schug, W. Lindner, Chem. Rev. 105, 67 (2005).
189. C. A. McDermott, M. T. McDermott, J. B. Green, M. D. Porter, J. Phys. Chem. 99, 13257 (1995).
190. H. Tanaka, C. Hamai, T. Kanno, T. Kawai, Surface Science 423, L611 (1999).

Base-Reader (BR): A class of molecule, natural or manmade that contains a predetermined pattern and spacing of Hydrogen bond donors and acceptors fixed in space on a molecular scaffold to allow the molecule to bond and recognize molecules with complementary patterns and spacing of Hydrogen bond donors and acceptors.

Universal-Base-Reader (UBR): A class of molecule, natural or manmade that contains sufficient predetermined pattern and spacing of Hydrogen bond donors and acceptors fixed in space on a molecular scaffold to allow the molecule through conformational changes to bond and recognize all molecules of interest with complementary patterns and spacing of Hydrogen bond donors and acceptors.

Adenine-Base-Reader (ABR): A class of molecule, natural or manmade that contains a predetermined pattern and spacing of hydrogen bond donors and acceptors fixed in space on a molecular scaffold to allow the Base-Reader to bond and recognize adenine (abbreviated A). A few examples of an ABR class of molecule are thymine (T), uracil (U) and Riboflavin. These molecules have complementary patterns and spacing of Hydrogen bond donors and acceptors to recognize adenine (A).

Cytosine-Base-Reader (CBR): A class of molecule, natural or manmade that contains a predetermined pattern and spacing of Hydrogen bond donors and acceptors fixed in space on a molecular scaffold to allow the Base-Reader to bond and recognize cytosine (abbreviated C). A few examples of a CBR class of molecule are guanine (abbreviated G) and isoguanine. These molecules have complementary patterns and spacing of Hydrogen bond donors and acceptors to recognize cytosine (C).

Guanine-Base-Reader (GBR): A class of molecule, natural or manmade that contains a predetermined pattern and spacing of Hydrogen bond donors and acceptors fixed in space on a molecular scaffold to allow the Base-Reader to bond and recognize guanine (abbreviated G). A few examples of a GBR class of molecule are cytosine (C) and 5-Methylcytosine. These molecules have complementary patterns and spacing of Hydrogen bond donors and acceptors to recognize guanine (G).

Thymine-Base-Reader (TBR): A class of molecule, natural or manmade that contains a predetermined patient and spacing of Hydrogen bond donors and acceptors fixed in space on a molecular scaffold to allow the Base-Reader to bond and recognize thymine (abbreviated T) and or uracil (U). A few examples of a TBR class of molecule are adenine (abbreviated A) and Coenzyme A. These molecules have complementary patterns and spacing of Hydrogen bond donors and acceptors to recognize thymine (T) and uracil (U).

Electrode Attachment Molecule (EAM): A class of molecule that has the properties required to make a good electrical and mechanical contact/bond with a conductive or semi-conductive electrode. One exemplary example of such a molecule is an alkane thiol on gold conductor. Sulfur has particular affinity for gold, with a binding energy in the range of 20-35 kcal/mol (85-145 kJ/mol). An alkane with a thiol head group will stick to the gold surface and can have a linker molecule covalently bonded to it and a base reader or a phosphate group recognition molecule linked to it.

Linker Molecule (LM): A class of molecule that has the properties required to make a good electrical and mechanical contact/bond with an Electrode Attachment Molecule and a Phosphate Group Recognition Molecule or a Base Reader. One exemplary example of such a molecule is a Poly (ethylene glycol) oligomer.

Phosphate Group Recognition Molecule (PGRM): A class of molecule that will because of its favorable structural and chemical properties form one or more hydrogen bonds with the phosphate groups that comprise the backbone of a biopolymer. One of many exemplary example of such a molecule is Guanidinium.

Guanidinium IUPAC name 1,1-(dithiodiethylene) diguanidine. Guanidinium is a chaotrope that causes molecular structure to be disrupted; in particular, those formed by noncovalent forces such as hydrogen bonding. Van der Waals interactions, and the hydrophobic effect. It is also used as a general protein denaturant. Guanidinium has the ability to hydrogen bond to the phosphate groups attached to the sugar backbone of the DNA molecule. The Hydrogen bonding occurs between the favorable spaced atomic structure of the oxygen atoms of the phosphate groups and the two free $NH_2$ amine ends of the guanidinium. Guanidinium is from the group of Guanidines which are a group of organic compounds sharing a common functional group with the general structure (R1R2N1)(R3R4N2) C=N3-R5. The central bond within this group is dial of an imine. In the simple case for Guanidinium the R's are Hydrogen H so the structure looks like $(N1H_2)$ $(N2H_2)C$—N3-R5. The third Nitrogen may be replaced by an oxygen or a carbon and still not affect the desired functionality. Many molecules have the ability to hydrogen bond to the phosphate groups and therefore can function as part of a DNA reader. The important characteristics are the ability to electrically conduct, the ability to hydrogen bond to the phosphate groups and the ability to attach by covalent bond to electrically conductive linker molecules.

Cystamine is an organic disulfide. IUPAC name 2,2'-Dithiobis(ethylamine). It is formed when cystine is heated, the result of decarboxylation. Cystamine is an unstable liquid and is generally handled as the dihydrochloride salt, $C_4H_{12}N_2S_2 \cdot 2HCl$, which is stable to 203-214° C. at which point it decomposes. Cystamine is toxic if swallowed or inhaled and potentially harmful by contact.

N,N-bis(tert-butoxycarbonyl)thiourea guanylating reagent used in making guanidinium Bernatowicz, M. S.; Wu, Y.; Matsueda, G. R. Tetrahedron Lett. 1993, 34, 3389.

2-chloro-1-methylpyridinium iodide reagent is used to make guanidinium.

DMF (Dimethylformamide) is the organic compound with the formula $(CH_3)_2NC(O)H$. Commonly abbreviated DMF, this colorless liquid is miscible with water and majority of organic liquids. DMF is a common solvent for chemical reactions.

TCEP (tris(2-carboxyethyl)phosphine) is a reducing agent frequently used in biochemistry and molecular biology applications. It is often prepared and used as a hydrochloride salt. TCEP is also available as a stabilized solution at neutral pH and immobilized onto an agarose gel support to facilitate removal of the reducing agent. TCEP is often used as a reducing agent to break disulfide bonds within and between proteins as a preparatory step for gel electrophoresis.

Tris is an abbreviation for (trishydroxymethylaminomethane) which is also known by its IUPAC definition of 2-amino-2-hydroxymethyl-1,3-propanediol. It is widely used as a component of buffer solutions, such as in TAE and TBE buffers used in biochemistry, with an effective pH range between 7.0 and 9.2. Tris is often used when working with nucleic acids. Tris is an effective buffer for slightly basic solutions, which keeps DNA deprotonated and soluble in water. Tris is commonly combined with EDTA to make TE buffer for stabilization and storage of DNA. EDTA binds to divalent cations, particularly magnesium (Mg2+). These ions are necessary co-factors for many enzymes; Magnesium is a co-factor for many DNA-modifying enzymes. Tris is toxic to mammalian cells, and reacts strongly with pH electrodes. It is a primary amine, and can thus react with aldehydes.

Tris-HCl is a solution frequently used in biochemistry made from Tris base and concentrated hydrochloric acid (HClaq). To make 1 mol/L Tris-Cl dissolve 121.1 g of tris base in 700 ml of double distilled water, bring to desired pH with concentrated HClaq (usually 7.5 or 8.0), add double distilled water to 1 L, filter with 0.5 µm filter, autoclave, and store at room temperature.

PEG (Polyethylene glycol) is a polymer comprising repeating subunits of identical structure, called monomers, and is the most commercially important polyether. Poly (ethylene glycol) refers to an oligomer prepared by polymerization of ethylene oxide. Derivatives of PEG are commonly used, the most common derivative being the methyl ether (methoxypoly (ethylene glycol)), abbreviated mPEG.

The melting points of PEG and mPEG vary depending on the formula weight of the polymer. PEG has the structure HO—(CH2-CH2-O)n-H and is used as a linker molecule for its flexibility and length.

STM (Scanning tunneling microscopy) is a powerful technique for viewing surfaces at the atomic level. The STM is based on the concept of quantum tunneling. When a conducting tip is brought very near to a metallic or semiconducting surface, a bias between the two can allow electrons to tunnel through the vacuum between them. Variations in current as the probe passes over the surface are translated into an image.

PNA (Peptide nucleic acid) is a chemical similar to DNA or RNA. PNA does not occur naturally but is artificially synthesized. DNA and RNA have a deoxyribose and ribose sugar backbone, respectively, whereas PNA's backbone comprises repeating N-(2-aminoethyl)-glycine units linked by peptide bonds. The various purine and pyrimidine bases are linked to the backbone by methylene carbonyl bonds. Since the backbone of PNA contains no charged phosphate groups, the binding between PNA/DNA strands is stronger than between DNA/DNA strands due to the lack of electrostatic repulsion. PNAs are not easily recognized by either nucleases or proteases, making them resistant to enzyme degradation. PNAs are also stable over a wide pH range.

TEM (Transmission electron microscopy) is an imaging technique whereby a beam of electrons is transmitted through a specimen. An image is formed, magnified and directed to appear either on a fluorescent screen or on layer of photographic film or is detected by a sensor such as a CCD camera.

Coenzyme A (CoA, CoASH, or HSCoA) is a coenzyme, notable for its role in the synthesis and oxidization of fatty adds, and the oxidation of pyruvate in the citric acid cycle. It is adapted from cysteamine, pantothenate, and adenosine triphosphate.

What is claimed is:

1. A molecular recognition device configured to identify at least one portion of a target molecule, the device comprising:
    a partition having a first side, a second side, and a thickness therebetween;
    at least one constriction having a first end open to the first side and a second end open to the second side, wherein:
        the at least one constriction includes a diameter, an interior wall, a perimeter, and a length corresponding to at least the thickness, and
        the diameter is configured to pass therethrough target molecules from the first side to the second side, a single target molecule at a time;
    a first electrode arranged along at least a portion of the perimeter of the interior wall at a first position along the length of the constriction,
    a second electrode arranged along at least a portion of the perimeter of the interior wall at a second position along the length of the constriction spaced away from the first position establishing a gap therebetween,
    wherein:
    each of the first and second electrodes includes an affinity element functionalized thereto;
    at least a portion of each target molecule translocating through the constriction forms one or more temporary non-covalent bonds with each of the affinity elements of the respective electrodes upon passing adjacent the gap thereby establishing a temporary electrical circuit between the first electrode and the second electrode,
    the circuit is configured to produce one or more observable electrical characteristics thereof during the temporary binding, and
    the one or more characteristics correspond to a signature of at least a portion of the target molecule for comparison against known signature currents for different target molecules or different portions of target molecules so as to identify at least the portion of each translocated target molecule.

2. The device of claim 1, wherein the gap comprises an insulating material.

3. The device of claim 1, wherein the partition is configured to separate a first chamber arranged to the first side of the partition and containing target molecules, from a second chamber arranged to the second side of the partition.

4. The device of claim 3, wherein at least one of the first chamber and the second chamber comprises a microfluidic channel.

5. The device according to claim 1, wherein at least one of the electrodes is connected to a respective affinity element via a linker molecule.

6. The device according to claim 1, further comprising a pair of polarization electrodes configured to at least aid in translocating a target molecule through the constriction.

7. The device according to claim 1, further comprising current monitoring means for monitoring the one or more characteristics of the current.

8. The device according to claim 7, wherein the current monitor means monitors at least one of a time-varying component of the electrical current and a strength component of the produced current.

9. The device according to claim 1, wherein the affinity element comprises a phosphate grabber.

10. The device according to claim 9, wherein the phosphate grabber comprises a guanidinium moiety.

11. The device according to claim 1, wherein the affinity element comprises 4-(mercaptomethyl)-1H-imidazole-2-carboxamide.

12. The device according to claim 1, further comprising first and second polarization electrodes configured for polarizing the constriction to at least aid in translocating target molecules.

13. The device according to claim 1, wherein the device is further configured to process a sample containing target molecules at a speed of less than 5 mm/s.

14. The device according to claim 1, wherein the device is further configured to realize an observable current between about 10 pico-amps to about 1 nano-amp.

15. The device according to claim 1, wherein the first position of the first electrode is spaced from the first side of the partition, and wherein the partition material between the first side and the first position is an insulating material.

16. The device according to claim 15, wherein the second position of the second electrode is spaced from the second side of the partition, and wherein the partition material between the second side and the second position is an insulating material.

17. The device according to claim 1, wherein the partition adjacent at least the constriction comprises alternating layers of insulating material and the first and second electrodes.

18. The device of claim 1, wherein the circuit is configured to produce an observable current during the temporary corresponding to the one or more associated characteristics.

19. A molecular recognition device configured to identify at least one portion of a target molecule, the device comprising:
    at least one partition having a first side, a second side, and a thickness therebetween;
    a plurality of constrictions, each having a first end open to the first side of at least one partition and a second end open to the second side of at least one partition, wherein:
        each constriction includes a diameter, an interior wall, a perimeter, and a length corresponding to at least the thickness, and
        the diameter is configured to pass therethrough target molecules from the first side to the second side, a single target molecule at a time;
    a first electrode arranged along at least a portion of the perimeter of the interior wall at a first position along the length of each constriction,
    a second electrode arranged along at least a portion of the perimeter of the interior wall at a second position along the length of each constriction spaced away from the first position establishing a gap therebetween, wherein:

each of the first and second electrodes includes an affinity element functionalized thereto;

at least a portion of each target molecule translocating through the constriction forms one or more temporary non-covalent bonds with each of the affinity elements of the respective electrodes upon passing adjacent the gap thereby establishing a temporary electrical circuit between the first electrode and the second electrode, the circuit is configured to produce one or more observable electrical characteristics thereof during the temporary binding, and the one or more characteristics correspond to a signature of at least a portion of the target molecule for comparison against known signature currents for different target molecules or different portions of target molecules so as to identify at least the portion of each translocated target molecule.

20. The device of claim 19, wherein the plurality of constrictions are organized in an array.

21. The device of claim 19, wherein the circuit is configured to produce an observable current during the temporary corresponding to the one or more associated characteristics.

* * * * *

UNITED STATES PATENT AND TRADEMARK OFFICE
CERTIFICATE OF CORRECTION

PATENT NO. : 10,330,632 B2
APPLICATION NO. : 15/203383
DATED : June 25, 2019
INVENTOR(S) : Stuart Lindsay and Peiming Zhang It is certified that error appears in the above-identified patent and that said Letters Patent is hereby corrected as shown below:

In the Specification

In Column 1, Line 36:
Delete the following paragraph:
"STATEMENT REGARDING FEDERALLY SPONSORED RESERACH & DEVELOPMENT
This invention was made with government support under NHGRI Grant Nos. 1R21 HG3061 1R21 HG004378-01 and GM 21966, awarded by the National Institute of Health. The government has certain rights in this invention."

Insert the following paragraph:
-- GOVERNMENT SUPPORT CLAUSE
This invention was made with government support under HG003061, HG004378, GM021966 awarded by the National Institutes of Health. The government has certain rights in the invention. --

Signed and Sealed this
Twenty-fourth Day of December, 2019

Andrei Iancu
*Director of the United States Patent and Trademark Office*